US 8,445,650 B2

(12) United States Patent
Simpson et al.

(10) Patent No.: US 8,445,650 B2
(45) Date of Patent: May 21, 2013

(54) MUTANT BOTULINUM NEUROTOXIN SEROTYPE A POLYPEPTIDE AND USES THEREOF

(75) Inventors: Lance L. Simpson, Moorestown, NJ (US); Mohammed Elias, Voorhees, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 153 days.

(21) Appl. No.: 12/679,936

(22) PCT Filed: Sep. 25, 2008

(86) PCT No.: PCT/US2008/011092
§ 371 (c)(1),
(2), (4) Date: May 27, 2010

(87) PCT Pub. No.: WO2009/042165
PCT Pub. Date: Apr. 2, 2009

(65) Prior Publication Data
US 2010/0247560 A1    Sep. 30, 2010

Related U.S. Application Data

(60) Provisional application No. 60/995,145, filed on Sep. 25, 2007.

(51) Int. Cl.
*A61K 39/08* (2006.01)
*C12P 21/06* (2006.01)
(52) U.S. Cl.
USPC ..................... 530/391.1; 530/350; 424/190.1
(58) Field of Classification Search
None
See application file for complete search history.

(56) References Cited

U.S. PATENT DOCUMENTS

| 5,919,665 | A | 7/1999 | Williams | 435/71.1 |
|---|---|---|---|---|
| 6,051,239 | A | 4/2000 | Simpson et al. | 424/239.1 |
| 6,287,566 | B1 | 9/2001 | Dertzbaugh | 424/190.1 |
| 6,667,158 | B1 | 12/2003 | Bavari et al. | 435/7.32 |
| 7,645,570 | B2 * | 1/2010 | Fernandez-Salas et al. | 435/4 |
| 7,985,554 | B2 * | 7/2011 | Chapman et al. | 435/7.1 |
| 2002/0031523 | A1 | 3/2002 | Druilhe et al. | 424/185.1 |
| 2003/0009025 | A1 | 1/2003 | Smith et al. | 536/23.7 |

(Continued)

FOREIGN PATENT DOCUMENTS

| AU | 2005281830 | * | 3/2006 |
|---|---|---|---|
| WO | WO 00/02524 | | 1/2000 |

(Continued)

OTHER PUBLICATIONS

Rummel et al (Molecular Microbiology, 2002, 51(3), p. 631-643).*

(Continued)

*Primary Examiner* — Albert Navarro
*Assistant Examiner* — Ginny Portner
(74) *Attorney, Agent, or Firm* — Caesar, Rivise, Bernstein, Cohen & Pokotilow, Ltd.

(57) ABSTRACT

Modified polypeptides based on the *botulinum* neurotoxin A heavy chain containing the double mutation Trp-Tyr->Leu-Ser in the ganglioside binding motif Ser-X-Trp-Tyr do not bind polysialogangliosides and nerve endings. The polypeptides are useful in the preparation of nontoxic vaccines against the effects of *C. botulinum* infection. The modified polypeptides are also useful as vehicles for the transepithelial delivery of diagnostic and therapeutic entities, through formation of conjugates between the polypeptides and the diagnostic or therapeutic entities.

29 Claims, 3 Drawing Sheets

U.S. PATENT DOCUMENTS

| | | | |
|---|---|---|---|
| 2003/0185850 A1 | 10/2003 | Dertzbaugh | 424/190.1 |
| 2003/0215468 A1 | 11/2003 | Williams et al. | 424/239.1 |
| 2004/0013687 A1 | 1/2004 | Simpson et al. | 424/190.1 |
| 2007/0299008 A1* | 12/2007 | Rummel | 514/12 |

FOREIGN PATENT DOCUMENTS

| | | |
|---|---|---|
| WO | WO 00/05252 | 2/2000 |
| WO | WO 03/012117 | 2/2003 |
| WO | WO 03/006770 | 8/2003 |

OTHER PUBLICATIONS

Rummel, A et al, 2004, Molecular Biology, vol. 51(3), pp. 631-643, The Hcc-domain of botulinum neurotoxins A and B exhibits a sinular ganglioside binding site displaying serotype specific carbohydrate interaction.*

LePenotiere et al., "Expression of a Large, Nontoxic Fragment of Botulinum Neurotoxin Serotype A and Its Use as an Immunogen," *Toxicom*, 1995, vol. 33, No. 10, pp. 1383-1386.

Swaminathan et al., "Structural analysis of the catalytic and binding sites of *Clostridium botulinum* neurotoxin B," *Nature Structural Biology*, Aug. 2000, vol. 7, No. 8, pp. 693-699.

Ihara et al., "Sequence of the gene for *Clostridium botulinum* type B neurotoxin associated with infant botulism, expression of the C-terminal half of heavy chain and its binding activity," *Biochimica et Biophysica Acta* 1625 (2003), pp. 19-26.

Lacy et al., "Crystal structure of botulinum neurotoxin type A and implications for toxicity," *Nature Structural Biology*, Oct. 1998, vol. 5, No. 10, pp. 898-902.

Lacy et al., "Sequence Homology and Structural Analysis of the Clostridial Neurotoxins," *J. Mol. Biol.* (1999), 291, pp. 1091-1104.

Turton et al., "Botulinum and tetanus neurotoxins: structure, function and therapeutic utility," *TRENDS in Biochemical Sciences*, vol. 27, No. 11, Nov. 2002, pp. 552-558.

Byrne et al., "Development of vaccines for prevention of botulism," *Biochimic* 82 (2000), pp. 955-966.

Binz et al., "The Complete Sequence of Botulinum Neurotoxin Type A and Comparison with Other Clostridial Neurotoxins," *The Journal of Biological Chemistry*, vol. 265, No. 16, Issue of Jun. 5, pp. 9153-9158, 1990.

Ginalski et al., "Structure-based sequence alignment for the β-trefoil subdomain of the clostridial neurotoxin family provides residue level information about the putative ganglioside binding site," *Federation of European Biochemical Studies (FEBS) Letters* 482, 2000, pp. 119-124.

Lalli et al., "Functional characterization of tetanus and botulinum neurotoxins binding domains," *Journal of Cell Science* 112, 1999, pp. 2715-2724.

Rummel et al., "The $H_{CC}$-domain of botulinum neurotoxins A and B exhibits a singular ganglioside binding site displaying serotype specific carbohydrate interaction," *Molecular Microbiology*, 2004, 51(3), pp. 631-643.

Clayton et al., "Protective Vaccination with a Recombinant Fragment of *Clostridium botulinum* Neurotoxin Serotype A Expressed from a Synthetic Gene in *Escherichia coli*," *Infection and Immunity*, Jul. 1995, pp. 2738-2742.

\* cited by examiner

SEQUENCE LISTING

<160> NUMBER OF SEQ ID NOS: 33

<210> SEQ ID NO 1
<211> LENGTH: 27
<212> TYPE: DNA
<213> ORGANISM: Artificial
<220> FEATURE:
<223> OTHER INFORMATION: chemically synthesized

<400> SEQUENCE: 1
tttataggat tttggcagtt taataat                               27

<210> SEQ ID NO 2
<211> LENGTH: 27
<212> TYPE: DNA
<213> ORGANISM: Artificial
<220> FEATURE:
<223> OTHER INFORMATION: chemically synthesized

<400> SEQUENCE: 2
attattaaac tgccaaaatc ctataaa                               27

<210> SEQ ID NO 3
<211> LENGTH: 27
<212> TYPE: DNA
<213> ORGANISM: Artificial
<220> FEATURE:
<223> OTHER INFORMATION: chemically synthesized

<400> SEQUENCE: 3
gtagcaagta atttgtataa tagacaa                               27

<210> SEQ ID NO 4
<211> LENGTH: 27
<212> TYPE: DNA
<213> ORGANISM: Artificial
<220> FEATURE:
<223> OTHER INFORMATION: chemically synthesized

<400> SEQUENCE: 4
ttgtctatta tacaaattac ttgctac                               27

<210> SEQ ID NO 5
<211> LENGTH: 27
<212> TYPE: DNA
<213> ORGANISM: Artificial
<220> FEATURE:
<223> OTHER INFORMATION: chemically synthesized

<400> SEQUENCE: 5
gcaagtaatt ggtctaatag acaaata                               27

<210> SEQ ID NO 6
<211> LENGTH: 27
<212> TYPE: DNA
<213> ORGANISM: Artificial
<220> FEATURE:
<223> OTHER INFORMATION: chemically synthesized

<400> SEQUENCE: 6
tatttgtcta ttagaccaat tacttgc                               27

<210> SEQ ID NO 7
<211> LENGTH: 27
<212> TYPE: DNA
<213> ORGANISM: Artificial
<220> FEATURE:
<223> OTHER INFORMATION: chemically synthesized

<400> SEQUENCE: 7
gcaagtaatt tgtctaatag acaaata                               27

<210> SEQ ID NO 8
<211> LENGTH: 27
<212> TYPE: DNA

-continued

```
<213> ORGANISM: Artificial
<220> FEATURE:
<223> OTHER INFORMATION: chemically synthesized

<400> SEQUENCE: 8
tatttgtcta ttagacaaat tacttgc                                              27

<210> SEQ ID NO 9
<211> LENGTH: 846
<212> TYPE: PRT
<213> ORGANISM: Clostridium botulinum
<220> FEATURE:
<221> NAME/KEY: MISC_FEATURE
<222> LOCATION: (1)..(846)
<223> OTHER INFORMATION: heavy chain of BoNT/A strain 62A

<400> SEQUENCE: 9

Asn Asp Leu Cys Ile Lys Val Asn Asn Trp Asp Leu Phe Phe Ser Pro
1               5                   10                  15

Ser Glu Asp Asn Phe Thr Asn Asp Leu Asn Lys Gly Glu Glu Ile Thr
            20                  25                  30

Ser Asp Thr Asn Ile Glu Ala Ala Glu Glu Asn Ile Ser Leu Asp Leu
        35                  40                  45

Ile Gln Gln Tyr Tyr Leu Thr Phe Asn Phe Asp Asn Glu Pro Glu Asn
    50                  55                  60

Ile Ser Ile Glu Asn Leu Ser Ser Asp Ile Ile Gly Gln Leu Glu Leu
65                  70                  75                  80

Met Pro Asn Ile Glu Arg Phe Pro Asn Gly Glu Lys Tyr Glu Leu Asp
                85                  90                  95

Lys Tyr Thr Met Phe His Tyr Leu Arg Ala Gln Glu Phe Glu His Gly
            100                 105                 110

Lys Ser Arg Ile Ala Leu Thr Asn Ser Val Asn Glu Ala Leu Leu Asn
        115                 120                 125

Pro Ser Arg Val Tyr Thr Phe Phe Ser Ser Asp Tyr Val Lys Lys Val
    130                 135                 140

Asn Lys Ala Thr Glu Ala Ala Met Phe Leu Gly Trp Val Glu Gln Leu
145                 150                 155                 160

Val Tyr Asp Phe Thr Asp Glu Thr Ser Glu Val Ser Thr Thr Asp Lys
                165                 170                 175

Ile Ala Asp Ile Thr Ile Ile Ile Pro Tyr Ile Gly Pro Ala Leu Asn
            180                 185                 190

Ile Gly Asn Met Leu Tyr Lys Asp Asp Phe Val Gly Ala Leu Ile Phe
        195                 200                 205

Ser Gly Ala Val Ile Leu Leu Glu Phe Ile Pro Glu Ile Ala Ile Pro
    210                 215                 220

Val Leu Gly Thr Phe Ala Leu Val Ser Tyr Ile Ala Asn Lys Val Leu
225                 230                 235                 240

Thr Val Gln Thr Ile Asp Asn Ala Leu Ser Lys Arg Asn Glu Lys Trp
                245                 250                 255

Asp Glu Val Tyr Lys Tyr Ile Val Thr Asn Trp Leu Ala Lys Val Asn
            260                 265                 270

Thr Gln Ile Asp Leu Ile Arg Lys Lys Met Lys Glu Ala Leu Glu Asn
        275                 280                 285

Gln Ala Glu Ala Thr Lys Ala Ile Ile Asn Tyr Gln Tyr Asn Gln Tyr
    290                 295                 300

Thr Glu Glu Glu Lys Asn Asn Ile Asn Phe Asn Ile Asp Asp Leu Ser
305                 310                 315                 320
```

-continued

```
Ser Lys Leu Asn Glu Ser Ile Asn Lys Ala Met Ile Asn Ile Asn Lys
            325                 330                 335

Phe Leu Asn Gln Cys Ser Val Ser Tyr Leu Met Asn Ser Met Ile Pro
            340                 345                 350

Tyr Gly Val Lys Arg Leu Glu Asp Phe Asp Ala Ser Leu Lys Asp Ala
            355                 360                 365

Leu Leu Lys Tyr Ile Tyr Asp Asn Arg Gly Thr Leu Ile Gly Gln Val
            370                 375                 380

Asp Arg Leu Lys Asp Lys Val Asn Asn Thr Leu Ser Thr Asp Ile Pro
385                 390                 395                 400

Phe Gln Leu Ser Lys Tyr Val Asp Asn Gln Arg Leu Leu Ser Thr Phe
            405                 410                 415

Thr Glu Tyr Ile Lys Asn Ile Ile Asn Thr Ser Ile Leu Asn Leu Arg
            420                 425                 430

Tyr Glu Ser Asn His Leu Ile Asp Leu Ser Arg Tyr Ala Ser Lys Ile
            435                 440                 445

Asn Ile Gly Ser Lys Val Asn Phe Asp Pro Ile Asp Lys Asn Gln Ile
            450                 455                 460

Gln Leu Phe Asn Leu Glu Ser Ser Lys Ile Glu Val Ile Leu Lys Asn
465                 470                 475                 480

Ala Ile Val Tyr Asn Ser Met Tyr Glu Asn Phe Ser Thr Ser Phe Trp
            485                 490                 495

Ile Arg Ile Pro Lys Tyr Phe Asn Ser Ile Ser Leu Asn Asn Glu Tyr
            500                 505                 510

Thr Ile Ile Asn Cys Met Glu Asn Asn Ser Gly Trp Lys Val Ser Leu
            515                 520                 525

Asn Tyr Gly Glu Ile Ile Trp Thr Leu Gln Asp Thr Gln Glu Ile Lys
            530                 535                 540

Gln Arg Val Val Phe Lys Tyr Ser Gln Met Ile Asn Ile Ser Asp Tyr
545                 550                 555                 560

Ile Asn Arg Trp Ile Phe Val Thr Ile Thr Asn Asn Arg Leu Asn Asn
            565                 570                 575

Ser Lys Ile Tyr Ile Asn Gly Arg Leu Ile Asp Gln Lys Pro Ile Ser
            580                 585                 590

Asn Leu Gly Asn Ile His Ala Ser Asn Asn Ile Met Phe Lys Leu Asp
            595                 600                 605

Gly Cys Arg Asp Thr His Arg Tyr Ile Trp Ile Lys Tyr Phe Asn Leu
            610                 615                 620

Phe Asp Lys Glu Leu Asn Glu Lys Glu Ile Lys Asp Leu Tyr Asp Asn
625                 630                 635                 640

Gln Ser Asn Ser Gly Ile Leu Lys Asp Phe Trp Gly Asp Tyr Leu Gln
            645                 650                 655

Tyr Asp Lys Pro Tyr Tyr Met Leu Asn Leu Tyr Asp Pro Asn Lys Tyr
            660                 665                 670

Ile Asp Val Asn Asn Val Gly Ile Arg Gly Tyr Met Tyr Leu Lys Gly
            675                 680                 685

Pro Arg Gly Asn Val Met Thr Thr Asn Ile Tyr Leu Asn Ser Ser Leu
            690                 695                 700

Tyr Met Gly Thr Lys Phe Ile Ile Lys Lys Tyr Ala Ser Gly Asn Lys
705                 710                 715                 720

Asp Asn Ile Val Arg Asn Asn Asp Arg Val Tyr Ile Asn Val Val Val
            725                 730                 735

Lys Asn Lys Glu Tyr Arg Leu Ala Thr Asn Ala Ser Gln Ala Gly Val
            740                 745                 750
```

```
Glu Lys Ile Leu Ser Ala Leu Glu Ile Pro Asp Val Gly Asn Leu Ser
        755                 760                 765
Gln Val Val Met Lys Ser Lys Asn Asp Gln Gly Ile Thr Asn Lys
    770                 775                 780
Cys Lys Met Asn Leu Gln Asp Asn Asn Gly Asn Asp Ile Gly Phe Ile
785                 790                 795                 800
Gly Phe His Gln Phe Asn Asn Ile Ala Lys Leu Val Ala Ser Asn Trp
                805                 810                 815
Tyr Asn Arg Gln Ile Glu Arg Ser Ser Arg Thr Leu Gly Cys Ser Trp
            820                 825                 830
Glu Phe Ile Pro Val Asp Asp Gly Trp Gly Glu Arg Pro Leu
        835                 840                 845

<210> SEQ ID NO 10
<211> LENGTH: 846
<212> TYPE: PRT
<213> ORGANISM: Clostridium botulinum

<400> SEQUENCE: 10

Asn Asp Leu Cys Ile Lys Val Asn Asn Trp Asp Leu Phe Phe Ser Pro
1               5                   10                  15
Ser Glu Asp Asn Phe Thr Asn Asp Leu Asn Lys Gly Glu Glu Ile Thr
            20                  25                  30
Ser Asp Thr Asn Ile Glu Ala Ala Glu Asn Ile Ser Leu Asp Leu
        35                  40                  45
Ile Gln Gln Tyr Tyr Leu Thr Phe Asn Phe Asp Asn Glu Pro Glu Asn
    50                  55                  60
Ile Ser Ile Glu Asn Leu Ser Ser Asp Ile Ile Gly Gln Leu Glu Leu
65                  70                  75                  80
Met Pro Asn Ile Glu Arg Phe Pro Asn Gly Glu Lys Tyr Glu Leu Asp
                85                  90                  95
Lys Tyr Thr Met Phe His Tyr Leu Arg Ala Gln Glu Phe Glu His Gly
            100                 105                 110
Lys Ser Arg Ile Ala Leu Thr Asn Ser Val Asn Glu Ala Leu Leu Asn
        115                 120                 125
Pro Ser Arg Val Tyr Thr Phe Phe Ser Ser Asp Tyr Val Lys Lys Val
    130                 135                 140
Asn Lys Ala Thr Glu Ala Ala Met Phe Leu Gly Trp Val Glu Gln Leu
145                 150                 155                 160
Val Tyr Asp Phe Thr Asp Glu Thr Ser Glu Val Ser Thr Thr Asp Lys
                165                 170                 175
Ile Ala Asp Ile Thr Ile Ile Pro Tyr Ile Gly Pro Ala Leu Asn
            180                 185                 190
Ile Gly Asn Met Leu Tyr Lys Asp Asp Phe Val Gly Ala Leu Ile Phe
        195                 200                 205
Ser Gly Ala Val Ile Leu Leu Glu Phe Ile Pro Glu Ile Ala Ile Pro
    210                 215                 220
Val Leu Gly Thr Phe Ala Leu Val Ser Tyr Ile Ala Asn Lys Val Leu
225                 230                 235                 240
Thr Val Gln Thr Ile Asp Asn Ala Leu Ser Lys Arg Asn Glu Lys Trp
                245                 250                 255
Asp Glu Val Tyr Lys Tyr Ile Val Thr Asn Trp Leu Ala Lys Val Asn
            260                 265                 270
Thr Gln Ile Asp Leu Ile Arg Lys Lys Met Lys Glu Ala Leu Glu Asn
        275                 280                 285
```

```
Gln Ala Glu Ala Thr Lys Ala Ile Ile Asn Tyr Gln Tyr Asn Gln Tyr
    290                 295                 300

Thr Glu Glu Glu Lys Asn Asn Ile Asn Phe Asn Ile Asp Asp Leu Ser
305                 310                 315                 320

Ser Lys Leu Asn Glu Ser Ile Asn Lys Ala Met Ile Asn Ile Asn Lys
                325                 330                 335

Phe Leu Asn Gln Cys Ser Val Ser Tyr Leu Met Asn Ser Met Ile Pro
            340                 345                 350

Tyr Gly Val Lys Arg Leu Glu Asp Phe Asp Ala Ser Leu Lys Asp Ala
        355                 360                 365

Leu Leu Lys Tyr Ile Tyr Asp Asn Arg Gly Thr Leu Ile Gly Gln Val
    370                 375                 380

Asp Arg Leu Lys Asp Lys Val Asn Thr Leu Ser Thr Asp Ile Pro
385                 390                 395                 400

Phe Gln Leu Ser Lys Tyr Val Asp Asn Gln Arg Leu Leu Ser Thr Phe
            405                 410                 415

Thr Glu Tyr Ile Lys Asn Ile Ile Asn Thr Ser Ile Leu Asn Leu Arg
                420                 425                 430

Tyr Glu Ser Asn His Leu Ile Asp Leu Ser Arg Tyr Ala Ser Lys Ile
            435                 440                 445

Asn Ile Gly Ser Lys Val Asn Phe Asp Pro Ile Asp Lys Asn Gln Ile
        450                 455                 460

Gln Leu Phe Asn Leu Glu Ser Ser Lys Ile Glu Val Ile Leu Lys Asn
465                 470                 475                 480

Ala Ile Val Tyr Asn Ser Met Tyr Glu Asn Phe Ser Thr Ser Phe Trp
            485                 490                 495

Ile Arg Ile Pro Lys Tyr Phe Asn Ser Ile Ser Leu Asn Asn Glu Tyr
                500                 505                 510

Thr Ile Ile Asn Cys Met Glu Asn Asn Ser Gly Trp Lys Val Ser Leu
            515                 520                 525

Asn Tyr Gly Glu Ile Ile Trp Thr Leu Gln Asp Thr Gln Glu Ile Lys
    530                 535                 540

Gln Arg Val Val Phe Lys Tyr Ser Gln Met Ile Asn Ile Ser Asp Tyr
545                 550                 555                 560

Ile Asn Arg Trp Ile Phe Val Thr Ile Thr Asn Asn Arg Leu Asn Asn
            565                 570                 575

Ser Lys Ile Tyr Ile Asn Gly Arg Leu Ile Asp Gln Lys Pro Ile Ser
            580                 585                 590

Asn Leu Gly Asn Ile His Ala Ser Asn Asn Ile Met Phe Lys Leu Asp
            595                 600                 605

Gly Cys Arg Asp Thr His Arg Tyr Ile Trp Ile Lys Tyr Phe Asn Leu
    610                 615                 620

Phe Asp Lys Glu Leu Asn Glu Lys Glu Ile Lys Asp Leu Tyr Asp Asn
625                 630                 635                 640

Gln Ser Asn Ser Gly Ile Leu Lys Asp Phe Trp Gly Asp Tyr Leu Gln
            645                 650                 655

Tyr Asp Lys Pro Tyr Tyr Met Leu Asn Leu Tyr Asp Pro Asn Lys Tyr
            660                 665                 670

Ile Asp Val Asn Asn Val Gly Ile Arg Gly Tyr Met Tyr Leu Lys Gly
            675                 680                 685

Pro Arg Gly Asn Val Met Thr Thr Asn Ile Tyr Leu Asn Ser Ser Leu
    690                 695                 700

Tyr Met Gly Thr Lys Phe Ile Ile Lys Lys Tyr Ala Ser Gly Asn Lys
```

```
                705                 710                 715                 720
Asp Asn Ile Val Arg Asn Asn Asp Arg Val Tyr Ile Asn Val Val Val
                    725                 730                 735

Lys Asn Lys Glu Tyr Arg Leu Ala Thr Asn Ala Ser Gln Ala Gly Val
                    740                 745                 750

Glu Lys Ile Leu Ser Ala Leu Glu Ile Pro Asp Val Gly Asn Leu Ser
                    755                 760                 765

Gln Val Val Met Lys Ser Lys Asn Asp Gln Gly Ile Thr Asn Lys
    770                 775                 780

Cys Lys Met Asn Leu Gln Asp Asn Asn Gly Asn Asp Ile Gly Phe Ile
785                 790                 795                 800

Gly Phe His Gln Phe Asn Asn Ile Ala Lys Leu Val Ala Ser Asn Trp
                    805                 810                 815

Tyr Asn Arg Gln Ile Glu Arg Ser Ser Arg Thr Leu Gly Cys Ser Trp
                    820                 825                 830

Glu Phe Ile Pro Val Asp Asp Gly Trp Gly Glu Arg Pro Leu
                    835                 840                 845

<210> SEQ ID NO 11
<211> LENGTH: 846
<212> TYPE: PRT
<213> ORGANISM: Clostridium botulinum

<400> SEQUENCE: 11

Asn Glu Leu Cys Ile Lys Val Asn Asn Trp Asp Leu Phe Phe Ser Pro
1               5                   10                  15

Ser Glu Asp Asn Phe Thr Asn Asp Leu Asp Lys Val Glu Glu Ile Thr
                20                  25                  30

Ser Asp Thr Asn Ile Glu Ala Ala Glu Asn Ile Ser Leu Asp Leu
            35                  40                  45

Ile Gln Gln Tyr Tyr Leu Asn Phe Asn Phe Asp Asn Glu Pro Glu Asn
    50                  55                  60

Thr Ser Ile Glu Asn Leu Ser Ser Asp Ile Ile Gly Gln Leu Glu Pro
65                  70                  75                  80

Met Pro Asn Ile Glu Arg Phe Pro Asn Gly Lys Lys Tyr Glu Leu Asn
                85                  90                  95

Lys Tyr Thr Met Phe His Tyr Leu Arg Ala Gln Glu Phe Lys His Ser
                100                 105                 110

Asn Ser Arg Ile Ile Leu Thr Asn Ser Ala Lys Glu Ala Leu Leu Lys
            115                 120                 125

Pro Asn Ile Val Tyr Thr Phe Phe Ser Ser Lys Tyr Ile Lys Ala Ile
    130                 135                 140

Asn Lys Ala Val Glu Ala Val Thr Phe Val Asn Trp Ile Glu Asn Leu
145                 150                 155                 160

Val Tyr Asp Phe Thr Asp Glu Thr Asn Glu Val Ser Thr Met Asp Lys
                165                 170                 175

Ile Ala Asp Ile Thr Ile Val Ile Pro Tyr Ile Gly Pro Ala Leu Asn
                180                 185                 190

Ile Gly Asn Met Ile Tyr Lys Gly Glu Phe Val Glu Ala Ile Ile Phe
            195                 200                 205

Ser Gly Ala Val Ile Leu Leu Glu Ile Val Pro Glu Ile Ala Leu Pro
    210                 215                 220

Val Leu Gly Thr Phe Ala Leu Val Ser Tyr Val Ser Asn Lys Val Leu
225                 230                 235                 240

Thr Val Gln Thr Ile Asp Asn Ala Leu Ser Lys Arg Asn Glu Lys Trp
```

-continued

```
                245                 250                 255
Asp Glu Val Tyr Lys Tyr Ile Val Thr Asn Trp Leu Ala Ile Val Asn
                260                 265                 270

Thr Gln Ile Asn Leu Ile Arg Glu Lys Met Lys Lys Ala Leu Glu Asn
            275                 280                 285

Gln Ala Glu Ala Thr Lys Ala Ile Ile Asn Tyr Gln Tyr Asn Gln Tyr
        290                 295                 300

Thr Glu Glu Lys Asn Asn Ile Asn Phe Asn Ile Asp Asp Leu Ser
305                 310                 315                 320

Ser Lys Leu Asn Glu Ser Ile Asn Ser Ala Met Ile Asn Ile Asn Lys
                325                 330                 335

Phe Leu Asp Gln Cys Ser Val Ser Tyr Leu Met Asn Ser Met Ile Pro
            340                 345                 350

Tyr Ala Val Lys Arg Leu Lys Asp Phe Asp Ala Ser Val Arg Asp Val
        355                 360                 365

Leu Leu Lys Tyr Ile Tyr Asp Asn Arg Gly Thr Leu Ile Gly Gln Val
    370                 375                 380

Asn Arg Leu Lys Asp Lys Val Asn Asn Thr Leu Ser Ala Asp Ile Pro
385                 390                 395                 400

Phe Gln Leu Ser Lys Tyr Val Asp Asn Lys Lys Leu Leu Ser Thr Phe
                405                 410                 415

Thr Glu Tyr Ile Lys Asn Ile Thr Asn Ala Ser Ile Leu Ser Ile Val
            420                 425                 430

Tyr Lys Asp Asp Asp Leu Ile Asp Leu Ser Arg Tyr Gly Ala Glu Ile
        435                 440                 445

Tyr Asn Gly Asp Lys Val Tyr Tyr Asn Ser Ile Asp Lys Asn Gln Ile
    450                 455                 460

Arg Leu Ile Asn Leu Glu Ser Ser Thr Ile Glu Val Ile Leu Lys Lys
465                 470                 475                 480

Ala Ile Val Tyr Asn Ser Met Tyr Glu Asn Phe Ser Thr Ser Phe Trp
                485                 490                 495

Ile Arg Ile Pro Lys Tyr Phe Asn Ser Ile Ser Leu Asn Asn Glu Tyr
            500                 505                 510

Thr Ile Ile Asn Cys Met Glu Asn Asn Ser Gly Trp Lys Val Ser Leu
        515                 520                 525

Asn Tyr Gly Glu Ile Ile Trp Thr Phe Gln Asp Thr Gln Glu Ile Lys
    530                 535                 540

Gln Arg Val Val Phe Lys Tyr Ser Gln Met Ile Asn Ile Ser Asp Tyr
545                 550                 555                 560

Ile Asn Arg Trp Ile Phe Val Thr Ile Thr Asn Asn Arg Ile Thr Lys
                565                 570                 575

Ser Lys Ile Tyr Ile Asn Gly Arg Leu Ile Asp Gln Lys Pro Ile Ser
            580                 585                 590

Asn Leu Gly Asn Ile His Ala Ser Asn Lys Ile Met Phe Lys Leu Asp
        595                 600                 605

Gly Cys Arg Asp Pro His Arg Tyr Ile Val Ile Lys Tyr Phe Asn Leu
    610                 615                 620

Phe Asp Lys Glu Leu Ser Glu Lys Glu Ile Lys Asp Leu Tyr Asp Asn
625                 630                 635                 640

Gln Ser Asn Ser Gly Ile Leu Lys Asp Phe Trp Gly Asp Tyr Leu Gln
                645                 650                 655

Tyr Asp Lys Ser Tyr Tyr Met Leu Asn Leu Tyr Asp Pro Asn Lys Tyr
            660                 665                 670
```

```
Val Asp Val Asn Asn Val Gly Ile Arg Gly Tyr Met Tyr Leu Lys Gly
        675                 680                 685

Pro Arg Asp Asn Val Met Thr Thr Asn Ile Tyr Leu Asn Ser Ser Leu
    690                 695                 700

Tyr Met Gly Thr Lys Phe Ile Ile Lys Lys Tyr Ala Ser Gly Asn Lys
705                 710                 715                 720

Asp Asn Ile Val Arg Asn Asn Asp Arg Val Tyr Ile Asn Val Val Val
                725                 730                 735

Lys Asn Lys Glu Tyr Arg Leu Ala Thr Asn Ala Ser Gln Ala Gly Val
                740                 745                 750

Glu Lys Ile Leu Ser Ala Leu Glu Ile Pro Asp Val Gly Asn Leu Ser
                755                 760                 765

Gln Val Val Met Lys Ser Lys Asn Asp Gln Gly Ile Thr Asn Lys
    770                 775                 780

Cys Lys Met Asn Leu Gln Asp Asn Gly Asn Asp Ile Gly Phe Ile
785                 790                 795                 800

Gly Phe His Gln Phe Asn Asn Ile Ala Lys Leu Val Ala Ser Asn Trp
                805                 810                 815

Tyr Asn Arg Gln Ile Glu Arg Ser Ser Arg Thr Leu Gly Cys Ser Trp
                820                 825                 830

Glu Phe Ile Pro Val Asp Asp Gly Trp Arg Glu Arg Pro Leu
                835                 840                 845

<210> SEQ ID NO 12
<211> LENGTH: 846
<212> TYPE: PRT
<213> ORGANISM: Clostridium botulinum

<400> SEQUENCE: 12

Asn Asp Leu Cys Ile Lys Val Asn Asn Trp Asp Leu Phe Phe Ser Pro
1               5                   10                  15

Ser Glu Asp Asn Phe Thr Asn Asp Leu Asp Lys Val Glu Glu Ile Thr
                20                  25                  30

Ala Asp Thr Asn Ile Glu Ala Ala Glu Glu Asn Ile Ser Leu Asp Leu
            35                  40                  45

Ile Gln Gln Tyr Tyr Leu Thr Phe Asp Phe Asn Glu Pro Glu Asn
    50                  55                  60

Ile Ser Ile Glu Asn Leu Ser Ser Asp Ile Ile Gly Gln Leu Glu Pro
65                  70                  75                  80

Met Pro Asn Ile Glu Arg Phe Pro Asn Gly Lys Lys Tyr Glu Leu Asp
                85                  90                  95

Lys Tyr Thr Met Phe His Tyr Leu Arg Ala Gln Glu Phe Glu His Gly
            100                 105                 110

Asp Ser Arg Ile Ile Leu Thr Asn Ser Ala Glu Glu Ala Leu Leu Lys
        115                 120                 125

Pro Asn Val Ala Tyr Thr Phe Phe Ser Ser Lys Tyr Val Lys Lys Ile
    130                 135                 140

Asn Lys Ala Val Glu Ala Phe Met Phe Leu Asn Trp Ala Glu Glu Leu
145                 150                 155                 160

Val Tyr Asp Phe Thr Asp Glu Thr Asn Glu Val Thr Thr Met Asp Lys
                165                 170                 175

Ile Ala Asp Ile Thr Ile Ile Val Pro Tyr Ile Gly Pro Ala Leu Asn
            180                 185                 190

Ile Gly Asn Met Leu Ser Lys Gly Glu Phe Val Glu Ala Ile Ile Phe
        195                 200                 205
```

-continued

```
Thr Gly Val Val Ala Met Leu Glu Phe Ile Pro Glu Tyr Ala Leu Pro
            210                 215                 220

Val Phe Gly Thr Phe Ala Ile Val Ser Tyr Ile Ala Asn Lys Val Leu
225                 230                 235                 240

Thr Val Gln Thr Ile Asn Asn Ala Leu Ser Lys Arg Asn Glu Lys Trp
                245                 250                 255

Asp Glu Val Tyr Lys Tyr Thr Val Thr Asn Trp Leu Ala Lys Val Asn
            260                 265                 270

Thr Gln Ile Asp Leu Ile Arg Glu Lys Met Lys Ala Leu Glu Asn
            275                 280                 285

Gln Ala Glu Ala Thr Lys Ala Ile Ile Asn Tyr Gln Tyr Asn Gln Tyr
290                 295                 300

Thr Glu Glu Lys Asn Asn Ile Asn Phe Asn Ile Asp Asp Leu Ser
305                 310                 315                 320

Ser Lys Leu Asn Glu Ser Ile Asn Ser Ala Met Ile Asn Ile Asn Lys
                325                 330                 335

Phe Leu Asp Gln Cys Ser Val Ser Tyr Leu Met Asn Ser Met Ile Pro
            340                 345                 350

Tyr Ala Val Lys Arg Leu Lys Asp Phe Asp Ala Ser Val Arg Asp Val
            355                 360                 365

Leu Leu Lys Tyr Ile Tyr Asp Asn Arg Gly Thr Leu Val Leu Gln Val
370                 375                 380

Asp Arg Leu Lys Asp Glu Val Asn Asn Thr Leu Ser Ala Asp Ile Pro
385                 390                 395                 400

Phe Gln Leu Ser Lys Tyr Val Asp Asn Lys Leu Leu Ser Thr Phe
            405                 410                 415

Thr Glu Tyr Ile Lys Asn Ile Val Asn Thr Ser Ile Leu Ser Ile Val
            420                 425                 430

Tyr Lys Lys Asp Asp Leu Ile Asp Leu Ser Arg Tyr Gly Ala Lys Ile
            435                 440                 445

Asn Ile Gly Asp Arg Val Tyr Tyr Asp Ser Ile Asp Lys Asn Gln Ile
            450                 455                 460

Lys Leu Ile Asn Leu Glu Ser Ser Thr Ile Glu Val Ile Leu Lys Asn
465                 470                 475                 480

Ala Ile Val Tyr Asn Ser Met Tyr Glu Asn Phe Ser Thr Ser Phe Trp
                485                 490                 495

Ile Lys Ile Pro Lys Tyr Phe Ser Lys Ile Asn Leu Asn Asn Glu Tyr
            500                 505                 510

Thr Ile Ile Asn Cys Ile Glu Asn Asn Ser Gly Trp Lys Val Ser Leu
            515                 520                 525

Asn Tyr Gly Glu Ile Ile Trp Thr Leu Gln Asp Asn Lys Gln Asn Ile
530                 535                 540

Gln Arg Val Val Phe Lys Tyr Ser Gln Met Val Asn Ile Ser Asp Tyr
545                 550                 555                 560

Ile Asn Arg Trp Ile Phe Val Thr Ile Thr Asn Asn Arg Leu Thr Lys
                565                 570                 575

Ser Lys Ile Tyr Ile Asn Gly Arg Leu Ile Asp Gln Lys Pro Ile Ser
            580                 585                 590

Asn Leu Gly Asn Ile His Ala Ser Asn Lys Ile Met Phe Lys Leu Asp
            595                 600                 605

Gly Cys Arg Asp Pro Arg Tyr Ile Met Ile Lys Tyr Phe Asn Leu
610                 615                 620

Phe Asp Lys Glu Leu Asn Glu Lys Glu Ile Lys Asp Leu Tyr Asp Ser
625                 630                 635                 640
```

Gln Ser Asn Ser Gly Ile Leu Lys Asp Phe Trp Gly Asn Tyr Leu Gln
                645                 650                 655

Tyr Asp Lys Pro Tyr Tyr Met Leu Asn Leu Phe Asp Pro Asn Lys Tyr
            660                 665                 670

Val Asp Val Asn Asn Ile Gly Ile Arg Gly Tyr Met Tyr Leu Lys Gly
                675                 680                 685

Pro Arg Gly Ser Val Val Thr Thr Asn Ile Tyr Leu Asn Ser Thr Leu
        690                 695                 700

Tyr Glu Gly Thr Lys Phe Ile Ile Lys Lys Tyr Ala Ser Gly Asn Glu
705                 710                 715                 720

Asp Asn Ile Val Arg Asn Asp Arg Val Tyr Ile Asn Val Val Val
                725                 730                 735

Lys Asn Lys Glu Tyr Arg Leu Ala Thr Asn Ala Ser Gln Ala Gly Val
            740                 745                 750

Glu Lys Ile Leu Ser Ala Leu Glu Ile Pro Asp Val Gly Asn Leu Ser
        755                 760                 765

Gln Val Val Met Lys Ser Lys Asp Asp Gln Gly Ile Arg Asn Lys
    770                 775                 780

Cys Lys Met Asn Leu Gln Asp Asn Asn Gly Asn Asp Ile Gly Leu Ile
785                 790                 795                 800

Gly Phe His Gln Phe Asn Asn Ile Ala Lys Leu Val Ala Ser Asn Trp
                805                 810                 815

Tyr Asn Arg Gln Val Gly Lys Ala Ser Arg Thr Phe Gly Cys Ser Trp
            820                 825                 830

Glu Phe Ile Pro Val Asp Asp Gly Trp Gly Glu Ser Ser Leu
        835                 840                 845

<210> SEQ ID NO 13
<211> LENGTH: 1299
<212> TYPE: DNA
<213> ORGANISM: Clostridium botulinum

<400> SEQUENCE: 13
acatttactg aatatattaa gaatattatt aatacttcta tattgaattt aagatatgaa      60
agtaatcatt taatagactt atctaggtat gcatcaaaaa taaatattgg tagtaaagta     120
aattttgatc caatagataa aaatcaaatt caattattta atttagaaag tagtaaaatt     180
gaggtaattt taaaaaatgc tattgtatat aatagtatgt atgaaaattt tagtactagc     240
ttttggataa gaattcctaa gtattttaac agtataagtc taaataatga atatacaata     300
ataaattgta tggaaaataa ttcaggatgg aaagtatcac ttaattatgg tgaaataatc     360
tggactttac aggatactca ggaaataaaa caaagagtag ttttttaaata cagtcaaatg     420 attaatatat cagattatat aaacagatgg attttgtaa ctatcactaa taatagatta     480
aataactcta aaatttatat aaatggaaga ttaatagatc aaaaaccaat ttcaaattta     540
ggtaatattc atgctagtaa taatataatg tttaaattag atggttgtag agatacacat     600
agatatattt ggataaaata ttttaatctt tttgataagg aattaaatga aaagaaaatc     660
aaagatttat atgataatca atcaaattca ggtattttaa aagacttttg gggtgattat     720
ttacaatatg ataaaccata ctatatgtta aattatatg atccaaataa atatgtcgat     780
gtaaataatg taggtattag aggttatatg tatcttaaag ggcctagagg tagcgtaatg     840
actacaaaca tttatttaaa ttcaagtttg tatggggga caaaatttat tataaaaaaa     900
tatgcttctg gaaataaaga taatattgtt agaaataatg atcgtgtata tattaatgta     960

-continued

```
gtagttaaaa ataaagaata taggttagct actaatgcat cacaggcagg cgtagaaaaa    1020
atactaagtg cattagaaat acctgatgta ggaaatctaa gtcaagtagt agtaatgaag    1080
tcaaaaaatg atcaaggaat aacaaataaa tgcaaaatga atttacaaga taataatggg    1140
aatgatatag gctttatagg atttcatcag tttaataata tagctaaact agtagcaagt    1200
aatttgtcta atagacaaat agaaagatct agtaggactt tgggttgctc atgggaattt    1260
attcctgtag atgatggatg gggagaaagg ccactgtaa                          1299
```

```
<210> SEQ ID NO 14
<211> LENGTH: 432
<212> TYPE: PRT
<213> ORGANISM: Clostridium botulinum
<220> FEATURE:
<221> NAME/KEY: MISC_FEATURE
<222> LOCATION: (1)..(436)
<223> OTHER INFORMATION: dimutant HC50

<400> SEQUENCE: 14

Thr Phe Thr Glu Tyr Ile Lys Asn Ile Ile Asn Thr Ser Ile Leu Asn
1               5                   10                  15

Leu Arg Tyr Glu Ser Asn His Leu Ile Asp Leu Ser Arg Tyr Ala Ser
            20                  25                  30

Lys Ile Asn Ile Gly Ser Lys Val Asn Phe Asp Pro Ile Asp Lys Asn
        35                  40                  45

Gln Ile Gln Leu Phe Asn Leu Glu Ser Ser Lys Ile Glu Val Ile Leu
    50                  55                  60

Lys Asn Ala Ile Val Tyr Asn Ser Met Tyr Glu Asn Phe Ser Thr Ser
65                  70                  75                  80

Phe Trp Ile Arg Ile Pro Lys Tyr Phe Asn Ser Ile Ser Leu Asn Asn
                85                  90                  95

Glu Tyr Thr Ile Ile Asn Cys Met Glu Asn Asn Ser Gly Trp Lys Val
            100                 105                 110

Ser Leu Asn Tyr Gly Glu Ile Ile Trp Thr Leu Gln Asp Thr Gln Glu
        115                 120                 125

Ile Lys Gln Arg Val Val Phe Lys Tyr Ser Gln Met Ile Asn Ile Ser
    130                 135                 140

Asp Tyr Ile Asn Arg Trp Ile Phe Val Thr Ile Thr Asn Asn Arg Leu
145                 150                 155                 160

Asn Asn Ser Lys Ile Tyr Ile Asn Gly Arg Leu Ile Asp Gln Lys Pro
                165                 170                 175

Ile Ser Asn Leu Gly Asn Ile His Ala Ser Asn Asn Ile Met Phe Lys
            180                 185                 190

Leu Asp Gly Cys Arg Asp Thr His Arg Tyr Ile Trp Ile Lys Tyr Phe
        195                 200                 205

Asn Leu Phe Asp Lys Glu Leu Asn Glu Lys Glu Ile Lys Asp Leu Tyr
    210                 215                 220

Asp Asn Gln Ser Asn Ser Gly Ile Leu Lys Asp Phe Trp Gly Asp Tyr
225                 230                 235                 240

Leu Gln Tyr Asp Lys Pro Tyr Tyr Met Leu Asn Leu Tyr Asp Pro Asn
                245                 250                 255

Lys Tyr Val Asp Val Asn Asn Val Gly Ile Arg Gly Tyr Met Tyr Leu
            260                 265                 270

Lys Gly Pro Arg Gly Ser Val Met Thr Thr Asn Ile Tyr Leu Asn Ser
        275                 280                 285

Ser Leu Tyr Arg Gly Thr Lys Phe Ile Ile Lys Lys Tyr Ala Ser Gly
    290                 295                 300
```

```
Asn Lys Asp Asn Ile Val Arg Asn Asp Arg Val Tyr Ile Asn Val
305                 310                 315                 320

Val Val Lys Asn Lys Glu Tyr Arg Leu Ala Thr Asn Ala Ser Gln Ala
            325                 330                 335

Gly Val Glu Lys Ile Leu Ser Ala Leu Glu Ile Pro Asp Val Gly Asn
        340                 345                 350

Leu Ser Gln Val Val Met Lys Ser Lys Asn Asp Gln Gly Ile Thr
    355                 360                 365

Asn Lys Cys Lys Met Asn Leu Gln Asp Asn Asn Gly Asn Asp Ile Gly
    370                 375                 380

Phe Ile Gly Phe His Gln Phe Asn Asn Ile Ala Lys Leu Val Ala Ser
385                 390                 395                 400

Asn Leu Ser Asn Arg Gln Ile Glu Arg Ser Arg Thr Leu Gly Cys
            405                 410                 415

Ser Trp Glu Phe Ile Pro Val Asp Asp Gly Trp Gly Glu Arg Pro Leu
            420                 425                 430

<210> SEQ ID NO 15
<211> LENGTH: 2475
<212> TYPE: DNA
<213> ORGANISM: Clostridium botulinum

<400> SEQUENCE: 15
aatgatctaa ataaaggaga agaaattaca tctgatacta atatagaagc agcagaagaa    60
aatattagtt tagatttaat acaacaatat tatttaacct ttaattttga taatgaacct   120
gaaaatattt caatagaaaa tctttcaagt gacattatag gccaattaga acttatgcct   180
aatatagaaa gatttcctaa tggaaaaaag tatgagttag ataaatatac tatgttccat   240
tatcttcgtg ctcaagaatt tgaacatggt aaatctagga ttgctttaac aaattctgtt   300
aacgaagcat tattaaatcc tagtcgtgtt tatacatttt tttcttcaga ctatgtaaag   360
aaagttaata aagctacgga ggcagctatg tttttaggct gggtagaaca attagtatat   420
gattttaccg atgaaactag cgaagtaagt actacggata aaattgcgga tataactata   480
attattccat atataggacc tgctttaaat ataggtaata tgttatataa agatgatttt   540
gtaggtgctt taatattttc aggagctgtt attctgttag aatttatacc agagattgca   600
atacctgtat taggtacttt tgcacttgta tcatatattg cgaataaggt tctaaccgtt   660
caaacaatag ataatgcttt aagtaaaaga atgaaaaat gggatgaggt ctataaatat   720
atagtaacaa attggttagc aaaggttaat acacagattg atctaataag aaaaaaaatg   780
aaagaagctt tagaaaatca agcagaagca acaaaggcta taataaacta tcagtataat   840
caatatactg aggaagagaa aaataatatt aattttaata ttgatgattt aagttcgaaa   900
cttaatgagt ctataaataa agctatgatt aatataaata aattttttga atcaatgctct   960 gtttcatatt taatgaattc tatgatccct tatggtgtta acggttaga agattttgat   1020 gctagtctta agatgcatt attaaagtat atatatgata atagaggaac tttaattggt   1080
caagtagata gattaaaaga taagttaat aatacacttg gtacagatat accttttcag   1140
ctttccaaat acgtagataa tcaaagatta ttatctacat ttactgaata tattaagaat   1200
attattaata cttctatatt gaatttaaga tatgaaagta tcatttaat agacttatct   1260 aggtatgcat caaaatataaa tattggtagt aaagtaaatt ttgatccaat agataaaaat   1320
caaattcaat tatttaatttt agaaagtagt aaaattgagg taattttaaa aaatgctatt   1380
gtatataata gtatgtatga aaatttagt actagctttt ggataagaat tcctaagtat   1440
```

```
tttaacagta taagtctaaa taatgaatat acaataataa attgtatgga aaataattca   1500
ggatggaaag tatcacttaa ttatggtgaa ataatctgga ctttacagga tactcaggaa   1560
ataaaacaaa gagtagtttt taaatacagt caaatgatta atatatcaga ttatataaac   1620
agatggattt ttgtaactat cactaataat agattaaata actctaaaat ttatataaat   1680
ggaagattaa tagatcaaaa accaatttca aatttaggta atattcatgc tagtaataat   1740
ataatgttta aattagatgg ttgtagagat acacatagat atatttggat aaaatatttt   1800
aatctttttg ataaggaatt aaatgaaaaa gaaatcaaag atttatatga taatcaatca   1860
aattcaggta ttttaaaaga cttttggggt gattatttac aatatgataa accatactat   1920
atgttaaatt tatatgatcc aaataaatat gtcgatgtaa ataatgtagg tattagaggt   1980
tatatgtatc ttaaagggcc tagaggtagc gtaatgacta caaacattta tttaaattca   2040
agtttgtata gggggacaaa atttattata aaaaaatatg cttctggaaa taaagataat   2100
attgttagaa ataatgatcg tgtatatatt aatgtagtag ttaaaaataa agaatatagg   2160
ttagctacta atgcatcaca ggcaggcgta gaaaaaatac taagtgcatt agaaatacct   2220
gatgtaggaa atctaagtca gtagtagta atgaagtcaa aaaatgatca aggaataaca   2280
aataaatgca aaatgaattt acaagataat aatgggaatg atataggctt tataggattt   2340
catcagttta ataatatagc taaactagta gcaagtaatt ggtataatag acaaatagaa   2400
agatctagta ggactttggg ttgctcatgg gaatttattc ctgtagatga tggatgggga   2460
gaaaggccac tgtaa                                                    2475

<210> SEQ ID NO 16
<211> LENGTH: 2475
<212> TYPE: DNA
<213> ORGANISM: Clostridium botulinum

<400> SEQUENCE: 16
aatgatctaa ataaaggaga agaaattaca tctgatacta atatagaagc agcagaagaa     60
aatattagtt tagatttaat acaacaatat tatttaacct ttaattttga taatgaacct    120
gaaaatattt caatagaaaa tctttcaagt gacattatag gccaattaga acttatgcct    180
aatatagaaa gatttcctaa tggagaaaag tatgagttag ataaatatac tatgttccat    240
tatcttcgtg ctcaagaatt tgaacatggt aaatctagga ttgctttaac aaattctgtt    300
aacgaagcat tattaaatcc tagtcgtgtt tatacatttt tttcttcaga ctatgtaaag    360
aaagttaata agctacggaa ggcagctatg ttttaggct gggtagaaca attagtatat    420
gattttaccg atgaaactag cgaagtaagt actacggata aaattgcgga tataactata    480
attattccat atataggacc tgcttaaat ataggtaata tgttatataa agatgatttt    540
gtaggtgctt taatatttc aggagctgtt attctgttag aatttatacc agagattgca    600
atacctgtat taggtacttt tgcacttgta tcatatattg cgaataaggt tctaaccgtt    660
caaacaatag ataatgcttt aagtaaaaga atgaaaaat gggatgaggt ctataaaat    720 atagtaacaa attggttagc aaaggttaat acacagattg atctaataag aaaaaaatg    780 aaagaagctt tagaaaatca agcagaagca acaaaggcta taataaacta tcagtataat    840
caatatactg aggaagagaa aaataatatt aatttaata ttgatgattt aagttcgaaa    900
cttaatgagt ctataaataa agctatgatt aatataaata aattttgaa tcaatgctct    960 gtttcatatt taatgaattc tatgatccct tatggtgtta acggttaga agattttgat   1020 gctagtctta aagatgcatt attaaagtat atatatgata atagaggaac tttaattggt   1080
```

```
caagtagata gattaaaaga taaagttaat aatacactta gtacagatat acctttttcag    1140 ctttccaaat acgtagataa tcaaagatta ttatctacat ttactgaata tattaagaat    1200
attattaata cttctatatt gaatttaaga tatgaaagta atcatttaat agacttatct    1260
aggtatgcat caaaaataaa tattggtagt aaagtaaatt ttgatccaat agataaaaat    1320
caaattcaat tatttaattt agaaagtagt aaaattgagg taattttaaa aaatgctatt    1380
gtatataata gtatgtatga aaattttagt actagctttt ggataagaat tcctaagtat    1440
tttaacagta taagtctaaa taatgaatat acaataataa attgtatgga aaataattca    1500
ggatggaaag tatcacttaa ttatggtgaa ataatctgga ctttacagga tactcaggaa    1560
ataaaacaaa gagtagtttt taaatacagt caaatgatta atatatcaga ttatataaac    1620
agatggattt ttgtaactat cactaataat agattaaata actctaaaat ttatataaat    1680
ggaagattaa tagatcaaaa accaatttca aatttaggta atattcatgc tagtaataat    1740
ataatgttta aattagatgg ttgtagagat acacatagat atatttggat aaaatatttt    1800 aatcttttg ataaggaatt aaatgaaaaa gaaatcaaag atttatatga taatcaatca    1860
aattcaggta ttttaaaaga cttttggggt gattatttac aatatgataa accatactat    1920
atgttaaatt tatatgatcc aaataaaatat atcgatgtaa ataatgtagg tattagaggt    1980
tatatgtatc ttaaagggcc tagaggtaac gtaatgacta caaacattta tttaaattca    2040
agtttgtata tggggacaaa atttattata aaaaaatatg cttctggaaa taaagataat    2100
attgttagaa ataatgatcg tgtatatatt aatgtagtag ttaaaaataa agaatatagg    2160
ttagctacta atgcatcaca ggcaggcgta gaaaaaatac taagtgcatt agaaatacct    2220
gatgtaggaa atctaagtca agtagtagta atgaagtcaa aaaatgatca aggaataaca    2280
aataaatgca aaatgaattt acaagataat aatgggaatg atataggctt tataggatttt   2340 catcagttta ataatatagc taaactagta gcaagtaatt ggtataatag acaaatagaa    2400
agatctagta ggactttggg ttgctcatgg gaatttattc ctgtagatga tggatgggga    2460
gaaaggccac tgtaa                                                     2475
```

<210> SEQ ID NO 17  
<211> LENGTH: 2475  
<212> TYPE: DNA  
<213> ORGANISM: Clostridium botulinum

<400> SEQUENCE: 17

```
aatgatctag ataaggtaga agaaattaca tctgatacta atatagaagc agcagaagaa     60
aatattagtt tagatttaat acaacaatat tatttaaact ttaattttga taatgaacct    120
gaaaatactt caatagaaaa tctttcaagt gatattatag gacaattaga acctatgcct    180
aatatagaaa gatttcccaa tggaaaaaag tatgagttaa ataaatatac tatgttccat    240
taccttcgtg ctcaagaatt caaacatagt aattctagga ttattttaac aaaattctgcc   300 aaagaggcct tattaaagcc taatattgtt tatacatttt tttcttcaaa atatatataaa   360 gcaattaata aagctgtaga ggcagttacg tttgttaatt ggatagaaaa cttagtgtat    420 gatttttactg atgaaactaa tgaggtaagt actatggata aaattgctga tataactata    480
gttattccat atataggacc tgctttaaat ataggtaata tgatatataa aggagagttt    540
gtagaagcta taatattttc gggagctgtt attctattag aaattgtacc agagattgcg    600
ctacctgtat taggtacttt tgcacttgta tcatatgttt cgaataaggt tctaaccgtt    660
caaacaatag ataatgcttt aagtaaaaga atgaaaaat gggatgaggt ctataaatat    720
```

| | |
|---|---|
| atagtaacaa attggttggc aatagttaat acacagatca atctaataag agaaaaaatg | 780 |
| aaaaaagctt tagaaaatca ggcagaagca acgaaggcta ataaaacta tcagtataat | 840 |
| caatatactg aggaagagaa aaataatatt aattttaata ttgatgattt aagttcgaaa | 900 |
| cttaatgagt ctataaatag cgctatgatt aacataaata aattttttgga tcaatgctct | 960 |
| gtttcatatt taatgaattc tatgatacct tatgctgtta aacggttaaa agattttgat | 1020 |
| gctagtgtta gagacgtatt attaaagtat atatatgata atagaggaac tttaattggt | 1080 |
| caagtaaata gattaaaaga taaagttaat aatacactta gtgcagatat accttttcag | 1140 |
| ctttctaaat acgtagataa taaaaaatta ttatctacat ttactgaata tattaagaat | 1200 |
| attactaatg cctctatatt gagcatagta tataaagatg atgatttaat agatttatct | 1260 |
| aggtatggag cagaaatata taatggtgat aaagtatatt ataattcaat agataaaaat | 1320 |
| caaattcgat taattaattt agaaagtagt acaattgagg taattttaaa aaaggctatt | 1380 |
| gtatataata gtatgtatga aaattttagt actagctttt ggataagaat tcctaagtat | 1440 |
| tttaacagta taagtctaaa taatgaatat acaataataa attgtatgga aaataattca | 1500 |
| ggatggaaag tatcacttaa ttatggtgaa ataatctgga ctttccagga tactcaggaa | 1560 |
| ataaaacaaa gagtagtttt taaatacagt caaatgatta atatatcaga ttatataaac | 1620 |
| agatggattt ttgtaactat cactaataat agaataacta atctaaaat ttatataaat | 1680 |
| ggaagattaa tagatcaaaa accaatttca aatttaggta atattcatgc tagtaataag | 1740 |
| ataatgttta aattagatgg ctgtagagat ccacatagat acatcgtgat aaaatatttc | 1800 |
| aatcttttcg ataaagaatt aagtgaaaaa gagatcaaag atttatatga taatcaatca | 1860 |
| aattcaggta ttttaaaaga cttttggggt gattatttac aatatgataa atcatactat | 1920 |
| atgttaaatt tatatgatcc aaataaatat gtcgatgtaa ataatgtagg tattagaggt | 1980 |
| tatatgtatc ttaaagggcc tagagataac gtaatgacta caaacattta tttaaattca | 2040 |
| agtttgtata tggggacaaa atttattata aaaaaatatg cttctggaaa taaagataat | 2100 |
| attgttagaa ataatgatcg tgtatatatt aatgtagtag ttaaaaataa agaatatagg | 2160 |
| ttagctacta atgcatcaca ggcaggcgta gaaaaaatac taagtgcatt agaaatacct | 2220 |
| gatgtaggaa atctaagtca gtagtagta atgaagtcaa aaaatgatca aggaataaca | 2280 |
| aataaatgca aaatgaattt acaagataat aatgggaatg ataggctt tataggattt | 2340 |
| catcagtttta ataatatagc taaactagta gcaagtaatt ggtataatag acaaatagaa | 2400 |
| agatctagta ggactttggg ttgctcatgg gaatttattc ctgtagatga tggatggaga | 2460 |
| gaaaggccac tgtaa | 2475 |

<210> SEQ ID NO 18
<211> LENGTH: 2541
<212> TYPE: DNA
<213> ORGANISM: Clostridium botulinum

<400> SEQUENCE: 18

| | |
|---|---|
| aatgatttat gtatcaaagt taataattgg gacttgtttt ttagtccttc agaagataat | 60 |
| tttactaatg atttagataa agtagaagaa attacagctg ataccaatat agaagcagca | 120 |
| gaagaaaata ttagtttaga tttaatacaa caatattatt taacttttga ttttgataat | 180 |
| gaacctgaaa atatttcaat agaaaatctt tcaagtgata ttataggcca attagagcct | 240 |
| atgcctaata tagaaagatt tcctaatgga aaaaagtatg agttagataa atatactatg | 300 |
| ttccattatc ttcgtgctca agaatttgaa catggtgatt ctagaattat cttaacaaat | 360 |

| | | |
|---|---|---|
| tctgctgaag aagcattatt aaagcctaat gttgcttata cattttttc ttcaaaatat | 420 |
| gtaaagaaga ttaataaagc cgtagaggca tttatgtttt taaattgggc agaagagtta | 480 |
| gtatatgact ttaccgatga aactaatgaa gtaactacta tggataaaat tgctgatata | 540 |
| actataattg ttccatatat agggcctgct ttaaatatag gtaatatgtt atctaaagga | 600 |
| gagtttgtag aagctataat atttacggga gttgttgcta tgttagaatt ataccagag | 660 |
| tatgctctcc ctgtatttgg tacttttgca attgtatcat atattgccaa taaggttcta | 720 |
| actgttcaaa caataaataa tgctttaagt aaaagaaatg aaaaatggga tgaagtctat | 780 |
| aaatatacag taacaaattg gctagcaaag gttaatacac agattgatct aataagggaa | 840 |
| aaaatgaaaa aagctttaga aaatcaggca gaagcaacaa aggctataat aaactatcag | 900 |
| tataatcaat atactgagga agagaaaaat aatattaatt ttaatattga tgatttaagt | 960 |
| tcgaaactta atgagtctat aaatagcgct atgattaaca taaataaatt tttggatcaa | 1020 |
| tgctctgttt catatttaat gaattctatg ataccttatg ctgttaaacg gttaaaagat | 1080 |
| tttgatgcta gtgttagaga tgtattatta agtatatat atgataatag aggaacttta | 1140 |
| gttcttcaag tagatagatt aaaagatgaa gttaataata cacttagtgc agatataacct | 1200 |
| tttcagcttt ccaaatacgt agataataaa aaattattat ctacatttac tgaatatatt | 1260 |
| aagaatattg ttaatacctc tatattgagt atagtatata aaaagatgaa tttaatagat | 1320 |
| ttatctaggt atggagcaaa ataaatatt ggcgatagag tatattatga ttcaatagat | 1380 |
| aaaaatcaaa ttaattaat taatttagaa agtagtacaa ttgaggtaat tttaaaaaat | 1440 |
| gctattgtat ataatagtat gtatgaaaat tttagtacta gcttttggat aaaaattcct | 1500 |
| aagtatttta gcaagataaa tctaaataat gaatatacaa taataaattg tatagaaaat | 1560 |
| aattcaggat ggaaagtatc acttaattat ggtgaaataa tctggacttt gcaggataat | 1620 |
| aagcaaaaca tacaaagagt agtttttaaa tacagtcaaa tggttaatat atcagattat | 1680 |
| ataaacagat ggattttgt aactatcact aataatagac taactaaatc taaaattat | 1740 |
| ataaatggaa gattaataga tcaaaaacca atttcaaatt taggtaatat tcatgctagt | 1800 |
| aataagataa tgtttaaatt agatggctgt agagatccac gtagatacat catgataaaa | 1860 |
| tatttcaatc ttttcgataa agaattaaat gaaaaagaaa tcaaagattt atatgatagt | 1920 |
| caatcaaatt caggtatttt aaaagacttt tggggtaatt atttacaata tgataaacca | 1980 |
| tactatatgt taaatttatt tgatccaaat aaatatgtcg atgtaaataa tataggtatt | 2040 |
| agaggttata tgtatcttaa agggcctaga ggtagcgtag tgactacaaa catttattta | 2100 |
| aattcaactt tgtatgaggg gacaaaattt attataaaaa aatatgcttc tggaaatgaa | 2160 |
| gataatattg ttagaaataa tgatcgtgta tatattaatg tagtagttaa aaataaagaa | 2220 |
| tataggttag ctactaatgc atcacaggca ggcgtagaaa aaatactaag tgcattagaa | 2280 |
| atacctgatg taggaaatct aagtcaagta gtagtaatga agtcaaaaga tgatcaagga | 2340 |
| ataagaaata aatgcaaaat gaatttacaa gataataatg ggaatgatat aggtcttata | 2400 |
| ggatttcatc agtttaataa tatagctaaa ctagtagcaa gtaattggta taatagacaa | 2460 |
| gtaggaaaag ctagtaggac tttcggttgt tcatgggagt ttattcctgt agatgatgga | 2520 |
| tggggagaaa gttcactgta a | 2541 |

<210> SEQ ID NO 19
<211> LENGTH: 606
<212> TYPE: PRT
<213> ORGANISM: Clostridium botulinum

<400> SEQUENCE: 19

```
Thr Val Gln Thr Ile Asp Asn Ala Leu Ser Lys Arg Asn Glu Lys Trp
1               5                   10                  15

Asp Glu Val Tyr Lys Tyr Ile Val Thr Asn Trp Leu Ala Lys Val Asn
            20                  25                  30

Thr Gln Ile Asp Leu Ile Arg Lys Lys Met Lys Glu Ala Leu Glu Asn
        35                  40                  45

Gln Ala Glu Ala Thr Lys Ala Ile Ile Asn Tyr Gln Tyr Asn Gln Tyr
    50                  55                  60

Thr Glu Glu Lys Asn Asn Ile Asn Phe Asn Ile Asp Asp Leu Ser
65                  70                  75                  80

Ser Lys Leu Asn Glu Ser Ile Asn Lys Ala Met Ile Asn Ile Asn Lys
                85                  90                  95

Phe Leu Asn Gln Cys Ser Val Ser Tyr Leu Met Asn Ser Met Ile Pro
            100                 105                 110

Tyr Gly Val Lys Arg Leu Glu Asp Phe Asp Ala Ser Leu Lys Asp Ala
        115                 120                 125

Leu Leu Lys Tyr Ile Tyr Asp Asn Arg Gly Thr Leu Ile Gly Gln Val
130                 135                 140

Asp Arg Leu Lys Asp Lys Val Asn Asn Thr Leu Ser Thr Asp Ile Pro
145                 150                 155                 160

Phe Gln Leu Ser Lys Tyr Val Asp Asn Gln Arg Leu Leu Ser Thr Phe
                165                 170                 175

Thr Glu Tyr Ile Lys Asn Ile Ile Asn Thr Ser Ile Leu Asn Leu Arg
            180                 185                 190

Tyr Glu Ser Asn His Leu Ile Asp Leu Ser Arg Tyr Ala Ser Lys Ile
        195                 200                 205

Asn Ile Gly Ser Lys Val Asn Phe Asp Pro Ile Asp Lys Asn Gln Ile
    210                 215                 220

Gln Leu Phe Asn Leu Glu Ser Ser Lys Ile Glu Val Ile Leu Lys Asn
225                 230                 235                 240

Ala Ile Val Tyr Asn Ser Met Tyr Glu Asn Phe Ser Thr Ser Phe Trp
                245                 250                 255

Ile Arg Ile Pro Lys Tyr Phe Asn Ser Ile Ser Leu Asn Asn Glu Tyr
            260                 265                 270

Thr Ile Ile Asn Cys Met Glu Asn Asn Ser Gly Trp Lys Val Ser Leu
        275                 280                 285

Asn Tyr Gly Glu Ile Ile Trp Thr Leu Gln Asp Thr Gln Glu Ile Lys
    290                 295                 300

Gln Arg Val Val Phe Lys Tyr Ser Gln Met Ile Asn Ile Ser Asp Tyr
305                 310                 315                 320

Ile Asn Arg Trp Ile Phe Val Thr Ile Thr Asn Asn Arg Leu Asn Asn
                325                 330                 335

Ser Lys Ile Tyr Ile Asn Gly Arg Leu Ile Asp Gln Lys Pro Ile Ser
            340                 345                 350

Asn Leu Gly Asn Ile His Ala Ser Asn Asn Ile Met Phe Lys Leu Asp
        355                 360                 365

Gly Cys Arg Asp Thr His Arg Tyr Ile Trp Ile Lys Tyr Phe Asn Leu
    370                 375                 380

Phe Asp Lys Glu Leu Asn Glu Lys Glu Ile Lys Asp Leu Tyr Asp Asn
385                 390                 395                 400

Gln Ser Asn Ser Gly Ile Leu Lys Asp Phe Trp Gly Asp Tyr Leu Gln
                405                 410                 415
```

```
Tyr Asp Lys Pro Tyr Tyr Met Leu Asn Leu Tyr Asp Pro Asn Lys Tyr
            420                 425                 430

Val Asp Val Asn Asn Val Gly Ile Arg Gly Tyr Met Tyr Leu Lys Gly
            435                 440                 445

Pro Arg Gly Ser Val Met Thr Thr Asn Ile Tyr Leu Asn Ser Ser Leu
450                 455                 460

Tyr Arg Gly Thr Lys Phe Ile Ile Lys Lys Tyr Ala Ser Gly Asn Lys
465                 470                 475                 480

Asp Asn Ile Val Arg Asn Asn Asp Arg Val Tyr Ile Asn Val Val Val
            485                 490                 495

Lys Asn Lys Glu Tyr Arg Leu Ala Thr Asn Ala Ser Gln Ala Gly Val
            500                 505                 510

Glu Lys Ile Leu Ser Ala Leu Glu Ile Pro Asp Val Gly Asn Leu Ser
            515                 520                 525

Gln Val Val Met Lys Ser Lys Asn Asp Gln Gly Ile Thr Asn Lys
            530                 535                 540

Cys Lys Met Asn Leu Gln Asp Asn Asn Gly Asn Asp Ile Gly Phe Ile
545                 550                 555                 560

Gly Phe His Gln Phe Asn Asn Ile Ala Lys Leu Val Ala Ser Asn Leu
            565                 570                 575

Ser Asn Arg Gln Ile Glu Arg Ser Ser Arg Thr Leu Gly Cys Ser Trp
            580                 585                 590

Glu Phe Ile Pro Val Asp Asp Gly Trp Gly Glu Arg Pro Leu
            595                 600                 605

<210> SEQ ID NO 20
<211> LENGTH: 792
<212> TYPE: PRT
<213> ORGANISM: Clostridium botulinum

<400> SEQUENCE: 20

Thr Phe Asn Phe Asp Asn Glu Pro Glu Asn Ile Ser Ile Glu Asn Leu
1               5                   10                  15

Ser Ser Asp Ile Ile Gly Gln Leu Glu Leu Met Pro Asn Ile Glu Arg
            20                  25                  30

Phe Pro Asn Gly Lys Lys Tyr Glu Leu Asp Lys Tyr Thr Met Phe His
        35                  40                  45

Tyr Leu Arg Ala Gln Glu Phe Glu His Gly Lys Ser Arg Ile Ala Leu
    50                  55                  60

Thr Asn Ser Val Asn Glu Ala Leu Leu Asn Pro Ser Arg Val Tyr Thr
65                  70                  75                  80

Phe Phe Ser Ser Asp Tyr Val Lys Lys Val Asn Lys Ala Thr Glu Ala
                85                  90                  95

Ala Met Phe Leu Gly Trp Val Glu Gln Leu Val Tyr Asp Phe Thr Asp
            100                 105                 110

Glu Thr Ser Glu Val Ser Thr Thr Asp Lys Ile Ala Asp Ile Thr Ile
        115                 120                 125

Ile Ile Pro Tyr Ile Gly Pro Ala Leu Asn Ile Gly Asn Met Leu Tyr
    130                 135                 140

Lys Asp Asp Phe Val Gly Ala Leu Ile Phe Ser Gly Ala Val Ile Leu
145                 150                 155                 160

Leu Glu Phe Ile Pro Glu Ile Ala Ile Pro Val Leu Gly Thr Phe Ala
                165                 170                 175

Leu Val Ser Tyr Ile Ala Asn Lys Val Leu Thr Val Gln Thr Ile Asp
            180                 185                 190
```

```
Asn Ala Leu Ser Lys Arg Asn Glu Lys Trp Asp Glu Val Tyr Lys Tyr
            195                 200                 205
Ile Val Thr Asn Trp Leu Ala Lys Val Asn Thr Gln Ile Asp Leu Ile
        210                 215                 220
Arg Lys Lys Met Lys Glu Ala Leu Glu Asn Gln Ala Glu Ala Thr Lys
225                 230                 235                 240
Ala Ile Ile Asn Tyr Gln Tyr Asn Gln Tyr Thr Glu Glu Lys Asn
                245                 250                 255
Asn Ile Asn Phe Asn Ile Asp Asp Leu Ser Ser Lys Leu Asn Glu Ser
                260                 265                 270
Ile Asn Lys Ala Met Ile Asn Ile Asn Lys Phe Leu Asn Gln Cys Ser
            275                 280                 285
Val Ser Tyr Leu Met Asn Ser Met Ile Pro Tyr Gly Val Lys Arg Leu
        290                 295                 300
Glu Asp Phe Asp Ala Ser Leu Lys Asp Ala Leu Leu Lys Tyr Ile Tyr
305                 310                 315                 320
Asp Asn Arg Gly Thr Leu Ile Gly Gln Val Asp Arg Leu Lys Asp Lys
                325                 330                 335
Val Asn Asn Thr Leu Ser Thr Asp Ile Pro Phe Gln Leu Ser Lys Tyr
            340                 345                 350
Val Asp Asn Gln Arg Leu Leu Ser Thr Phe Thr Glu Tyr Ile Lys Asn
        355                 360                 365
Ile Ile Asn Thr Ser Ile Leu Asn Leu Arg Tyr Glu Ser Asn His Leu
370                 375                 380
Ile Asp Leu Ser Arg Tyr Ala Ser Lys Ile Asn Ile Gly Ser Lys Val
385                 390                 395                 400
Asn Phe Asp Pro Ile Asp Lys Asn Gln Ile Gln Leu Phe Asn Leu Glu
                405                 410                 415
Ser Ser Lys Ile Glu Val Ile Leu Lys Asn Ala Ile Val Tyr Asn Ser
            420                 425                 430
Met Tyr Glu Asn Phe Ser Thr Ser Phe Trp Ile Arg Ile Pro Lys Tyr
        435                 440                 445
Phe Asn Ser Ile Ser Leu Asn Asn Glu Tyr Thr Ile Ile Asn Cys Met
    450                 455                 460
Glu Asn Asn Ser Gly Trp Lys Val Ser Leu Asn Tyr Gly Glu Ile Ile
465                 470                 475                 480
Trp Thr Leu Gln Asp Thr Gln Glu Ile Lys Gln Arg Val Val Phe Lys
                485                 490                 495
Tyr Ser Gln Met Ile Asn Ile Ser Asp Tyr Ile Asn Arg Trp Ile Phe
            500                 505                 510
Val Thr Ile Thr Asn Asn Arg Leu Asn Asn Ser Lys Ile Tyr Ile Asn
        515                 520                 525
Gly Arg Leu Ile Asp Gln Lys Pro Ile Ser Asn Leu Gly Asn Ile His
    530                 535                 540
Ala Ser Asn Asn Ile Met Phe Lys Leu Asp Gly Cys Arg Asp Thr His
545                 550                 555                 560
Arg Tyr Ile Trp Ile Lys Tyr Phe Asn Leu Phe Asp Lys Glu Leu Asn
                565                 570                 575
Glu Lys Glu Ile Lys Asp Leu Tyr Asp Asn Gln Ser Asn Ser Gly Ile
            580                 585                 590
Leu Lys Asp Phe Trp Gly Asp Tyr Leu Gln Tyr Asp Lys Pro Tyr Tyr
        595                 600                 605
Met Leu Asn Leu Tyr Asp Pro Asn Lys Tyr Val Asp Val Asn Asn Val
```

-continued

```
                610                 615                 620
Gly Ile Arg Gly Tyr Met Tyr Leu Lys Gly Pro Arg Gly Ser Val Met
625                 630                 635                 640

Thr Thr Asn Ile Tyr Leu Asn Ser Ser Leu Tyr Arg Gly Thr Lys Phe
                645                 650                 655

Ile Ile Lys Lys Tyr Ala Ser Gly Asn Lys Asp Asn Ile Val Arg Asn
                660                 665                 670

Asn Asp Arg Val Tyr Ile Asn Val Val Lys Asn Lys Glu Tyr Arg
                675                 680                 685

Leu Ala Thr Asn Ala Ser Gln Ala Gly Val Glu Lys Ile Leu Ser Ala
                690                 695                 700

Leu Glu Ile Pro Asp Val Gly Asn Leu Ser Gln Val Val Met Lys
705                 710                 715                 720

Ser Lys Asn Asp Gln Gly Ile Thr Asn Lys Cys Lys Met Asn Leu Gln
                725                 730                 735

Asp Asn Asn Gly Asn Asp Ile Gly Phe Ile Gly Phe His Gln Phe Asn
                740                 745                 750

Asn Ile Ala Lys Leu Val Ala Ser Asn Leu Ser Asn Arg Gln Ile Glu
                755                 760                 765

Arg Ser Ser Arg Thr Leu Gly Cys Ser Trp Glu Phe Ile Pro Val Asp
                770                 775                 780

Asp Gly Trp Gly Glu Arg Pro Leu
785                 790

<210> SEQ ID NO 21
<211> LENGTH: 846
<212> TYPE: PRT
<213> ORGANISM: Clostridium botulinum

<400> SEQUENCE: 21

Asn Asp Leu Cys Ile Lys Val Asn Asn Trp Asp Leu Phe Phe Ser Pro
1               5                   10                  15

Ser Glu Asp Asn Phe Thr Asn Asp Leu Asp Lys Val Glu Glu Ile Thr
                20                  25                  30

Ala Asp Thr Asn Ile Glu Ala Ala Glu Glu Asn Ile Ser Leu Asp Leu
            35                  40                  45

Ile Gln Gln Tyr Tyr Leu Thr Phe Asp Phe Asp Asn Glu Pro Glu Asn
50                  55                  60

Ile Ser Ile Glu Asn Leu Ser Ser Asp Ile Ile Gly Gln Leu Glu Pro
65                  70                  75                  80

Met Pro Asn Ile Glu Arg Phe Pro Asn Gly Lys Lys Tyr Glu Leu Asp
                85                  90                  95

Lys Tyr Thr Met Phe His Tyr Leu Arg Ala Gln Glu Phe Glu His Gly
            100                 105                 110

Asp Ser Arg Ile Ile Leu Thr Asn Ser Ala Glu Glu Ala Leu Leu Lys
        115                 120                 125

Pro Asn Val Ala Tyr Thr Phe Phe Ser Ser Lys Tyr Val Lys Lys Ile
    130                 135                 140

Asn Lys Ala Val Glu Ala Phe Met Phe Leu Asn Trp Ala Glu Glu Leu
145                 150                 155                 160

Val Tyr Asp Phe Thr Asp Glu Thr Asn Glu Val Thr Thr Met Asp Lys
                165                 170                 175

Ile Ala Asp Ile Thr Ile Ile Val Pro Tyr Ile Gly Pro Ala Leu Asn
            180                 185                 190

Ile Gly Asn Met Leu Ser Lys Gly Glu Phe Val Glu Ala Ile Ile Phe
```

```
                195                 200                 205
Thr Gly Val Val Ala Met Leu Glu Phe Ile Pro Glu Tyr Ala Leu Pro
210                 215                 220

Val Phe Gly Thr Phe Ala Ile Val Ser Tyr Ile Ala Asn Lys Val Leu
225                 230                 235                 240

Thr Val Gln Thr Ile Asn Asn Ala Leu Ser Lys Arg Asn Glu Lys Trp
                245                 250                 255

Asp Glu Val Tyr Lys Tyr Thr Val Thr Asn Trp Leu Ala Lys Val Asn
                260                 265                 270

Thr Gln Ile Asp Leu Ile Arg Glu Lys Met Lys Lys Ala Leu Glu Asn
                275                 280                 285

Gln Ala Glu Ala Thr Lys Ala Ile Ile Asn Tyr Gln Tyr Asn Gln Tyr
                290                 295                 300

Thr Glu Glu Glu Lys Asn Asn Ile Asn Phe Asn Ile Asp Asp Leu Ser
305                 310                 315                 320

Ser Lys Leu Asn Glu Ser Ile Asn Ser Ala Met Ile Asn Ile Asn Lys
                325                 330                 335

Phe Leu Asp Gln Cys Ser Val Ser Tyr Leu Met Asn Ser Met Ile Pro
                340                 345                 350

Tyr Ala Val Lys Arg Leu Lys Asp Phe Asp Ala Ser Val Arg Asp Val
                355                 360                 365

Leu Leu Lys Tyr Ile Tyr Asp Asn Arg Gly Thr Leu Val Leu Gln Val
                370                 375                 380

Asp Arg Leu Lys Asp Glu Val Asn Asn Thr Leu Ser Ala Asp Ile Pro
385                 390                 395                 400

Phe Gln Leu Ser Lys Tyr Val Asp Asn Lys Lys Leu Leu Ser Thr Phe
                405                 410                 415

Thr Glu Tyr Ile Lys Asn Ile Val Asn Thr Ser Ile Leu Ser Ile Val
                420                 425                 430

Tyr Lys Lys Asp Asp Leu Ile Asp Leu Ser Arg Tyr Gly Ala Lys Ile
                435                 440                 445

Asn Ile Gly Asp Arg Val Tyr Tyr Asp Ser Ile Asp Lys Asn Gln Ile
                450                 455                 460

Lys Leu Ile Asn Leu Glu Ser Ser Thr Ile Glu Val Ile Leu Lys Asn
465                 470                 475                 480

Ala Ile Val Tyr Asn Ser Met Tyr Glu Asn Phe Ser Thr Ser Phe Trp
                485                 490                 495

Ile Lys Ile Pro Lys Tyr Phe Ser Lys Ile Asn Leu Asn Asn Glu Tyr
                500                 505                 510

Thr Ile Ile Asn Cys Ile Glu Asn Asn Ser Gly Trp Lys Val Ser Leu
                515                 520                 525

Asn Tyr Gly Glu Ile Ile Trp Thr Leu Gln Asp Asn Lys Gln Asn Ile
                530                 535                 540

Gln Arg Val Val Phe Lys Tyr Ser Gln Met Val Asn Ile Ser Asp Tyr
545                 550                 555                 560

Ile Asn Arg Trp Ile Phe Val Thr Ile Thr Asn Asn Arg Leu Thr Lys
                565                 570                 575

Ser Lys Ile Tyr Ile Asn Gly Arg Leu Ile Asp Gln Lys Pro Ile Ser
                580                 585                 590

Asn Leu Gly Asn Ile His Ala Ser Asn Lys Ile Met Phe Lys Leu Asp
                595                 600                 605

Gly Cys Arg Asp Pro Arg Arg Tyr Ile Met Ile Lys Tyr Phe Asn Leu
610                 615                 620
```

```
Phe Asp Lys Glu Leu Asn Glu Lys Glu Ile Lys Asp Leu Tyr Asp Ser
625                 630                 635                 640

Gln Ser Asn Ser Gly Ile Leu Lys Asp Phe Trp Gly Asn Tyr Leu Gln
            645                 650                 655

Tyr Asp Lys Pro Tyr Tyr Met Leu Asn Leu Phe Asp Pro Asn Lys Tyr
        660                 665                 670

Val Asp Val Asn Asn Ile Gly Ile Arg Gly Tyr Met Tyr Leu Lys Gly
            675                 680                 685

Pro Arg Gly Ser Val Val Thr Thr Asn Ile Tyr Leu Asn Ser Thr Leu
        690                 695                 700

Tyr Glu Gly Thr Lys Phe Ile Ile Lys Lys Tyr Ala Ser Gly Asn Glu
705                 710                 715                 720

Asp Asn Ile Val Arg Asn Asn Asp Arg Val Tyr Ile Asn Val Val Val
                725                 730                 735

Lys Asn Lys Glu Tyr Arg Leu Ala Thr Asn Ala Ser Gln Ala Gly Val
            740                 745                 750

Glu Lys Ile Leu Ser Ala Leu Glu Ile Pro Asp Val Gly Asn Leu Ser
        755                 760                 765

Gln Val Val Met Lys Ser Lys Asp Gln Gly Ile Arg Asn Lys
        770                 775                 780

Cys Lys Met Asn Leu Gln Asp Asn Asn Gly Asn Asp Ile Gly Phe Ile
785                 790                 795                 800

Gly Phe His Leu Tyr Asp Asn Ile Ala Lys Leu Val Ala Ser Asn Trp
                805                 810                 815

Tyr Asn Arg Gln Val Gly Lys Ala Ser Arg Thr Phe Gly Cys Ser Trp
            820                 825                 830

Glu Phe Ile Pro Val Asp Asp Gly Trp Gly Glu Ser Ser Leu
        835                 840                 845

<210> SEQ ID NO 22
<211> LENGTH: 2541
<212> TYPE: DNA
<213> ORGANISM: Clostridium botulinum

<400> SEQUENCE: 22
aatgatttat gtatcaaagt taataattgg gacttgtttt ttagtccttc agaagataat    60
tttactaatg atttagataa agtagaagaa attacagctg ataccaatat agaagcagca   120
gaagaaaata ttagtttaga tttaatacaa caatattatt taacttttga ttttgataat   180
gaacctgaaa atatttcaat agaaaatctt tcaagtgata ttataggcca attagagcct   240
atgcctaata tagaaagatt tcctaatgga aaaagtatg agttagataa atatactatg   300
ttccattatc ttcgtgctca agaatttgaa catggtgatt ctagaattat cttaacaaat   360
tctgctgaag aagcattatt aaagcctaat gttgcttata cattttttc ttcaaaatat   420 gtaaagaaga ttaataaagc cgtagaggca tttatgtttt taaattgggc agaagagtta   480
gtatatgact ttaccgatga aactaatgaa gtaactacta tggataaaat tgctgatata   540
actataattg ttccatatat agggcctgct ttaaatatag gtaatatgtt atctaaagga   600
gagtttgtag aagctataat atttacggga gttgttgcta tgttagaatt ataccagag   660 tatgctctcc ctgtatttgg tactttttgca attgtatcat atattgccaa taaggttcta   720
actgttcaaa caataaataa tgctttaagt aaaagaaatg aaaaatggga tgaagtctat   780
aaatatacag taacaaattg gctagcaaag gttaatacac agattgatct aataagggaa   840 aaatgaaaa aagctttaga aaatcaggca gaagcaacaa aggctataat aaactatcag   900
```

-continued

```
tataatcaat atactgagga agagaaaaat aatattaatt ttaatattga tgatttaagt    960
tcgaaactta atgagtctat aaatagcgct atgattaaca taaataaatt tttggatcaa   1020
tgctctgttt catatttaat gaattctatg ataccttatg ctgttaaacg gttaaaagat   1080
tttgatgcta gtgttagaga tgtattatta agtatatat  atgataatag aggaacttta   1140
gttcttcaag tagatagatt aaaagatgaa gttaataata cacttagtgc agatatacct   1200
tttcagcttt ccaaatacgt agataataaa aaattattat ctacatttac tgaatatatt   1260
aagaatattg ttaataccct ctatattgagt atagtatata aaaaagatga tttaatagat   1320
ttatctaggt atggagcaaa aataaatatt ggcgatagag tatattatga ttcaatagat   1380
aaaaatcaaa ttaaattaat taatttagaa agtagtacaa ttgaggtaat tttaaaaaat   1440
gctattgtat ataatagtat gtatgaaaat tttagtacta gcttttggat aaaaaattcct   1500
aagtatttta gcaagataaa tctaaataat gaatatacaa taataaattg tatagaaaat   1560
aattcaggat ggaaagtatc acttaattat ggtgaaataa tctggacttt gcaggataat   1620
aagcaaaaca tacaaagagt agttttttaa tacagtcaaa tggttaatat atcagattat   1680
ataaacagat ggatttttgt aactatcact aataatagac taactaaatc taaaatttat   1740
ataaatggaa gattaataga tcaaaaacca atttcaaatt taggtaatat tcatgctagt   1800
aataagataa tgtttaaatt agatggctgt agagatccac gtagatacat catgataaaa   1860
tatttcaatc ttttcgataa agaattaaat gaaaaagaaa tcaaagattt atatgatagt   1920
caatcaaatt caggtatttt aaaagacttt tgggtaatt  atttacaata tgataaacca   1980
tactatatgt taaatttatt tgatccaaat aaatatgtcg atgtaaataa tataggtatt   2040
agaggttata tgtatcttaa agggcctaga ggtagcgtag tgactacaaa catttattta   2100
aattcaactt tgtatgaggg gacaaaattt attataaaa  aatatgcttc tggaaatgaa   2160
gataatattg ttagaaataa tgatcgtgta tatattaatg tagtagttaa aaataaagaa   2220
tataggttag ctactaatgc atcacaggca ggcgtagaaa aaatactaag tgcattagaa   2280
atacctgatg taggaaatct aagtcaagta gtagtaatga agtcaaaaga tgatcaagga   2340
ataagaaata aatgcaaaat gaatttacaa gataataatg ggatgatat  aggctttata   2400
ggatttcatt tgtatgataa tatagctaaa ctagtagcaa gtaattggta taatagacaa   2460
gtgggaaaag ctagtaggac tttcggttgt tcatgggagt ttattcctgt agatgatgga   2520
tggggagaaa gttcactgta a                                            2541
```

<210> SEQ ID NO 23
<211> LENGTH: 846
<212> TYPE: PRT
<213> ORGANISM: Clostridium botulinum

<400> SEQUENCE: 23

```
Asn Asp Leu Cys Ile Lys Val Asn Asn Trp Asp Leu Phe Phe Ser Pro
1               5                   10                  15

Ser Glu Asp Asn Phe Thr Asn Asp Leu Asp Lys Val Glu Glu Ile Thr
            20                  25                  30

Ala Asp Thr Asn Ile Glu Ala Ala Glu Glu Asn Ile Ser Leu Asp Leu
        35                  40                  45

Ile Gln Gln Tyr Tyr Leu Thr Phe Asp Phe Asp Asn Glu Pro Glu Asn
    50                  55                  60

Ile Ser Ile Glu Asn Leu Ser Ser Asp Ile Ile Gly Gln Leu Glu Pro
65                  70                  75                  80

Met Pro Asn Ile Glu Arg Phe Pro Asn Gly Lys Lys Tyr Glu Leu Asp
```

```
                85                  90                  95
Lys Tyr Thr Met Phe His Tyr Leu Arg Ala Gln Glu Phe Glu His Gly
            100                 105                 110

Asp Ser Arg Ile Ile Leu Thr Asn Ser Ala Glu Glu Ala Leu Leu Lys
            115                 120                 125

Pro Asn Val Ala Tyr Thr Phe Phe Ser Ser Lys Tyr Val Lys Lys Ile
            130                 135                 140

Asn Lys Ala Val Glu Ala Phe Met Phe Leu Asn Trp Ala Glu Glu Leu
145                 150                 155                 160

Val Tyr Asp Phe Thr Asp Glu Thr Asn Glu Val Thr Thr Met Asp Lys
                165                 170                 175

Ile Ala Asp Ile Thr Ile Ile Val Pro Tyr Ile Gly Pro Ala Leu Asn
                180                 185                 190

Ile Gly Asn Met Leu Ser Lys Gly Glu Phe Val Glu Ala Ile Ile Phe
                195                 200                 205

Thr Gly Val Val Ala Met Leu Glu Phe Ile Pro Glu Tyr Ala Leu Pro
210                 215                 220

Val Phe Gly Thr Phe Ala Ile Val Ser Tyr Ile Ala Asn Lys Val Leu
225                 230                 235                 240

Thr Val Gln Thr Ile Asn Asn Ala Leu Ser Lys Arg Asn Glu Lys Trp
                245                 250                 255

Asp Glu Val Tyr Lys Tyr Thr Val Thr Asn Trp Leu Ala Lys Val Asn
                260                 265                 270

Thr Gln Ile Asp Leu Ile Arg Glu Lys Met Lys Lys Ala Leu Glu Asn
                275                 280                 285

Gln Ala Glu Ala Thr Lys Ala Ile Ile Asn Tyr Gln Tyr Asn Gln Tyr
                290                 295                 300

Thr Glu Glu Glu Lys Asn Asn Ile Asn Phe Asn Ile Asp Asp Leu Ser
305                 310                 315                 320

Ser Lys Leu Asn Glu Ser Ile Asn Ser Ala Met Ile Asn Ile Asn Lys
                325                 330                 335

Phe Leu Asp Gln Cys Ser Val Ser Tyr Leu Met Asn Ser Met Ile Pro
                340                 345                 350

Tyr Ala Val Lys Arg Leu Lys Asp Phe Asp Ala Ser Val Arg Asp Val
                355                 360                 365

Leu Leu Lys Tyr Ile Tyr Asp Asn Arg Gly Thr Leu Val Leu Gln Val
                370                 375                 380

Asp Arg Leu Lys Asp Glu Val Asn Asn Thr Leu Ser Ala Asp Ile Pro
385                 390                 395                 400

Phe Gln Leu Ser Lys Tyr Val Asp Asn Lys Lys Leu Leu Ser Thr Phe
                405                 410                 415

Thr Glu Tyr Ile Lys Asn Ile Val Asn Thr Ser Ile Leu Ser Ile Val
                420                 425                 430

Tyr Lys Lys Asp Asp Leu Ile Asp Leu Ser Arg Tyr Gly Ala Lys Ile
                435                 440                 445

Asn Ile Gly Asp Arg Val Tyr Tyr Asp Ser Ile Asp Lys Asn Gln Ile
                450                 455                 460

Lys Leu Ile Asn Leu Glu Ser Ser Thr Ile Glu Val Ile Leu Lys Asn
465                 470                 475                 480

Ala Ile Val Tyr Asn Ser Met Tyr Glu Asn Phe Ser Thr Ser Phe Trp
                485                 490                 495

Ile Lys Ile Pro Lys Tyr Phe Ser Lys Ile Asn Leu Asn Asn Glu Tyr
                500                 505                 510
```

```
Thr Ile Ile Asn Cys Ile Glu Asn Asn Ser Gly Trp Lys Val Ser Leu
        515                 520                 525

Asn Tyr Gly Glu Ile Ile Trp Thr Leu Gln Asp Asn Lys Gln Asn Ile
    530                 535                 540

Gln Arg Val Val Phe Lys Tyr Ser Gln Met Val Asn Ile Ser Asp Tyr
545                 550                 555                 560

Ile Asn Arg Trp Ile Phe Val Thr Ile Thr Asn Asn Arg Leu Thr Lys
                565                 570                 575

Ser Lys Ile Tyr Ile Asn Gly Arg Leu Ile Asp Gln Lys Pro Ile Ser
            580                 585                 590

Asn Leu Gly Asn Ile His Ala Ser Asn Lys Ile Met Phe Lys Leu Asp
        595                 600                 605

Gly Cys Arg Asp Pro Arg Arg Tyr Ile Met Ile Lys Tyr Phe Asn Leu
    610                 615                 620

Phe Asp Lys Glu Leu Asn Glu Lys Glu Ile Lys Asp Leu Tyr Asp Ser
625                 630                 635                 640

Gln Ser Asn Ser Gly Ile Leu Lys Asp Phe Trp Gly Asn Tyr Leu Gln
                645                 650                 655

Tyr Asp Lys Pro Tyr Tyr Met Leu Asn Leu Phe Asp Pro Asn Lys Tyr
            660                 665                 670

Val Asp Val Asn Asn Ile Gly Ile Arg Gly Tyr Met Tyr Leu Lys Gly
        675                 680                 685

Pro Arg Gly Arg Val Val Thr Thr Asn Ile Tyr Leu Asn Ser Thr Leu
    690                 695                 700

Tyr Glu Gly Thr Lys Phe Ile Ile Lys Lys Tyr Ala Ser Gly Asn Glu
705                 710                 715                 720

Asp Asn Ile Val Arg Asn Asn Asp Arg Val Tyr Ile Asn Val Val Val
                725                 730                 735

Lys Asn Lys Glu Tyr Arg Leu Ala Thr Asn Ala Ser Gln Ala Gly Val
            740                 745                 750

Glu Lys Ile Leu Ser Ala Leu Glu Ile Pro Asp Val Gly Asn Leu Ser
        755                 760                 765

Gln Val Val Val Met Lys Ser Lys Asp Asp Gln Gly Ile Arg Asn Lys
    770                 775                 780

Cys Lys Met Asn Leu Gln Asp Asn Asn Gly Asn Asp Ile Gly Phe Ile
785                 790                 795                 800

Gly Phe His Leu Tyr Asp Asn Ile Ala Lys Leu Val Ala Ser Asn Trp
                805                 810                 815

Tyr Asn Arg Gln Val Gly Lys Ala Ser Arg Thr Phe Gly Cys Ser Trp
            820                 825                 830

Glu Phe Ile Pro Val Asp Asp Gly Trp Gly Glu Ser Ser Leu
        835                 840                 845

<210> SEQ ID NO 24
<211> LENGTH: 2541
<212> TYPE: DNA
<213> ORGANISM: Clostridium botulinum

<400> SEQUENCE: 24 aatgattat  gtatcaaagt  taataattgg  gacttgtttt  ttagtccttc  agaagataat      60
tttactaatg  atttagataa  agtagaagaa  attcagctg  ataccaatat  agaagcagca    120
gaagaaaata  ttagtttaga  tttaatacaa  caatattatt  taactttga  ttttgataat     180 gaacctgaaa  atatttcaat  agaaaatctt  tcaagtgata  ttataggcca  attagagcct   240
atgcctaata  tagaaagatt  tcctaatgga  aaaaagtatg  agttagataa  atatactatg  300
```

```
ttccattatc ttcgtgctca agaatttgaa catggtgatt ctagaattat cttaacaaat      360
tctgctgaag aagcattatt aaagcctaat gttgcttata catttttttc ttcaaaatat      420
gtaaagaaga ttaataaagc cgtagaggca tttatgtttt taaattgggc agaagagtta      480
gtatatgact ttaccgatga aactaatgaa gtaactacta tggataaaat tgctgatata      540
actataattg ttccatatat agggcctgct ttaaatatag gtaatatgtt atctaaagga      600
gagtttgtag aagctataat atttacggga gttgttgcta tgttagaatt tataccagag      660
tatgctctcc ctgtatttgg tacttttgca attgtatcat atattgccaa taaggttcta      720
actgttcaaa caataaataa tgctttaagt aaaagaaatg aaaatgggga tgaagtctat      780
aaatatacag taacaaattg gctagcaaag gttaatacac agattgatct aataagggaa      840
aaaatgaaaa agctttaga aaatcaggca gaagcaacaa aggctataat aaactatcag      900
tataatcaat atactgagga agagaaaaat aatattaatt ttaatattga tgatttaagt      960
tcgaaactta atgagtctat aaatagcgct atgattaaca taaataaatt tttggatcaa     1020
tgctctgttt catatttaat gaattctatg ataccttatg ctgttaaacg gttaaaagat     1080
tttgatgcta gtgttagaga tgtattatta agtatatat atgataatag aggaacttta     1140
gttcttcaag tagatagatt aaaagatgaa gttaataata cacttagtgc agatatacct     1200
tttcagcttt ccaaatacgt agataataaa aaattattat ctacatttac tgaatatatt     1260
aagaatattg ttaatacctc tatattgagt atagtatata aaaagatga tttaatagat     1320 ttatctaggt atggagcaaa aataaatatt ggcgatagag tatattatga ttcaatagat     1380
aaaaatcaaa ttaaattaat taatttagaa agtagtacaa ttgaggtaat tttaaaaaat     1440
gctattgtat ataatagtat gtatgaaaat tttagtacta gcttttggat aaaaattcct     1500
aagtatttta gcaagataaa tctaaataat gaatatacaa taataaattg tatagaaaat     1560
aattcaggat ggaaagtatc acttaattat ggtgaaataa tctggacttt gcaggataat     1620
aagcaaaaca tacaaagagt agttttttaaa tacagtcaaa tggttaatat atcagattat     1680
ataaacagat ggattttttgt aactatcact aataatagac taactaaatc taaaatttat     1740
ataaatggaa gattaataga tcaaaaacca atttcaaatt taggtaatat tcatgctagt     1800
aataagataa tgtttaaatt agatggctgt agagatccac gtagatacat catgataaaa     1860
tatttcaatc ttttcgataa agaattaaat gaaaaagaaa tcaagatttt atatgatagt     1920
caatcaaatt caggtatttt aaaagacttt tggggtaatt atttacaata tgataaacca     1980
tactatatgt taaattttatt tgatccaaat aaatatgtcg atgtaaataa tataggtatt     2040
agaggttata tgtatcttaa agggcctaga ggtagagtag tgactacaaa catttattta     2100
aattcaactt tgtatgaggg gacaaaattt attataaaaa aatatgcttc tggaaatgaa     2160
gataatattg ttagaaataa tgatcgtgta tatattaatg tagtagttaa aaataaagaa     2220
tataggttag ctactaatgc atcacaggca ggcgtagaaa aaatactaag tgcattagaa     2280
atacctgatg taggaaatct aagtcaagta gtagtaatga agtcaaaaga tgatcaagga     2340
ataagaaata aatgcaaaat gaatttacaa gataataatg ggaatgatat aggctttata     2400
ggatttcatt tgtatgataa tatagctaaa ctagtagcaa gtaattggta taatagacaa     2460
gtgggaaaag ctagtaggac tttcggttgt tcatgggagt ttattcctgt agatgatgga     2520
tggggagaga gttcactgta a                                                2541
```

<210> SEQ ID NO 25
<211> LENGTH: 846

<212> TYPE: PRT
<213> ORGANISM: Clostridium botulinum

<400> SEQUENCE: 25

```
Asn Tyr Leu Cys Ile Lys Val Asn Asn Trp Asp Leu Phe Phe Ser Pro
1               5                   10                  15

Ser Glu Asp Asn Phe Thr Asn Asp Leu Asp Lys Val Glu Glu Ile Thr
            20                  25                  30

Ala Asp Thr Asn Ile Glu Ala Glu Glu Asn Ile Ser Ser Asp Leu
        35                  40                  45

Ile Gln Gln Tyr Tyr Leu Thr Phe Asp Phe Asp Asn Glu Pro Glu Asn
    50                  55                  60

Ile Ser Ile Glu Asn Leu Ser Ser Asp Ile Ile Gly Gln Leu Glu Pro
65                  70                  75                  80

Met Pro Asn Ile Glu Arg Phe Pro Asn Gly Lys Lys Tyr Glu Leu Asp
                85                  90                  95

Lys Tyr Thr Met Phe His Tyr Leu Arg Ala Gln Glu Phe Glu His Gly
            100                 105                 110

Asp Ser Arg Ile Ile Leu Thr Asn Ser Ala Glu Glu Ala Leu Leu Lys
        115                 120                 125

Pro Asn Val Ala Tyr Thr Phe Phe Ser Ser Lys Tyr Val Lys Lys Ile
    130                 135                 140

Asn Lys Ala Val Glu Ala Val Ile Phe Leu Ser Trp Ala Glu Glu Leu
145                 150                 155                 160

Val Tyr Asp Phe Thr Asp Glu Thr Asn Glu Val Thr Thr Met Asp Lys
                165                 170                 175

Ile Ala Asp Ile Thr Ile Ile Val Pro Tyr Ile Gly Pro Ala Leu Asn
            180                 185                 190

Ile Gly Asn Met Val Ser Lys Gly Glu Phe Val Glu Ala Ile Leu Phe
        195                 200                 205

Thr Gly Val Val Ala Leu Leu Glu Phe Ile Pro Glu Tyr Ser Leu Pro
    210                 215                 220

Val Phe Gly Thr Phe Ala Ile Val Ser Tyr Ile Ala Asn Lys Val Leu
225                 230                 235                 240

Thr Val Gln Thr Ile Asn Asn Ala Leu Ser Lys Arg Asn Glu Lys Trp
                245                 250                 255

Asp Glu Val Tyr Lys Tyr Thr Val Thr Asn Trp Leu Ala Lys Val Asn
            260                 265                 270

Thr Gln Ile Asp Leu Ile Arg Glu Lys Met Lys Lys Ala Leu Glu Asn
        275                 280                 285

Gln Ala Glu Ala Thr Arg Ala Ile Ile Asn Tyr Gln Tyr Asn Gln Tyr
    290                 295                 300

Thr Glu Glu Glu Lys Asn Asn Ile Asn Phe Asn Ile Asp Asp Leu Ser
305                 310                 315                 320

Ser Lys Leu Asn Arg Ser Ile Asn Arg Ala Met Ile Asn Ile Asn Lys
                325                 330                 335

Phe Leu Asp Gln Cys Ser Val Ser Tyr Leu Met Asn Ser Met Ile Pro
            340                 345                 350

Tyr Ala Val Lys Arg Leu Lys Asp Phe Asp Ala Ser Val Arg Asp Val
        355                 360                 365

Leu Leu Lys Tyr Ile Tyr Asp Asn Arg Gly Thr Leu Ile Leu Gln Val
    370                 375                 380

Asp Arg Leu Lys Asp Glu Val Asn Asn Thr Leu Ser Ala Asp Ile Pro
385                 390                 395                 400
```

-continued

```
Phe Gln Leu Ser Lys Tyr Val Asn Asp Lys Lys Leu Leu Ser Thr Phe
            405                 410                 415
Thr Glu Tyr Ile Lys Asn Ile Val Asn Thr Ser Ile Leu Ser Ile Val
            420                 425                 430
Tyr Lys Lys Asp Asp Leu Ile Asp Leu Ser Arg Tyr Gly Ala Lys Ile
            435                 440                 445
Asn Ile Gly Asp Arg Val Tyr Tyr Asp Ser Ile Asp Lys Asn Gln Ile
        450                 455                 460
Lys Leu Ile Asn Leu Glu Ser Ser Thr Ile Glu Val Ile Leu Lys Asn
465                 470                 475                 480
Ala Ile Val Tyr Asn Ser Met Tyr Glu Asn Phe Ser Thr Ser Phe Trp
            485                 490                 495
Ile Lys Ile Pro Lys Tyr Phe Ser Lys Ile Asn Leu Asn Asn Glu Tyr
            500                 505                 510
Thr Ile Ile Asn Cys Ile Glu Asn Asn Ser Gly Trp Lys Val Ser Leu
            515                 520                 525
Asn Tyr Gly Glu Ile Ile Trp Thr Leu Gln Asp Asn Lys Gln Asn Ile
        530                 535                 540
Gln Arg Val Val Phe Lys Tyr Ser Gln Met Val Asn Ile Ser Asp Tyr
545                 550                 555                 560
Ile Asn Arg Trp Met Phe Val Thr Ile Thr Asn Asn Arg Leu Thr Lys
            565                 570                 575
Ser Lys Ile Tyr Ile Asn Gly Arg Leu Ile Asp Gln Lys Pro Ile Ser
            580                 585                 590
Asn Leu Gly Asn Ile His Ala Ser Asn Lys Ile Met Phe Lys Leu Asp
            595                 600                 605
Gly Cys Arg Asp Pro Arg Arg Tyr Ile Met Ile Lys Tyr Phe Asn Leu
        610                 615                 620
Phe Asp Lys Glu Leu Asn Glu Lys Glu Ile Lys Asp Leu Tyr Asp Ser
625                 630                 635                 640
Gln Ser Asn Pro Gly Ile Leu Lys Asp Phe Trp Gly Asn Tyr Leu Gln
            645                 650                 655
Tyr Asp Lys Pro Tyr Tyr Met Leu Asn Leu Phe Asp Pro Asn Lys Tyr
            660                 665                 670
Val Asp Val Asn Asn Ile Gly Ile Arg Gly Tyr Met Tyr Leu Lys Gly
            675                 680                 685
Pro Arg Gly Ser Val Met Thr Thr Asn Ile Tyr Leu Asn Ser Thr Leu
        690                 695                 700
Tyr Met Gly Thr Lys Phe Ile Ile Lys Lys Tyr Ala Ser Gly Asn Glu
705                 710                 715                 720
Asp Asn Ile Val Arg Asn Asn Asp Arg Val Tyr Ile Asn Val Val Val
            725                 730                 735
Lys Asn Lys Glu Tyr Arg Leu Ala Thr Asn Ala Ser Gln Ala Gly Val
            740                 745                 750
Glu Lys Ile Leu Ser Ala Leu Glu Ile Pro Asp Val Gly Asn Leu Ser
            755                 760                 765
Gln Val Val Val Met Lys Ser Lys Asp Asp Gln Gly Ile Arg Asn Lys
        770                 775                 780
Cys Lys Met Asn Leu Gln Asp Asn Asn Gly Asn Asp Ile Gly Phe Val
785                 790                 795                 800
Gly Phe His Leu Tyr Asp Asn Ile Ala Lys Leu Val Ala Ser Asn Trp
            805                 810                 815
Tyr Asn Arg Gln Val Gly Lys Ala Ser Arg Thr Phe Gly Cys Ser Trp
            820                 825                 830
```

Glu Phe Ile Pro Val Asp Asp Gly Trp Gly Glu Ser Ser Leu
　　　835　　　　　　　840　　　　　　　　845

<210> SEQ ID NO 26
<211> LENGTH: 2541
<212> TYPE: DNA
<213> ORGANISM: Clostridium botulinum

<400> SEQUENCE: 26

```
aattatttat gtatcaaagt taataattgg gacttgtttt ttagtccttc agaagataat      60
tttactaatg atttagataa agtagaagaa attacagctg ataccaatat agaagcagca     120
gaagaaaata ttagttcaga tttaatacaa caatattatt taacttttga ttttgataat     180
gaacctgaaa atatttcaat agaaaatctt tcaagtgata ttataggcca attagagcct     240
atgcctaata tagaaagatt tcccaatgga aaaagtatg agttagataa atatactatg      300
ttccattatc ttcgtgctca agaatttgaa catggtgatt ctagaattat cttaacaaat     360
tctgctgaag aagcattatt aaagcctaat gttgcttaca catttttttc ttcaaaatat     420
gtaaagaaga ttaataaagc cgtagaggca gttattttt taagttgggc agaagagtta      480
gtatatgact ttaccgatga aactaatgaa gtaactacta tggataaaat tgctgatata     540
actataattg ttccatatat agggcctgct ttaaatatag gtaatatggt atctaaagga     600
gagttcgtag aagctatact atttacggga gttgttgctc tgttagaatt ataccagag     660
tattccctcc ctgtatttgg tactttttgca attgtatcat atattgccaa taaggttcta    720
actgttcaaa caataaataa tgctttaagt aaaagaaatg aaaaatggga tgaagtctat     780
aaatatacag taacaaattg gctagcaaag gttaatacac agattgatct aataagggaa     840
aaaatgaaaa aagctttaga aaatcaggca gaagcaacaa gggctataat aaactatcag     900
tataatcaat atactgagga agagaaaaat aatattaatt taatattga tgatttaagt      960
tcgaaactta ataggtctat aaataggct atgattaaca taaataaatt tttggatcaa    1020
tgctctgttt catatttaat gaattctatg ataccttatg ctgttaaacg gttaaaagat    1080
tttgatgcta gtgttagaga tgtattatta agtatatat atgataatag aggaactta     1140
attcttcaag tagatagatt aaaagatgaa gttaataata cacttagtgc agatatacct    1200
tttcagcttt ctaaatacgt aaatgataaa aaattattat ctacatttac tgaatatatt    1260
aagaatattg ttaataccct ctatattgagt atagtatata aaaagatga tttaatagat    1320
ttatctaggt atggagcaaa aataaatatt ggcgatagag tatattatga ttcaatagat    1380
aaaaatcaaa ttaaattaat taattagaa agtagtacaa ttgaggtaat tttaaaaaat    1440
gctattgtat ataatagtat gtatgaaaat tttagtacta gcttttggat aaaaattcct    1500
aagtattta gcaagataaa tctaaataat gaatatacaa taataaattg tatagaaaat    1560
aattcaggat ggaaagtatc acttaattat ggtgaaataa tctggacttt gcaggataat    1620
aagcaaaaca tacaaagagt agtttttaaa tacagtcaaa tggttaatat atcagattat    1680
ataaacagat ggatgtttgt aactatcact aataatagac taactaaatc taaaatttat    1740
ataaatggaa gattaataga tcaaaaacca atttcaaatt tgggtaatat tcatgctagt    1800
aataagataa tgtttaaatt agatggctgt agagatccac gtagatacat catgataaaa    1860
tatttcaatc ttttcgataa agaattaaat gaaaagaaa tcaagatttt atatgatagt    1920
caatcaaatc caggtatttt aaaagacttt tgggtaat atttacaata tgataaacca    1980
tactatatgt taaatttatt tgatccaaat aaatatgtcg atgtaaataa tataggtatt    2040
```

```
agaggttata tgtatcttaa agggcctaga ggtagcgtaa tgactacaaa catttattta    2100
aattcaactt tgtatatggg acaaaattt attataaaaa aatatgcttc tggaaatgaa     2160
gataatattg ttagaaataa tgatcgtgta tatattaatg tagtagttaa aaataaagaa    2220
tataggttag ctactaatgc atcacaggca ggcgtagaaa aaatactaag tgcattagaa    2280
atacctgatg taggaaatct aagtcaagta gtagtaatga agtcaaaaga tgatcaagga    2340
ataagaaata aatgcaaaat gaatttacaa gataataatg ggaatgatat aggctttgta    2400
ggatttcatt tgtatgataa tatagctaaa ctagtagcaa gtaattggta aatagacaa     2460 gtgggaaaag ctagtaggac tttcggttgt tcatgggagt ttattcctgt agatgatgga    2520
tggggagaaa gttcactgta a                                              2541
```

<210> SEQ ID NO 27
<211> LENGTH: 438
<212> TYPE: PRT
<213> ORGANISM: Clostridium botulinum
<220> FEATURE:
<221> NAME/KEY: MISC_FEATURE
<222> LOCATION: (1)..(438)
<223> OTHER INFORMATION: BoNT/A light chain

<400> SEQUENCE: 27

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

```
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys
            435

<210> SEQ ID NO 28
<211> LENGTH: 1043
<212> TYPE: PRT
<213> ORGANISM: Artificial
<220> FEATURE:
<223> OTHER INFORMATION: recombinantly-created fusion protein LC-HC66/A
      comprising BoNT/A LC fused to HC66
<220> FEATURE:
<221> NAME/KEY: MISC_FEATURE
<222> LOCATION: (1)..(438)
<223> OTHER INFORMATION: light chain of BoNT/A
<220> FEATURE:
<221> NAME/KEY: MISC_FEATURE
<222> LOCATION: (439)..(1043)
<223> OTHER INFORMATION: HC66 of BoNT/A

<400> SEQUENCE: 28

Met Pro Phe Val Asn Lys Gln Phe Asn Tyr Lys Asp Pro Val Asn Gly
1               5                   10                  15
Val Asp Ile Ala Tyr Ile Lys Ile Pro Asn Ala Gly Gln Met Gln Pro
            20                  25                  30
Val Lys Ala Phe Lys Ile His Asn Lys Ile Trp Val Ile Pro Glu Arg
        35                  40                  45
Asp Thr Phe Thr Asn Pro Glu Glu Gly Asp Leu Asn Pro Pro Pro Glu
    50                  55                  60
Ala Lys Gln Val Pro Val Ser Tyr Tyr Asp Ser Thr Tyr Leu Ser Thr
65                  70                  75                  80
Asp Asn Glu Lys Asp Asn Tyr Leu Lys Gly Val Thr Lys Leu Phe Glu
                85                  90                  95
Arg Ile Tyr Ser Thr Asp Leu Gly Arg Met Leu Leu Thr Ser Ile Val
            100                 105                 110
Arg Gly Ile Pro Phe Trp Gly Gly Ser Thr Ile Asp Thr Glu Leu Lys
        115                 120                 125
Val Ile Asp Thr Asn Cys Ile Asn Val Ile Gln Pro Asp Gly Ser Tyr
    130                 135                 140
```

-continued

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Val Gln Thr Ile Asp Asn Ala Leu Ser Lys
    435                 440                 445

Arg Asn Glu Lys Trp Asp Glu Val Tyr Lys Tyr Ile Val Thr Asn Trp
450                 455                 460

Leu Ala Lys Val Asn Thr Gln Ile Asp Leu Ile Arg Lys Lys Met Lys
465                 470                 475                 480

Glu Ala Leu Glu Asn Gln Ala Glu Ala Thr Lys Ala Ile Ile Asn Tyr
                485                 490                 495

Gln Tyr Asn Gln Tyr Thr Glu Glu Lys Asn Asn Ile Asn Phe Asn
            500                 505                 510

Ile Asp Asp Leu Ser Ser Lys Leu Asn Glu Ser Ile Asn Lys Ala Met
        515                 520                 525

Ile Asn Ile Asn Lys Phe Leu Asn Gln Cys Ser Val Ser Tyr Leu Met
    530                 535                 540

Asn Ser Met Ile Pro Tyr Gly Val Lys Arg Leu Glu Asp Phe Asp Ala
545                 550                 555                 560

Ser Leu Lys Asp Ala Leu Leu Lys Tyr Ile Tyr Asp Asn Arg Gly Thr
                565                 570                 575
```

```
Leu Ile Gly Gln Val Asp Arg Leu Lys Asp Lys Val Asn Asn Thr Leu
            580                 585                 590

Ser Thr Asp Ile Pro Phe Gln Leu Ser Lys Tyr Val Asp Asn Gln Arg
            595                 600                 605

Leu Leu Ser Thr Phe Thr Glu Tyr Ile Lys Asn Ile Ile Asn Thr Ser
610                 615                 620

Ile Leu Asn Leu Arg Tyr Glu Ser Asn His Leu Ile Asp Leu Ser Arg
625                 630                 635                 640

Tyr Ala Ser Lys Ile Asn Ile Gly Ser Lys Val Asn Phe Asp Pro Ile
                645                 650                 655

Asp Lys Asn Gln Ile Gln Leu Phe Asn Leu Glu Ser Ser Lys Ile Glu
                660                 665                 670

Val Ile Leu Lys Asn Ala Ile Val Tyr Asn Ser Met Tyr Glu Asn Phe
                675                 680                 685

Ser Thr Ser Phe Trp Ile Arg Ile Pro Lys Tyr Phe Asn Ser Ile Ser
            690                 695                 700

Leu Asn Asn Glu Tyr Thr Ile Ile Asn Cys Met Glu Asn Asn Ser Gly
705                 710                 715                 720

Trp Lys Val Ser Leu Asn Tyr Gly Glu Ile Ile Trp Thr Leu Gln Asp
                725                 730                 735

Thr Gln Glu Ile Lys Gln Arg Val Val Phe Lys Tyr Ser Gln Met Ile
            740                 745                 750

Asn Ile Ser Asp Tyr Ile Asn Arg Trp Ile Phe Val Thr Ile Thr Asn
            755                 760                 765

Asn Arg Leu Asn Asn Ser Lys Ile Tyr Ile Asn Gly Arg Leu Ile Asp
            770                 775                 780

Gln Lys Pro Ile Ser Asn Leu Gly Asn Ile His Ala Ser Asn Asn Ile
785                 790                 795                 800

Met Phe Lys Leu Asp Gly Cys Arg Asp Thr His Arg Tyr Ile Trp Ile
            805                 810                 815

Lys Tyr Phe Asn Leu Phe Asp Lys Glu Leu Asn Glu Lys Glu Ile Lys
            820                 825                 830

Asp Leu Tyr Asp Asn Gln Ser Asn Ser Gly Ile Leu Lys Asp Phe Trp
            835                 840                 845

Gly Asp Tyr Leu Gln Tyr Asp Lys Pro Tyr Tyr Met Leu Asn Leu Tyr
850                 855                 860

Asp Pro Asn Lys Tyr Val Asp Val Asn Asn Val Gly Ile Arg Gly Tyr
865                 870                 875                 880

Met Tyr Leu Lys Gly Pro Arg Gly Ser Val Met Thr Thr Asn Ile Tyr
                885                 890                 895

Leu Asn Ser Ser Leu Tyr Arg Gly Thr Lys Phe Ile Ile Lys Lys Tyr
                900                 905                 910

Ala Ser Gly Asn Lys Asp Asn Ile Val Arg Asn Asn Asp Arg Val Tyr
                915                 920                 925

Ile Asn Val Val Val Lys Asn Lys Glu Tyr Arg Leu Ala Thr Asn Ala
            930                 935                 940

Ser Gln Ala Gly Val Glu Lys Ile Leu Ser Ala Leu Glu Ile Pro Asp
945                 950                 955                 960

Val Gly Asn Leu Ser Gln Val Val Val Met Lys Ser Lys Asn Asp Gln
                965                 970                 975

Gly Ile Thr Asn Lys Cys Lys Met Asn Leu Gln Asp Asn Asn Gly Asn
            980                 985                 990

Asp Ile Gly Phe Ile Gly Phe His  Gln Phe Asn Asn Ile  Ala Lys Leu
```

Val Ala  Ser Asn Trp Tyr Asn Arg Gln Ile Glu Arg Ser Ser Arg
    1010              1015              1020

Thr Leu Gly Cys Ser Trp Glu Phe Ile Pro Val Asp Asp Gly Trp
    1025              1030              1035

Gly Glu Arg Pro Leu
    1040

<210> SEQ ID NO 29
<211> LENGTH: 3132
<212> TYPE: DNA
<213> ORGANISM: Artificial
<220> FEATURE:
<223> OTHER INFORMATION: coding sequence for recombinantly-created
      fusion protein LC-HC66/A comprising BoNT/A LC fused to HC66
<220> FEATURE:
<221> NAME/KEY: misc_feature
<222> LOCATION: (1)..(1314)
<223> OTHER INFORMATION: encode residues 1-438 of BoNT/A light chain
<220> FEATURE:
<221> NAME/KEY: misc_feature
<222> LOCATION: (1315)..(3132)
<223> OTHER INFORMATION: encode HC66; residues 692-1296 of BoNT/A heavy
      chain

<400> SEQUENCE: 29
atgccatttg ttaataaaca attcaactat aaagatcctg tcaacggcgt tgacattgca    60
tacatcaaga tccctaacgc aggccagatg cagccagtta aggctttcaa aattcacaat   120
aaaatctggg ttatcccgga acgtgacacc ttcaccaacc ctgaggaagg tgacctgaac   180
cctccgccgg aagccaaaca ggtgccagtc tcttattatg attctactta cctgtctacg   240
gataacgaga agacaactac cctgaaaggc gttacgaaac tgttcgagcg tatctactct   300
accgatctgg ccgtatgct gctgacctcc atcgtccgcg gcattccatt ctggggcggc   360
agcaccatcg ataccgaact gaaggtgatc gatactaact gtatcaacgt gattcagcca   420
gatggctctt accgttccga gaactgaac ctggttatca tcggtccgag cgcagacatc   480
atccaatttg aatgcaaatc cttcggtcac gaggtgctga acctgacgcg caacggctac   540
ggcagcactc aatatatccg tttctctccg gattttacgt ttggcttcga ggaatccctg   600
gaggttgata cgaacccact gctgggtgca ggtaaattcg ctactgaccc ggcggtgacg   660
ctggctcacg aactgattca tgcgggccat cgtctgtacg gcatcgcaat caacccgaac   720
cgcgttttta agtaaacac caacgcgtat tatgagatga gcggcctgga agtatccttc   780
gaagaactgc gtaccttcgg tggccacgac gcaaaattca tcgacagcct gcaagaaaac   840
gaattccgtc tgtactacta caataaattc aaagacattg cttccaccct gaacaaagcc   900
aaaagcatcg ttggtaccaa cgcctccctg cagtacatga aaaacgtgtt taaagaaaag   960
tacctgctgt ctgaagacac gagcggtaag ttctctgttg acaaactgaa attcgacaag  1020
ctgtacaaaa tgctgacgga aatctatacc gaggacaact tcgtgaaatt ctttaaagta  1080
ctgaaccgca aaacgtatct gaactttgac aaagcagttt tcaaaattaa catcgttccg  1140
aaagttaact acaccattta cgatggtttc aacctgcgta acactaatct ggcggcaaat  1200
ttcaacggcc agaacaccga atcaacaat atgaacttca ctaagcttaa aaacttcacc  1260
ggtctgttcg aattctataa actgctgtct gtgcgtggta ttattacgtc aaggtccag   1320 acgatcgaca acgcactgtc caagcgcaac gagaaatggg acgaagttta caatatatc  1380 gtaactaact ggctggcaaa agttaacact cagatcgacc tgattcgcaa aaagatgaag  1440
gaagctctgg aaaaccaagc cgaagcaacg aaggcgatta tcaactacca gtataaccag  1500

```
tacactgaag aagaaaagaa caacatcaac ttcaatatcg atgacctgtc tagcaaactg    1560
aacgagagca ttaacaaagc tatgatcaac attaacaaat tcctgaacca gtcctctgtc    1620
tcttacctga tgaacagcat gatcccgtac ggcgtgaaac gtctggaaga tttcgacgcg    1680
agcctgaaag acgccctgct gaaatacatc tacgacaacc gcggtactct gatcggccag    1740
gtggaccgcc tgaaagacaa ggtcaacaat actctgtcta ctgacatccc gtttcagctg    1800
agcaaatacg ttgataacca gcgcctgctg agcacgttta cggaatatat caaaaacatc    1860
atcaacacct ctattctgaa tctgcgctat gaatctaatc atctgatcga tctgagccgt    1920
tatgcgtcca aaatcaacat cggctccaaa gttaacttcg atccaatcga taagaatcaa    1980
attcagctgt ttaacctgga gtctagcaaa attgaagtta tcctgaaaaa cgcgattgta    2040
tacaattcca tgtatgaaaa tttctctacc tctttctgga ttcgcattcc gaaatatttc    2100
aatagcatct ccctgaacaa cgagtacacc atcattaact gcatggaaaa taactccggc    2160
tggaaagtgt ctctgaacta cggtgagatc atctggacgc tgcaggatac tcaggaaatc    2220
aaacagcgtg tggtgttcaa atattcccaa atgatcaaca tctccgatta catcaaccgt    2280 tggatttttcg tgaccattac caataaccgt ctgaacaaca gcaagatcta tattaacggt    2340
cgtctgatcg accagaaacc aattagcaat ctgggcaaca ttcatgcttc taacaatatc    2400
atgttcaaac tggatggctg ccgcgacact caccgttata tctggattaa gtatttcaat    2460
ctgttcgaca aggaactgaa cgaaaaggaa atcaaagatc tgtacgacaa ccagagcaac    2520
tccggcatcc tgaaagattt ctggggtgac tacctgcaat acgacaaacc gtactacatg    2580
ctgaatctgt acgaccctaa caagtacgta gatgtgaaca atgtgggtat ccgcggttac    2640
atgtacctga aggtccgcg cggttctgta atgactacca atatttaccta gaactcttct    2700 ctgtaccgtg gtactaagtt catcatcaaa aagtacgcga gcggcaacaa agacaatatc    2760
gttcgtaaca acgaccgcgt ctatattaac gtggtagtta aaaacaaaga ataccgcctg    2820
gctaccaacg cttcccaagc tggtgtggag aaaattctgt ccgcgctgga aattccggat    2880
gttggtaacc tgtctcaggt tgtagtgatg aagtctaaaa acgaccaggg tatcaccaat    2940
aaatgtaaaa tgaacctgca ggacaataac ggcaacgata ttggctttat cggcttccac    3000
cagttcaaca atattgctaa actggtagcg tccaactggt acaaccgtca gattgagcgt    3060
tcttcccgca ccctgggctg tagctgggaa ttcatccctg ttgacgacgg ctggggtgaa    3120
cgtcctctgt aa                                                        3132
```

<210> SEQ ID NO 30  
<211> LENGTH: 30  
<212> TYPE: DNA  
<213> ORGANISM: Artificial  
<220> FEATURE:  
<223> OTHER INFORMATION: chemically synthesized

<400> SEQUENCE: 30
ctggtgagcc agcgtcaccg ccgggtcagt     30

<210> SEQ ID NO 31  
<211> LENGTH: 30  
<212> TYPE: DNA  
<213> ORGANISM: Artificial  
<220> FEATURE:  
<223> OTHER INFORMATION: chemically synthesized

<400> SEQUENCE: 31
ctgagcaacc gtcagattga gcgttcttcc     30

<210> SEQ ID NO 32
<211> LENGTH: 1043
<212> TYPE: PRT
<213> ORGANISM: Artificial
<220> FEATURE:
<223> OTHER INFORMATION: recombinantly-created fusion protein tri-mutant
LC-HC66/A

<400> SEQUENCE: 32

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365
```

```
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Val Gln Thr Ile Asp Asn Ala Leu Ser Lys
        435                 440                 445
Arg Asn Glu Lys Trp Asp Glu Val Tyr Lys Tyr Ile Val Thr Asn Trp
    450                 455                 460
Leu Ala Lys Val Asn Thr Gln Ile Asp Leu Ile Arg Lys Lys Met Lys
465                 470                 475                 480
Glu Ala Leu Glu Asn Gln Ala Glu Ala Thr Lys Ala Ile Ile Asn Tyr
                485                 490                 495
Gln Tyr Asn Gln Tyr Thr Glu Glu Lys Asn Asn Ile Asn Phe Asn
            500                 505                 510
Ile Asp Asp Leu Ser Ser Lys Leu Asn Glu Ser Ile Asn Lys Ala Met
        515                 520                 525
Ile Asn Ile Asn Lys Phe Leu Asn Gln Cys Ser Val Ser Tyr Leu Met
    530                 535                 540
Asn Ser Met Ile Pro Tyr Gly Val Lys Arg Leu Glu Asp Phe Asp Ala
545                 550                 555                 560
Ser Leu Lys Asp Ala Leu Leu Lys Tyr Ile Tyr Asp Asn Arg Gly Thr
                565                 570                 575
Leu Ile Gly Gln Val Asp Arg Leu Lys Asp Lys Val Asn Asn Thr Leu
        580                 585                 590
Ser Thr Asp Ile Pro Phe Gln Leu Ser Lys Tyr Val Asp Asn Gln Arg
    595                 600                 605
Leu Leu Ser Thr Phe Thr Glu Tyr Ile Lys Asn Ile Ile Asn Thr Ser
610                 615                 620
Ile Leu Asn Leu Arg Tyr Glu Ser Asn His Leu Ile Asp Leu Ser Arg
625                 630                 635                 640
Tyr Ala Ser Lys Ile Asn Ile Gly Ser Lys Val Asn Phe Asp Pro Ile
                645                 650                 655
Asp Lys Asn Gln Ile Gln Leu Phe Asn Leu Glu Ser Ser Lys Ile Glu
            660                 665                 670
Val Ile Leu Lys Asn Ala Ile Val Tyr Asn Ser Met Tyr Glu Asn Phe
        675                 680                 685
Ser Thr Ser Phe Trp Ile Arg Ile Pro Lys Tyr Phe Asn Ser Ile Ser
    690                 695                 700
Leu Asn Asn Glu Tyr Thr Ile Ile Asn Cys Met Glu Asn Asn Ser Gly
705                 710                 715                 720
Trp Lys Val Ser Leu Asn Tyr Gly Glu Ile Ile Trp Thr Leu Gln Asp
                725                 730                 735
Thr Gln Glu Ile Lys Gln Arg Val Val Phe Lys Tyr Ser Gln Met Ile
            740                 745                 750
Asn Ile Ser Asp Tyr Ile Asn Arg Trp Ile Phe Val Thr Ile Thr Asn
        755                 760                 765
Asn Arg Leu Asn Asn Ser Lys Ile Tyr Ile Asn Gly Arg Leu Ile Asp
    770                 775                 780
Gln Lys Pro Ile Ser Asn Leu Gly Asn Ile His Ala Ser Asn Asn Ile
```

-continued

```
785                 790                 795                 800

Met Phe Lys Leu Asp Gly Cys Arg Asp Thr His Arg Tyr Ile Trp Ile
                805                 810                 815

Lys Tyr Phe Asn Leu Phe Asp Lys Glu Leu Asn Glu Lys Glu Ile Lys
            820                 825                 830

Asp Leu Tyr Asp Asn Gln Ser Asn Ser Gly Ile Leu Lys Asp Phe Trp
        835                 840                 845

Gly Asp Tyr Leu Gln Tyr Asp Lys Pro Tyr Tyr Met Leu Asn Leu Tyr
    850                 855                 860

Asp Pro Asn Lys Tyr Val Asp Val Asn Asn Val Gly Ile Arg Gly Tyr
865                 870                 875                 880
Met Tyr Leu Lys Gly Pro Arg Gly Ser Val Met Thr Thr Asn Ile Tyr
                885                 890                 895

Leu Asn Ser Ser Leu Tyr Arg Gly Thr Lys Phe Ile Ile Lys Lys Tyr
            900                 905                 910

Ala Ser Gly Asn Lys Asp Asn Ile Val Arg Asn Asn Asp Arg Val Tyr
        915                 920                 925

Ile Asn Val Val Val Lys Asn Lys Glu Tyr Arg Leu Ala Thr Asn Ala
    930                 935                 940

Ser Gln Ala Gly Val Glu Lys Ile Leu Ser Ala Leu Glu Ile Pro Asp
945                 950                 955                 960
Val Gly Asn Leu Ser Gln Val Val Val Met Lys Ser Lys Asn Asp Gln
                965                 970                 975

Gly Ile Thr Asn Lys Cys Lys Met Asn Leu Gln Asp Asn Asn Gly Asn
            980                 985                 990

Asp Ile Gly Phe Ile Gly Phe His  Gln Phe Asn Asn Ile  Ala Lys Leu
        995                 1000                1005

Val Ala  Ser Asn Leu Ser Asn  Arg Gln Ile Glu Arg  Ser Ser Arg
    1010                1015                1020

Thr Leu  Gly Cys Ser Trp Glu  Phe Ile Pro Val Asp  Asp Gly Trp
    1025                1030                1035

Gly Glu  Arg Pro Leu
    1040

<210> SEQ ID NO 33
<211> LENGTH: 3132
<212> TYPE: DNA
<213> ORGANISM: Artificial
<220> FEATURE:
<223> OTHER INFORMATION: coding sequence for recombinantly-created
      fusion protein tri-mutant LC-HC66/A

<400> SEQUENCE: 33
atgccatttg ttaataaaca attcaactat aaagatcctg tcaacggcgt tgacattgca     60
tacatcaaga tccctaacgc aggccagatg cagccagtta aggctttcaa aattcacaat    120
aaaatctggg ttatcccgga acgtgacacc ttcaccaacc ctgaggaagg tgacctgaac    180
cctccgccgg aagccaaaca ggtgccagtc tcttattatg attctactta cctgtctacg    240
gataacgaga aagacaacta cctgaaaggc gttacgaaac tgttcgagcg tatctactct    300
accgatctgg gccgtatgct gctgacctcc atcgtccgcg gcattccatt ctggggcggc    360
agcaccatcg ataccgaact gaaggtgatc gatactaact gtatcaacgt gattcagcca    420
gatggctctt accgttccga agaactgaac ctggttatca tcggtccgag cgcagacatc    480
atccaatttg aatgcaaatc cttcggtcac gaggtgctga acctgacgcg caacggctac    540
ggcagcactc aatatatccg tttctctccg gattttacgt ttggcttcga ggaatccctg    600
```

```
gaggttgata cgaacccact gctgggtgca ggtaaattcg ctactgaccc ggcggtgacg    660
ctggctcacc agctgattca tgcgggccat cgtctgtacg gcatcgcaat caaccctaac    720
cgcgttttta agtaaacac  caacgcgtat tatgagatga gcggcctgga agtatccttc    780
gaagaactgc gtaccttcgg tggccacgac gcaaaattca tcgacagcct gcaagaaaac    840
gaattccgtc tgtactacta caataaattc aaagacattg cttccaccct gaacaaagcc    900
aaaagcatcg ttggtaccac cgcctccctg cagtacatga aaaacgtgtt taagaaaag     960 tacctgctgt ctgaagacac gagcggtaag ttctctgttg acaaactgaa attcgacaag   1020
ctgtacaaaa tgctgacgga atctatacc  gaggacaact tcgtgaaatt ctttaaagta   1080
ctgaaccgca aaacgtatct gaactttgac aaagcagttt tcaaaattaa catcgttccg   1140
aaagttaact acaccattta cgatggtttc aacctgcgta acactaatct ggcggcaaat   1200
ttcaacggcc agaacaccga atcaacaat  atgaacttca ctaagcttaa aaacttcacc   1260
ggtctgttcg aattctataa actgctgtct gtgcgtggta ttattacgtc caaggtccag   1320
acgatcgaca acgcactgtc caagcgcaac gagaaatggg acgaagttta caaatatatc   1380
gtaactaact ggctggcaaa agttaacact cagatcgacc tgattcgcaa aaagatgaag   1440
gaagctctgg aaaaccaagc cgaagcaacg aaggcgatta tcaactacca gtataaccag   1500
tacactgaag aagaaaagaa caacatcaac ttcaatatcg atgacctgtc tagcaaactg   1560
aacgagagca ttaacaaagc tatgatcaac attaacaaat tcctgaacca gtcctctgtc   1620
tcttacctga tgaacagcat gatcccgtac ggcgtgaaac gtctggaaga tttcgacgcg   1680
agcctgaaag acgccctgct gaaatacatc tacgacaacc gcggtactct gatcggccag   1740
gtggaccgcc tgaaagacaa ggtcaacaat actctgtcta ctgacatccc gtttcagctg   1800
agcaaatacg ttgataacca gcgcctgctg agcacgttta cggaatatat caaaaacatc   1860
atcaacacct ctattctgaa tctgcgctat gaatctaatc atctgatcga tctgagccgt   1920
tatgcgtcca aaatcaacat cggctccaaa gttaacttcg atccaatcga taagaatcaa   1980
attcagctgt ttaacctgga gtctagcaaa attgaagtta tcctgaaaaa cgcgattgta   2040
tacaattcca tgtatgaaaa tttctctacc tctttctgga ttcgcattcc gaaatatttc   2100
aatagcatct ccctgaacaa cgagtacacc atcattaact gcatggaaaa taactccggc   2160
tggaaagtgt ctctgaacta cggtgagatc atctggacgc tgcaggatac tcaggaaatc   2220
aaacagcgtg tggtgttcaa atattcccaa atgatcaaca tctccgatta tcatcaaccgt   2280 tggattttcg tgaccattac caataaccgt ctgaacaaca gcaagatcta tattaacggt   2340
cgtctgatcg accagaaacc aattagcaat ctgggcaaca ttcatgcttc taacaatatc   2400
atgttcaaac tggatggctg ccgcgacact caccgttata tctggattaa gtatttcaat   2460
ctgttcgaca aggaactgaa cgaaaaggaa atcaaagatc tgtacgacaa ccagagcaac   2520
tccggcatcc tgaaagattt ctggggtgac tacctgcaat acgacaaacc gtactacatg   2580
ctgaatctgt acgaccctaa caagtacgta gatgtgaaca atgtgggtat ccgcggttac   2640
atgtacctga aaggtccgcg cggttctgta atgactacca atatttacct gaactcttct   2700
ctgtaccgtg gtactaagtt catcatcaaa aagtacgcga gcggcaacaa agacaatatc   2760
gttcgtaaca acgaccgcgt ctatattaac gtggtagtta aaaacaaaga ataccgcctg   2820
gctaccaacg cttcccaagc tggtgtggag aaaattctgt ccgcgctgga aattccggat   2880
gttggtaacc tgtctcaggt tgtagtgatg aagtctaaaa acgaccaggg tatcaccaat   2940
aaatgtaaaa tgaacctgca ggacaataac ggcaacgata ttggctttat cggcttccac   3000
```

-continued

```
cagttcaaca atattgctaa actggtagcg tccaacctga gcaaccgtca gattgagcgt    3060
tcttcccgca ccctgggctg tagctgggaa ttcatccctg ttgacgacgg ctggggtgaa    3120
cgtcctctgt aa                                                        3132
```

US 8,445,650 B2

MUTANT BOTULINUM NEUROTOXIN SEROTYPE A POLYPEPTIDE AND USES THEREOF

FIELD OF THE INVENTION

The invention relates to botulinum neurotoxin polypeptides, particularly serotype A botulinum neurotoxin polypeptides, and their use.

BACKGROUND OF THE INVENTION

Botulinum toxin (BoNT) is a microbial protein that causes a potentially fatal neuroparalytic disease called botulism. The disease can occur in several different variants, but the most common is oral poisoning. Patients can ingest food that is contaminated with preformed toxin (primary infection), or they can ingest food contaminated with organisms that manufacture toxin in situ (primary infection with secondary intoxication). In both cases, the toxin progresses through two essential sequences of events to produce its adverse effects.

During the first sequence of events, BoNT is absorbed into the body. More precisely, the toxin binds to the apical surface of epithelial cells in the gut (viz., transport cells). This is followed by receptor-mediated endocytosis, transcytosis, and eventual release of unmodified toxin into the general circulation. The toxin is distributed throughout the periphery, where it binds with high affinity to the junctional region of cholinergic nerve endings (viz., target cells). This initiates the second sequence of events, which includes receptor-mediated endocytosis, pH-induced translocation to the cytosol, and enzymatic cleavage of polypeptides that govern transmitter release. Cleavage of these substrates, with the resulting blockade in transmitter exocytosis, produces the neuroparalytic outcome that is characteristic of the disease botulism.

BoNT is synthesized as a single-chain inactive propolypeptide having a molecular mass of approximately 150 kilodaltons. Inactive pro-BoNT is activated by proteolytic cleavage of the pro-BoNT by endogenous or exogenous proteases. Cleavage ("nicking") of the inactive BoNT propeptide yields two polypeptide chains, a heavy chain ("HC") and a light chain ("LC"). The HC and LC normally remain linked by a disulfide bond that can be severed under reducing conditions, such as those that exist in the interior of an animal cell.

Recent studies have demonstrated that: (a) the BoNT molecule possesses the ligand properties that account for binding to epithelial cells; auxiliary proteins that are associated with the toxin are not essential for binding; (b) the entire light chain and the aminoterminal portion of the heavy chain can be removed from the holotoxin, and the residual about 50 kDa carboxyterminal portion of the heavy chain (HC50) retains the ability to cross epithelial barriers, and (c) both the holotoxin and the HC50 domain cross epithelial monolayers without any change in their characteristic structures and biological activities (Maksymowych et al., *Infect. Immun.* 67:4708-4712, 1999; Maksymowych et al., *J. Biol. Chem.* 273:21950-21957, 1998; Maksymowych et al., *J. Pharmacol. Exp. Ther.* 310:633-641, 2004). Thus, the BoNT heavy chain, and the HC50 domain in particular, have been proposed as an antigen in developing a mucosal vaccine against botulinum toxin and also as a delivery vehicle in transporting entities across epithelial barrier. See US Patent Publication 2004/0013687 A1 (2004).

The three-dimensional structure of BoNT serotype A (BoNT/A) has been determined (Lacy et al., *Nature Struct. Biol.* 5:898-902, 1998; Lacy et al., *J. Mol. Biol.* 291:1091-1104, 1999). The toxin molecule is composed of three somewhat independent lobes that represent the light chain (ca. 50 kDa), the aminoterminal portion of the heavy chain (ca. 50 kDa), and the carboxyterminal portion of the heavy chain (ca. 50 kDa). It is the third lobe that plays a key role in binding to nerve terminals, and it is this portion of the molecule that displays affinity for gangliosides. Certain single point mutations in the BoNT/A carboxyterminal portion have been shown to diminish, but not completely abrogate, binding to nerve-membrane preparations (Rummel et al., *Mol. Microbiol.* 51:631-643, 2004).

When administered by injection, BoNT HC50 polypeptides evoke a robust IgG response (Byrne et al., *Biochimie* 82:955-966, 2000). While BoNT/A HC50 evokes an immune response, it also carries a potential risk. The HC50 domain can bind and enter nerve endings (Lalli et al., *J. Cell Sci.* 112:2715-2724, 1999). Clearly, this is not a desirable characteristic of a vaccine candidate, nor of a delivery vehicle for transporting chemical entities across epithelial membranes. Therefore, alterations in the HC50 domain of BoNT/A HC polypeptides that abolish neuronal binding but that do not abolish epithelial transport or immunogenicity would represent a substantial advance.

What is needed is a BoNT-based polypeptide, particularly a BoNT/A-based polypeptide, which may be safely employed as a botulinum vaccine or a transmucosal carrier for delivery of therapeutic or diagnostic agents to mammals, without neurotoxicity to the subject. In particular, what is needed is a BoNT-based polypeptide that has been engineered to lose its affinity for polysialogangliosides and nerve endings, but retains its affinity for epithelial cells.

SUMMARY OF THE INVENTION

According to one embodiment of the invention, a modified BoNT/A polypeptide is provided, comprising:
  an isolated BoNT/A heavy chain polypeptide,
  a fragment of a BoNT/A heavy chain polypeptide comprising at least about 20% of the molecular mass of said heavy chain polypeptide and containing the ganglioside binding motif Ser-X-Trp-Tyr, or
  a fusion polypeptide comprising said BoNT/A heavy chain polypeptide fragment and a non-BoNT/A heavy chain polypeptide,
wherein the modified polypeptide contains the double mutation Trp-Tyr→Leu-Ser in said ganglioside binding motif.

In some embodiments, the modified BoNT/A polypeptide comprises at least about 30% of the molecular mass of BoNT/A heavy chain. In other embodiments, the modified BoNT/A polypeptide comprises at least about 50% of the molecular mass of BoNT/A heavy chain.

In some embodiments of the invention, the modified BoNT/A polypeptide is a carboxyterminal fragment of the BoNT/A heavy chain. The carboxyterminal fragment may comprise, for example, an about 50 kDa, an about 66 kDa, or an about 88 carboxyterminal fragment of the BoNT/A heavy chain. In one embodiment, the modified BoNT/A polypeptide comprises or consists of the amino acid sequence SEQ ID NO:14.

According to another embodiment of the invention, a nucleic acid is provided encoding a modified BoNT/A polypeptide. The modified BoNT/A polypeptide comprises:
  an isolated BoNT/A heavy chain polypeptide,
  a fragment of a BoNT/A heavy chain polypeptide comprising at least about 20% of the molecular mass of said heavy chain polypeptide and containing the ganglioside binding motif Ser-X-Trp-Tyr, or a fusion polypeptide comprising said BoNT/A heavy chain polypeptide fragment and a non-BoNT/A heavy chain polypeptide, wherein the modified polypeptide contains the double mutation Trp-Tyr→Leu-Ser in said ganglioside binding motif.

In some embodiments, the nucleic acid encodes such a modified BoNT/A polypeptide comprising at least about 30% of the molecular mass of BoNT/A heavy chain, or at least about 50% of the molecular mass of BoNT/A heavy chain. In some embodiments, the nucleic acid encodes a carboxyterminal fragment of the aforesaid modified BoNT/A heavy chain polypeptide, for example a fragment comprising an about 50 kDa, an about 66 kDa, or an about 88 carboxyterminal fragment of the BoNT/A heavy chain. In one embodiment, the nucleic acid encodes a modified BoNT/A polypeptide comprising or consisting of the nucleic acid sequence SEQ ID NO:13. According to one embodiment, the nucleic acid consists of SEQ ID NO:13.

According to another embodiment of the invention, an expression vector is provided comprising a nucleic acid sequence as above, and a host cell transfected with such an expression vector is also provided. The host cell may comprise, for example, a prokaryotic cell. Alternatively, the host cell may comprise a eukaryotic cell.

In yet another embodiment of the invention, a method of preparing the aforementioned modified BoNT/A polypeptide is provided, comprising culturing a transfected host cell, as described above, under conditions wherein the modified BONT/A polypeptide is expressed.

Compositions are provided comprising the modified BoNT/A polypeptide and a pharmaceutically acceptable carrier. The compositions are immunogenic in that they are capable of inducing an immune response to BoNT/A in animals, particularly humans, when the compositions are administered. The compositions therefore have utility as vaccines against the effects of BoNT/A.

In other embodiments, methods of inducing an immune response to BONT/A in an animal, and methods for protecting, i.e. vaccinating, an animal from botulism caused by BoNT/A are provided. The methods comprise administering to an animal in need of such treatment an effective amount of the aforesaid immunogenic composition comprising a modified BoNT/A polypeptide of the invention.

A conjugate is also provided comprising a modified BoNT/A polypeptide as described above, linked to a diagnostic or therapeutic entity. Methods of delivering a diagnostic or therapeutic entity and methods of inducing an immune response are provided. The methods comprise contacting an epithelium of an animal or vertebrate with the aforesaid conjugate.

These and other embodiments and objects of the invention are apparent from the following non-limiting description of the invention. It should be understood, however, that the invention is not limited to the precise arrangements, sequences, compounds, and instrumentalities shown.

DEFINITIONS

Figure 1:
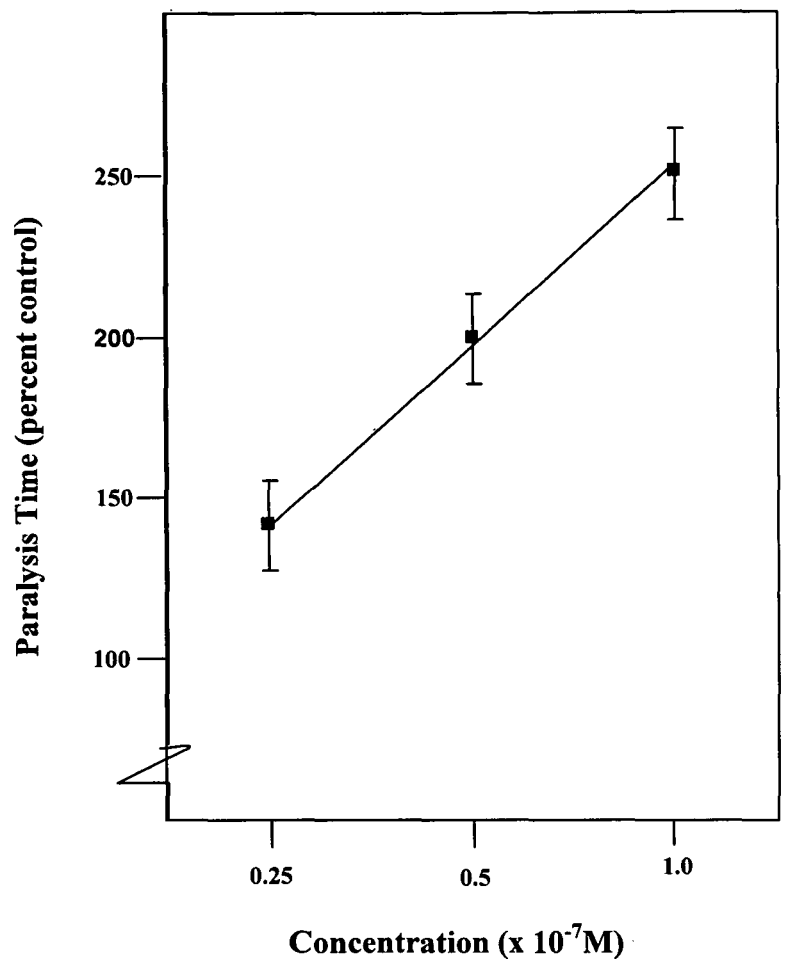
FIG. 1 is a plot of the concentration of wild type BoNT/A HC50 against paralysis time in murine phrenic nerve-hemidiaphragm preparations. The preparations were incubated with BoNT/A and with various concentrations of BoNT/A HC50 domain (N=3 or more per data point). The average paralysis times of tissues treated with toxin alone was 146+13 min. In the presence of ca. $5 \times 10^{-8}$ M BoNT/A HC50 polypeptide, the paralysis times of tissues increased approximately 2-fold.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "animal" has its ordinary meaning, and is meant to include human beings.

"Plurality" means at least two.

By "BoNT/A" is meant the botulinum neurotoxin serotype A, including all variations thereof. Wild-type BoNT/A is synthesized as an inactive propolypeptide that comprises 1296 amino acid residues. The BoNT/A amino acid residue numbering used herein refers to the BoNT propolypeptide amino acid sequence.

By "HC" is meant the BoNT heavy chain.

By "BoNT/A HC polypeptide" is meant the full-length heavy chain of BoNT/A, including all variants thereof. The wild-type BoNT/A HC polypeptide consists of an 846 amino acid sequence that corresponds to amino acids 451 to 1296 of the BoNT/A propolypeptide amino acid sequence. Variants may be naturally-occurring variants, such as SEQ ID NO:9, SEQ ID NO:10, SEQ ID NO:11, SEQ ID NO:12, SEQ ID NO:21, SEQ ID NO:23 and SEQ ID No:25, as well as recombinantly created variants. The term "BoNT/A HC polypeptide" further embraces polypeptides containing at least about 95% sequence identity to SEQ ID NO:9, SEQ ID NO:10, SEQ ID NO:11, SEQ ID NO:12, SEQ ID NO:21, SEQ ID NO:23 or SEQ ID No:25.

By "HC50" is meant the about 50 kDa carboxyterminal fragment of the BoNT heavy chain. HC50 of BoNT/A corresponds to about residues 861 to 1296 of the BoNT/A propolypeptide amino acid sequence. The N-terminus of HC50 of BoNT/A may correspond to about residue 850 to about residue 865 of the BoNT/A propolypeptide sequence. Similarly, by "HC88" and "HC66" are meant, respectively, the about 88 kDa and about 66 kDa carboxyterminal fragments of BoNT heavy chain. By "carboxyterminal fragment" is meant a fragment of a parent polypeptide substantially encompassing the carboxyterminal end of the parent polypeptide. By "substantially encompassing the carboxyterminal end" is meant no more than about five, preferably no more than about three amino acids, and most preferably, no amino acids are truncated from the carboxyterminal end of the parent polypeptide.

As used here, "ganglioside binding motif" refers to the amino acid sequence Ser-X-Trp-Tyr in the C-terminal half of the HC of BoNT/A. In the BoNT/A propolypeptide, this four amino acid sequence corresponds to residues 1264 to 1267. As the skilled artisan will readily recognize, the residue numbers for the motif will be different in a fragment which has N-terminal residues deleted. For instance, in the context of the 846 amino acid BoNT/A HC polypeptide, the ganglioside binding motif corresponds to residues 814 to 817.

By "conjugate" is meant a substance formed by two or more entities linked to one another by any physiochemical means, including, but not limited to, hydrophobic interaction, covalent interaction, hydrogen bond interaction, or ionic interaction.

By "therapeutic entity" is meant any substance administrable to a vertebrate subject to induce a therapeutic or prophylactic result in the subject upon administration. As used herein, a non-limiting example of a therapeutic entity is an immunogenic entity. Thus, an entity that is capable of inducing an immune response in the intended recipient is a therapeutic entity. Accordingly, a prophylactic result encompasses the induction of an immune response, such as a protective response.

By "diagnostic entity" is meant any substance administrable to a vertebrate subject to induce a diagnostic result in the subject upon administration or any substance used in in vivo, ex vivo or in vitro procedures to induce an imaging result. As used herein, a diagnostic entity includes imaging agents, labeling agents, contrast agents and the like, which may be used in diagnostic procedures, as well as research protocols which do not have diagnostic intent.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Immunogenic composition" refers to a composition comprising an antigen wherein the composition is capable of inducing an immune response to the antigen in an immunocompetent host. The immune response induced may or may not be a protective immune response. An immunogenic composition that induces a protective immune response is useful in vaccination protocols.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "polypeptide" typically refers to large polypeptides.

It will be appreciated, of course, that the polypeptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the polypeptide may include one or more D-amino acid resides, or may comprise amino acids which are all in the D-form. Retro-inverso forms of polypeptides in accordance with the present invention are also contemplated, for example, inverted peptides in which all amino acids are substituted with D-amino acid forms.

Acid addition salts of the present invention are also contemplated as functional equivalents. Thus, a polypeptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

The term "peptide" typically refers to short polypeptides and may comprise a modification as described for polypeptides.

As used herein, the term "fusion protein" or "fusion polypeptide" refers to a polypeptide which contains peptide regions from at least two different proteins, or different regions of the same peptide, which are not normally juxtaposed. Thus, a fusion protein of a modified BoNT/A HC polypeptides of the invention embraces the combination of such a peptide fused to a non-BoNT/A HC polypeptide, or a BoNT/A HC polypeptide linked to another BoNT/A HC polypeptide.

Conventional notation is used herein to portray polypeptide sequences: the left-hand end of a polypeptide sequence is the amino-terminus; the right-hand end of a polypeptide sequence is the carboxyl-terminus.

DETAILED DESCRIPTION OF THE INVENTION

According to the present invention, introduction of the double mutation Trp-Tyr→Leu-Ser in the ganglioside binding motif in a BoNT/A heavy chain (HC) polypeptide to provide a modified polypeptide results in the loss of any meaningful ability of the molecule to bind nerve endings. This is in contrast to the corresponding single mutants Trp→Leu and Tyr→Ser, which display incomplete losses of nerve binding affinity. BoNT/A HC polypeptides modified to contain the Trp→Leu and Tyr→Ser double mutant in the ganglioside binding motif also retain substantial ability to cross epithelial barriers. The ability to cross epithelial barriers is in the same range of the corresponding homologous unmutated BoNT/A HC polypeptide. The modified BoNT/A HC polypeptides of the invention which contain the Trp-Tyr→Leu-Ser double mutation in the ganglioside binding motif are thus suitable as vaccines against botulinum toxin, whether administered by the injection route or by the mucosal route, and whether administered alone or with adjuvant. Antiserum that results from the immunization with the modified BoNT/A HC polypeptides of the invention retains the ability to bind to native BoNT/A toxin and block its association with nerve endings. This is one of the characteristic properties of antiserum that results from immunization with the native proteins. The dimutated BoNT/A HC polypeptides of the invention thus possesses the desirable properties of native domains, including the abilities to evoke an immune response and resistance after administration. On the other hand, the dimutated BoNT/A HC polypeptides of the invention do not possess the undesirable property of binding and entering nerve cells.

In addition to utility as vaccines against botulinum toxin, the modified BoNT/A HC polypeptides of the invention, by virtue of their ability to cross epithelial membranes, are useful as delivery vehicles for the delivery of therapeutic or diagnostic entities by administration routes that rely on translocation across epithelial membranes. The modified BoNT/A HC polypeptides are therefore useful in forming conjugates with such entities for administration.

The modified BoNT/A HC polypeptide for use as a vaccine, or for use as a delivery vehicle for diagnostic or therapeutic entities, can comprise an isolated BoNT/A heavy chain polypeptide, free of the BoNT/A light chain. Alternatively, the modified BoNT/A HC polypeptide may take the form of a fragment of the BoNT/A HC comprising at least about 20% of the molecular mass of the HC, but containing the ganglioside binding motif which, in its unmutated form, is Ser-X-Trp-Tyr. In naturally-occurring BoNT alleles, X is generally a relatively polar amino acid, such as Asn, Gln, Thr and Ser. In either case, the modified BoNT/A HC polypeptide contains the double mutation Trp-Tyr→Leu-Ser in the ganglioside binding motif. Where a fragment of BoNT/A HC is used a vaccine against botulinum intoxication, the fragment should be immunogenic, i.e., capable of inducing an immune response in an immunocompetent host. It should be appreciated, however, that when the fragment is linked to an entity comprising an immunogenic portion of BoNT, the fragment itself need not be immunogenic, as the entity triggers the immune response to the toxin. For use as a vaccine, the modified BoNT/A HC polypeptide may also take the form of a fusion polypeptide which comprises a fragment of the BoNT/A heavy chain comprising at least about 20% of the molecular mass of the HC and contains the ganglioside binding domain linked to a non-BoNT/A heavy chain polypeptide. The non-BoNT/A HC polypeptide may comprise, for example, an adjuvant polypeptide, e.g., the Cholera toxin B subunit. In one embodiment, the BoNT/A HC polypeptide comprises a BoNT light chain, resulting in a vaccine which contains a BoNT light chain linked to a BoNT/A HC fragment containing the ganglioside binding motif mutation Trp-Tyr→Leu-Ser. Preferably, the BoNT light chain contains at least one mutation that reduces or eliminates the catalytic activity of the light chain. Exemplary mutations in the zinc-binding motif of the light chain are described, for instance, in U.S. Pat. No. 6,051,239. In one embodiment, the LC is fused to a modified HC66 of the invention. In one aspect, the LC is from a BoNT/A and Glu224 is mutated, for instance, to Gln, and is fused to a modified HC66 from a BoNT/A.

At least seven naturally-occurring variants of the BoNT/A HC polypeptide are known. The ganglioside binding motif corresponds to residues 814 to 817 in the BoNT/A HC polypeptide. Any naturally-occurring variant may be used as the basis of the modified BoNT/A HC polypeptide according to the present invention. Such variants include SEQ ID NO:9, SEQ ID NO:10, SEQ ID NO:11, SEQ ID NO:12, SEQ ID NO:21, SEQ ID NO:23, and SEQ ID NO:25. The aforementioned BoNT/A HC polypeptides are encoded, for example, by the nucleotide sequences SEQ ID NO:15, SEQ ID NO:16, SEQ ID NO:17, SEQ ID NO:18, SEQ ID NO:22, SEQ ID NO:24 and SEQ ID NO:26, respectively.

In some embodiments of the invention, the modified BoNT/A HC polypeptide comprises or consists of a fragment of the BoNT/A HC comprising at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the molecular mass of the HC, but contains the ganglioside binding motif. Similarly, the invention extends to nucleic acid molecules encoding the aforementioned polypeptides. The invention also extends to expression vectors comprising such nucleic acid molecules, as well as to host cells transfected with such an expression vector.

In some embodiments, the modified BoNT/A HC polypeptide of the invention comprises or consists of a carboxyterminal fragment of the BoNT/A HC. Non-limiting examples include HC50, HC66 and HC88. They may be prepared by inserting the Trp-Tyr→Leu-Ser double mutation into the appropriate sized carboxyterminal fragment of BoNT/A HC, for example the BoNT/A HC of SEQ ID NO:9, which is encoded by the nucleic acid SEQ ID NO:15. The resulting modified carboxyterminal fragment containing the double mutation is represented by, for example, SEQ ID NO:14 (dimutant HC50), SEQ ID NO:19 (dimutant HC66) and SEQ ID NO:20 (dimutant HC88). Similarly, the invention extends to nucleic acid molecules encoding the aforementioned carboxyterminal fragment of the BoNT/A HC. In one embodiment, the nucleic acid encodes the polypeptide consisting of amino acid sequence SEQ ID NO:14. In one embodiment, the nucleic acid consists of the nucleotide sequence SEQ ID NO:13. The invention also extends to expression vectors comprising such nucleic acid molecules, as well as to host cells transfected with such an expression vector.

The scope of the modified BoNT/A HC polypeptides of the invention further extends to polypeptides derived from any of the aforementioned BoNT/A HC polypeptides that not only contain the double mutation Trp-Tyr→Leu-Ser in the ganglioside binding motif, but may further include other substitutions, deletions or insertions in the BoNT/A HC amino acid sequence, including the Ser-X residues of the ganglioside binding motif. Accordingly, the term "BoNT/A HC polypeptide" embraces polypeptides containing at least about 95% sequence identity to SEQ ID NO:9, SEQ ID NO:10, SEQ ID NO:11, SEQ ID NO:12, SEQ ID NO:21, SEQ ID NO:23, or SEQ ID NO:25, excluding the double mutation Trp-Tyr→Leu-Ser in the ganglioside binding motif.

The determination of percent sequence identity between two nucleotide or amino acid sequences can be accomplished using a mathematical algorithm. For example, a mathematical algorithm useful for comparing two sequences is the algorithm of Karlin and Altschul, 1990, *Proc. Natl. Acad. Sci. USA* 87:2264-2268, modified as in Karlin and Altschul (1993), *Proc. Natl. Acad. Sci. USA* 90:5873-5877). This algorithm is incorporated into the NBLAST and XBLAST programs of Altschul, et al. (1990) *J. Mol. Biol.* 215:403-410, and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997), *Nucleic Acids Res.* 25:3389-3402. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The further modifications beyond the double mutation Trp-Tyr→Leu-Ser in the ganglioside binding motif desirably do not affect either the ability of the molecule to induce an immune protective response against BoNT A, particularly where the polypeptide is used as a vaccine against botulinum intoxication. Further, the modifications desirably do not adversely affect the ability of the molecule to traverse epithelial barriers. The further mutations may be selected from substitutions, insertions or deletions into a wild-type BoNT/A HC amino acid. Preferably, the BoNT/A HC polypeptide from which the modified BoNT/A HC polypeptides of the invention are derived contain at least about 96%, at least about 97%, at least about 98%, or at least about 99%, sequence identity with respect to SEQ ID NO:9, SEQ ID NO:10, SEQ ID NO:11, SEQ ID NO:12, SEQ ID NO:21, SEQ ID NO:23, or SEQ ID NO:25.

The modified BoNT/A HC polypeptides of the present invention may be prepared by substituting the codons of the wild-type nucleotide sequence encoding the Trp-Tyr sequence of the ganglioside binding motif Ser-X-Trp-Tyr with codons encoding the sequence Leu-Ser. There are six codons that specify Leu, and there are six codons that specify Ser. Any of these codons may be used in any combination to prepare the Trp-Tyr to Leu-Ser mutation. Coding sequences for a modified BoNT/A HC polypeptide of the invention may be codon optimized based on the codon usage of the intended host cell in order to improve expression efficiency. Codon usage patterns can be found in the literature (Nakamura et al., 2000, Nuc Acids Res. 28:292). The introduction of other modifications may be achieved in the same manner. The construction of such mutant polynucleotides may be carried out by well-known site-directed mutagenesis methods, for instance, using the appropriate primer sets. The mutated nucleotide sequence may be cloned into a suitable expression vector which is then transfected into a suitable host. The transfected host cell is then cultured under conditions wherein the mutated nucleotide sequence is expressed.

In brief summary, the expression of natural or synthetic nucleic acids encoding a modified BoNT/A polypeptide is typically achieved by operably linking a nucleic acid encoding the modified BoNT/A polypeptide to a promoter, and incorporating the construct into an expression vector. The vectors are suitable for replication and integration in prokaryotes, eukaryotes, or both. Typical cloning vectors contain transcription and translation terminators, initiation sequences, and promoters useful for regulation of the expression of the desired nucleic acid sequence.

The nucleic acid can be cloned into a number of types of vectors. However, the present invention should not be construed to be limited to any particular vector. Instead, the present invention should be construed to encompass a wide plethora of vectors which are readily available and/or well-known in the art. For example, an the nucleic acid of the invention can be cloned into a vector including, but not limited to a plasmid, a phagemid, a phage derivative, an animal virus, and a cosmid.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

The expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in Ausubel et al. (2005, Current Protocols in Molecular Biology, John Wiley & Sons, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326, 193).

In the context of an expression vector, the vector can be readily introduced into a host cell, e.g., mammalian, bacterial, yeast or insect cell by any method in the art. Representative examples of appropriate hosts include bacterial cells, such as streptococci, staphylococci, *Escherichia coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells. In one embodiment, the expression vector is a plasmid and the host cell is *Escherichia coli*. The expression vector can be transferred into a host cell by physical, biological or chemical means.

Physical methods for introducing a polynucleotide into a host cell include calcium phosphate precipitation, lipofection, particle bombardment, microinjection, electroporation, photoporation, and the like. Methods for producing cells comprising vectors and/or exogenous nucleic acids are well-known in the art. See, for example, Sambrook et al. (2001, supra), and in Ausubel et al. (2005, supra).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

The polypeptides may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes. Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. Examples of solid phase peptide synthesis methods include the BOC method which utilized tert-butyloxycarbonyl as the α-amino protecting group, and the FMOC method which utilizes 9-fluorenylmethyloxycarbonyl to protect the α-amino of the amino acid residues, both which methods are well-known by those of skill in the art To ensure that the polypeptide obtained from biological or chemical synthetic techniques is the desired polypeptide, analysis of the peptide composition can be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use in a method of the invention, the modified BoNT/A polypeptide can be purified to remove contaminants. In this regard, it will be appreciated that the polypeptide can be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

In preparing a substantially pure polypeptide, an immunological, enzymatic or other assay can be used to monitor purification at each stage in the procedure. Protein purification methods are well known in the art, and are described, for example in Deutscher et al. (ed., 1990, Guide to Protein Purification, Harcourt Brace Jovanovich, San Diego, Calif.).

Any modifications to the BoNT/A HC polypeptides beyond the above-described double mutation in the ganglioside binding motif should also preserve the non-toxicity of the molecule. For the purposes of this invention, by "nontoxic" it is meant that exposure of the cholinergic nerve endings to the modified BoNT/A HC polypeptide does not result in blockade of transmitter release in the nerve endings and paralysis. In particular, the modifications should not result in the undesirable property of the BoNT/A HC polypeptide binding to and entering nerve cells. The effects amino acid sequence alternations on the desirable properties of nontoxicity, freedom from binding to and entrance into nerve cells, and ability to traverse epithelial barriers, can be routinely performed in accordance with the teachings provided herein and elsewhere. One of ordinary skill in the art may thus identify modifications that preserve the desired properties of the dimutant BoNT/A HC polypeptides of the invention.

The toxicity of modified BoNT/A HC polypeptides may be tested either in vitro or in vivo, for example, according to the procedure of U.S. Pat. No. 6,051,239. Briefly polypeptide is diluted in phosphate buffered saline (PBS) including 1 mg/ml bovine serum albumin (BSA) and injected intraperitoneally (i.p.) into mice. The polypeptide is administered in a 100 μl aliquot of PBS-BSA at a concentration of 10 μg per animal having an average weight of 25 g. The animals are monitored for a total of 16 weeks to rule out any non-specific toxicity.

Toxicity may be bioassayed in vitro on mouse phrenic nerve-hemidiaphragm preparations using the method described in Example 3, below. Briefly, murine phrenic-nerve hemidiaphram preparations are excised and placed in tissue baths to bioassay the toxicity of botulinum toxin in biological specimens, according to the procedures of Kiyatkin et al., *Infect. Immun.* 65:4586-4591, 1997 and Park and Simpson, *Infect. Immun.* 71:1147-1154, 2003. The isolated BoNT/A holotoxin, as well as the isolated wild-type BoNT/A HC50 domain, has affinity for neuromuscular junctions. The affinity of a modified BoNT/A HC polypeptide for neuromuscular junctions may be quantified by measuring the ability of the modified polypeptide to antagonize the actions of the parent holotoxin, as described more completely in the examples below.

The ability of modified BoNT/A HC polypeptides to transcytose epithelial barriers may be assayed according to the method described in Example 2, which is based on Maksymowych and Simpson, *J. Pharmacol. Exp. Ther.* 310:633-641, 2004, using T-84 human epithelial cells. Further examples of such transcytosis assay are described in US 2004/0013687 A2.

Immunogenic compositions useful as vaccines against botulism caused by *C. botulinum* serotype A comprise an effective amount of a modified BoNT/A HC polypeptide according to the invention, and a physiologically acceptable carrier. By "effective amount" is meant an amount capable of inducing a protective immune response in a host. The vaccine composition may comprise one or more adjuvants, particularly adjuvants suitable for transepithelial administration. In one embodiment, the adjuvant is vitamin E, or a derivative thereof.

The modified BoNT/A HC polypeptides of the invention may be administered as vaccines to induce a protective immune response against botulinum toxin by any route effective to achieve such a response. Routes include mucosal routes, as well as parenteral routes, such as intravenous, intramuscular, subcutaneous, and intraperitoneal. Mucosal routes include enteral routes, including oral, rectal and colonic, and certain topical routes, such as intranasal, ocular, vaginal, and pulmonary. Mucosal administration is advantageous as mucosal formulations are less expensive to prepare and administer and are easier to store. Mucosal administration also reduces the possibility of transmission of a blood-born infectious agent. However, the non-neurotropic property of the modified BoNT/A polypeptides of the invention advantageously permits parenteral administration. Other routes of administration contemplated are transdermal and intradermal (e.g., microneedles).

Without wishing to be bound by any theory, it is believed that translocation of the modified BoNT/A HC polypeptides of the invention across epithelial membranes occurs by binding of the molecule to the membrane of an epithelial cell, invagination of the cell's membrane resulting in enclosure of the BoNT/A HC polypeptide within a vesicle of the cell, translocation of the vesicle from one side of the cell to the other (e.g., from the apical face of the cell to its basolateral face, or vice versa), re-integration of the vesicle with the cell's membrane and release of the BoNT from the cell.

The BoNT/A HC polypeptides' epithelial transcytotic capacity therefore can be used for transport of diagnostic or therapeutic entities across epithelial membranes by forming conjugates with such entities. Substantially any type of diagnostic or therapeutic entity can be transported in this manner, limited only by the size capacity of the epithelial vesicles. It is preferred that the selected entity or entities has a molecular mass of about a few hundred daltons (about 100 daltons to about 200 daltons) to about a few tens of thousands of daltons (about 10,000 daltons to about 40,000 daltons). More preferred are entities that have molecular mass that is no greater than about 1000 daltons, and most preferred are entities of molecular mass of about 300 daltons to about 550 daltons. Alternatively, the molecular mass of the entity may be hundreds of thousands, millions, or tens of millions of daltons or more. Thus, transepithelial transport of very large supra-molecular complexes (e.g., a liposome or a virus vector) is contemplated. It is preferred that the size of the entity is not greater than the lumenal capacity of vesicles of cells of the epithelium. Also, the epithelium is preferably a non-keratinized epithelium, and is preferably not kidney epithelium.

Routes of administration useful in practicing the methods of the invention drawn to use of a conjugate of the invention include parenteral, gastrointestinal, vaginal, rectal, colonic, topical, pulmonary, intranasal and ocular. More than one route may be used. In one embodiment, the epithelium which is transcytosed comprises an epithelium of the oral mucosa or gastrointestinal tract, and the conjugate is for oral administration. Well known techniques of protein chemistry and molecular biology can be used to attach the selected entity to the modified BoNT/A HC polypeptide. The conjugate, by virtue of the transepithelial transporting effect of the modified BoNT/A HC polypeptide, is able to translocate from the gut to the general circulation so that the selected entity, when administered orally, would reach the general circulation. Where the entity is a selected antigen, a systemic immune response would be evoked against the antigen.

Suitable entities that can be linked to the modified BoNT/A HC polypeptides of the invention may include organic or inorganic substances (for example, ceramic particles), radionuclides, small organic or inorganic chemical compounds, polymeric materials (e.g., (tetrafluoroethylene polymers, chitosans), polypeptides (including, for example, single- and multi-subunit proteins such as enzymes, antibodies, and polypeptide epitopes of a pathogen), nucleic acids, and nucleic acid vectors (e.g., virus vectors containing an expressible nucleic acid). According to one embodiment, the therapeutic entity comprises a drug or prodrug.

According to one embodiment, a conjugate is formed between a modified BoNT/A HC polypeptide as provided herein and at least one antigen, to induce an immune response against the antigen. The conjugate may therefore be used as an immunogenic composition. Optionally, the immunogenic composition comprising the conjugate further comprises a pharmaceutically acceptable carrier. The immune response induced by the conjugate may nor may not be a protective immune response. In one embodiment, the entity comprises an immunogenic epitope of a pathogen of the animal. The immunogenic epitope may be protein or non-protein. In one embodiment, the immunogenic epitope is an immunogenic portion of a protein associated with a pathogen of a mammal. The modified BoNT/A HC polypeptide facilitates delivery of the epitope to the bloodstream of the animal, thereby inducing generation of an immune response against the epitope. A protective immune response provoked can thereafter inhibit or prevent pathology caused by the pathogen in the animal. Non-protein antigens from which suitable epitopes may be obtained include carbohydrates and nucleic acids.

In one embodiment, the conjugate comprises an antigen linked to a modified BoNT/A HC polypeptide, wherein the antigen induces an immune response in a vertebrate when an epithelium of the vertebrate is contacted with the conjugate. In another embodiment, the antigen linked to a modified BoNT/A HC polypeptide induces protective immunity against a pathogen of a vertebrate when the antigen is delivered to the circulation of the vertebrate. The conjugate is therefore useful in methods of vaccinating a vertebrate. In one embodiment, the antigen is an immunogenic portion of a protein associated with a pathogen. The antigen may be derived from any pathogen. Preferably, the pathogen is a pathogen of a mammal. It should be appreciated that the antigen may comprise an antigen of a *Clostridium* neurotoxin, especially a *Clostridium botulinum* neurotoxin, either BoNT/A or any other BoNT serotype. Thus, while the modified BoNT/A HC polypeptide may comprise a vaccine in its own right against *C. botulinum* intoxication due to its intrinsic immunogenicity against BoNT/A, it may also be used for its epithelial transcytotic capacity in forming conjugates with other immunogenic Clostridial antigens for vaccination.

The methods of the invention may be practice with any animal. Animals are preferably vertebrates, more preferably mammals and more preferably still, human. Non-human animals to which the methods of the inventions may be applied, for example, primates, mice, rats, cattle, sheep, goats, horses, canines, felines and the like. In one embodiment, the conjugates described herein are useful as vaccines for inducing protective immunity in vertebrates, such as mammals, reptiles or fish and can be used for vaccination against substantially any human or other vertebrate pathogen (viral, bacterial, prion), including pathogens that may be weaponized and used as agents of biological warfare, as are known or to be developed in the art.

For example, the pathogen against which the vaccine compositions of the invention may be formulated can be *Plasmodium falciparum* (the causative agent of malaria), *Bordetella pertussis* (the causative agent of whooping cough), meningitis, measles viruses, mumps viruses, influenza viruses, hepatitis viruses, Pneumococcal viruses, Poliovirus, varicella viruses, rabies viruses, and the human immunodeficiency virus. Additionally, the immunogenic epitope for use as an entity can be selected to provoke an immune response against, for example, the pathogens *Bacillus anthracis* (causative agent of anthrax), *Pseudomonas pseudomallei*, *Clostridium botulinum* toxin (causative agent of botulism), *Yersinia pestis* (causative agent of the plague), *Vibrio cholera*, *Variola major* (causative agent of smallpox), *Francisella tularensis* (causative agent of tularemia), *Salmonella typhi* (the causative agent of typhoid fever), virus(es) that are the causative agents of viral hemorrhagic fevers (e.g., Crimean-Cong hemorrhagic fever virus), *Corynebacterium diptheriae*, *Coxiella burnetti* (causative agent of Q fever), organisms of the genus *Brucella* (e.g., *Brucella abortus, Brucella suis, Brucella melitensis, Brucella canis*) (causative agent(s) of brucellosis), saxitoxin, Venezuelan equine encephalitis viruses, *Burkholderia mallei* (causative agent of glanders), the ricin toxin of *Ricinus communis*, the epsilon toxin of *Clostridium perfringens, Clostridiom tetani, Staphylococcus* enterotoxin B, Nipah virus, Hantavirus, Rift Valley fever virus, virus(es) that are the causative agents of tick-borne encephalitis, Staphylococcal enterotoxin B, trichothecene mycotoxins, the causative agent of Yellow fever, the causative agents of multi-drug resistant tuberculosis, and the coronavirus that is the causative agent of Severe Acute Respiratory Syndrome (SARS). The immunogenic epitope that is the entity may also be an epitope that provokes immunity against insect or reptile venom or against various parasites.

The entity or entities may comprise a molecule that is able to bind specifically with another molecule in the bloodstream of the animal to which the conjugate is to be administered. Such entities include, but are not limited to, aptamers, including nucleic acid aptamers and peptide aptamers, and antibody substances such as tetra-subunit immunoglobulins and single-chain antibodies and individual members or fragments of receptor-ligand binding pairs (e.g., tumor necrosis factor alpha and its cell-surface receptor). An "antibody substance" means an immunoglobulin molecule or an immunologically active portion of an immunoglobulin molecule, i.e., a molecule that contains an antigen binding site which specifically binds an antigen. A molecule that specifically binds with an antigen is a molecule that binds the antigen but does not substantially bind other molecules. Examples of immunologically active portions of immunoglobulin molecules include the F(ab) and the F(ab')$_2$ fragments which can be generated by treating the antibody with an enzyme such as papain or pepsin, respectively. The term also includes polyclonal and monoclonal antibodies. The term "monoclonal antibody" or "monoclonal antibody composition" refers to a population of antibody molecules that contain only one species of an antigen binding site capable of immunoreacting with a particular epitope.

In yet another important embodiment, the entity is an agent that exhibits a catalytic or biological activity in vivo. Examples of such agents include cytotoxins, such as ricin; enzymes, such as proteases (e.g., tissue-type plasminogen activators or urokinase-type plasminogen activators); and enzyme inhibitors. The entity can also be a detectable label, such as a contrast agent, a radio-labeled antibody substance, or a radioisotope, such as 3H, 35S, 123I, and/or 131I.

It may be desirable that the linked entity is a larger entity that encompasses or incorporates numerous smaller therapeutic or immunogenic agents. For example, entities which may be used to transport numerous smaller therapeutic, diagnostic or immunogenic agents include liposomes, resealed RBCs, micelles, microspheres, and microparticles.

In the conjugates of the invention, the selected entity (or entities) is linked to the selected modified BoNT/A HC polypeptide. A single BoNT/A HC polypeptide can be linked to one or more entities that are the same or are different. Alternatively, a single entity can be linked with multiple BoNT/A HC polypeptides (each of which may be the same or different).

The entity may be linked to the modified BoNT/A HC polypeptide at any location, as long as the transcytotic capability of the fragment is not significantly impaired. For example, the entity may be linked to or near the carboxy terminus of the modified BoNT/A HC polypeptide. It is preferred that the entity is linked at or near the amino terminus end of the BoNT/A HC polypeptide.

The nature of the linker between the entity and the modified BoNT/A HC polypeptide in forming the conjugate of the invention may vary. The precise chemistry, linker, or method is not critical. The linkage must merely be sufficiently strong or resilient that the fragment does not dissociate from the entity upon vesicular encapsulation of the BoNT/A HC polypeptide by the epithelial cell. The entity and the BoNT/A HC polypeptide may be linked by a covalent bond, such as, for example, a peptide bond. However, strong non-covalent linkage can also be used.

The linker may also be an intervening molecule, which may or may not have a chemical, therapeutic, or diagnostic function as well as its linking function. Examples of intervening molecules that can be used as linkers include biotin, avidin, or an antibody substance. Linkers of this type may be interposed between the entity and the fragment.

In the case where the selected entity or entities is a peptide or polypeptide, the entity can be linked to the modified BoNT/A HC polypeptide by peptide bond(s), thereby forming a unitary polypeptide comprising the entity and the BoNT/A HC polypeptide. For example, a unitary polypeptide can be prepared that comprises both the modified BoNT/A HC polypeptide and the selected entity. Such polypeptides can be prepared in any manner known or to be developed in the art, such as by expression of a fusion polypeptide from a recombinant expression vector, or by chemical synthesis, such as, for example, the solid-phase method.

The entity may also be linked by incorporation of the modified BoNT/A HC polypeptide into the entity itself. For example, if the entity is a liposome, the BoNT/A HC polypeptide may include a specific domain that permits a portion of the BoNT/A HC polypeptide to penetrate and be maintained within the structure of the liposome, while the transcytotic portion of the BoNT/A HC polypeptide remains unimpaired.

Depending on the desired use/route of administration intended for the conjugate, methods can also be used to link the entity and the BoNT/A HC polypeptide in a stable manner, or chemically or biologically unstable or reversible manner. Thus, therapeutic or diagnostic entity can be linked to the modified BoNT/A HC polypeptide to yield two broad groups of administered molecules: (1) conjugates of modified BoNT/A HC polypeptides and therapeutic or diagnostic entities with biologically stable linkages, and (2) conjugates of modified BoNT/A HC polypeptides and therapeutic or diagnostic entities having biologically or chemically unstable linkages, which dissociate upon reaching the target tissue, e.g. the bloodstream. For example, the linkage may be enzyme cleavable by an enzyme co-administered to the patient or that is known to be present in the anatomical area to which the composition is delivered.

Examples of chimeric therapeutic techniques are described generally by Lautenslager, G. T. and Simpson, L. L., "Chimeric Molecules Constructed with Endogenous Substances," Advances in Molecular and Cell Biology, Vol. 9, pp. 233-262, JAI Press, Inc. (1994). For example, a therapeutic peptide could be attached to a modified BoNT/A HC polypeptide, thus creating an agent which possesses the characteristics of the substituent yet is capable of transepithelial administration, especially oral administration.

The entity and the modified BoNT/A HC polypeptide can be made separately and thereafter linked, or they can be made simultaneously.

In an embodiment of the invention, the conjugate may be a vaccine against a BoNT, in which the modified BoNT/A HC polypeptide and the entity exist as an integral polypeptide molecule, and the linker is therefore a peptide bond. In this embodiment of the invention, the modified BoNT/A HC polypeptide/entity integral polypeptide molecule comprises at least that portion of the sequence of the full length BoNT, preferably a BoNT HC, that encodes an immunogenic epitope that provokes an immune response to the BoNT. The BoNT antigen comprising the entity may be derived from any BoNT serotype. In one embodiment, the BoNT antigen comprises an antigen of BoNT/A HC, and the conjugate comprises the modified BoNT/A HC polypeptide containing the mutated ganglioside binding motif linked to a noncontiguous portion of the BoNT heavy chain.

Regardless of the epitope or the specific type of entity utilized, the immune response elicited may be a systemic immune response or a mucosal immune response. Depending on the circumstances in which the immunogenic compositions and methods of the invention are to be applied, it may be desirable to elicit a mucosal immune response, rather than a systemic response, especially when the antigen against which immunity can be produced can be utilized in both a beneficial and a detrimental/toxic manner.

As an example, it is known that botulinum toxin is a potent toxin that is used as an agent of warfare or bioterrorism. Thus, immunization using the compositions and methods of the invention against botulinum toxin may be desirable. However, botulinum toxin is commonly used as a therapeutic agent to treat disorders that are characterized by an excessive and involuntary release of acetylcholine. Thus, an individual having a systemic immunity to botulinum toxin would be subsequently substantially foreclosed from receiving the benefits of botulinum toxin therapy.

The modified BoNT/A HC polypeptide, and conjugates thereof that are used as vaccines, that evoke substantially only mucosal immunity, thereby avoiding this problem, may be prepared by use of a composition that contains such a vaccine and an adjuvant that selectively triggers substantially only mucosal immunity. Such adjuvants include, for example, cholera toxin B subunit or unmethylated oligonucleotides. The adjuvants can be associated with or linked to the modified BoNT/A HC polypeptide, or in the case of a conjugate comprising an antigen entity for use as a vaccine, to the modified BoNT/A HC polypeptide or to the linked antigen entity. Alternatively, the adjuvant(s) can be co-administered to the animal.

In another embodiment, the vaccine of the invention can be prepared so as to elicit substantially only mucosal immunity in the animal to which it is administered by including signaling molecules that promote mucosal immune response and/or inhibit systemic immune response in the composition of the invention. Such signaling molecules may include interleukins and transforming growth factors. The signaling molecules may be linked or otherwise associated with the fragment-linked antigen, the fragment itself, or may be co-administered to the animal with the compositions of the invention.

By use of the compositions and methods described herein, transepithelial transport can be accomplished, in most cases, unidirectionally, i.e., from the apical surface of the epithelium to the basolateral surface, or, alternatively from the basolateral surface to the apical surface. The selected epithelium may be any known, although the efficiency of transcytosis may vary depending on the species of vertebrate, the specific epithelium selected, and/or other chemical or physiological factors. For example, it has been demonstrated that, in caertain canine kidney epithelial cell cultures, transport using carboxyterminal fragments of HC, serotype, is less efficient; thus, kidney epithelium is not preferred.

The epithelium to be crossed by the modified BoNT/A HC polypeptide and conjugates thereof is preferably non-keratinized, or has been rendered non-keratinized. Most epithelia other than skin are normally non-keratinized. However, de-keratinization or partial solubilization of skin tissue can enable transdermal use of the compositions and methods described herein. Examples of generally suitable epithelia include gastrointestinal (e.g., oral, esophageal, gastric, ileal, duodenal, jejunal, colon, and anal), nasal, pulmonary, vaginal, and ocular epithelia. Epithelia accessed by peritoneal administration of the compositions described herein can also be suitable.

The invention encompasses the preparation and use of medicaments and diagnostics of pharmaceutical or veterinary compositions comprising a modified BoNT/A HC polypeptide having an entity linked thereto as an active ingredient. Such a pharmaceutical composition may consist of the linked active ingredient alone, in a form suitable for administration to a subject, or the pharmaceutical composition may comprise the linked active ingredient and one or more pharmaceutically acceptable vehicles, one or more additional ingredients, or some combination of these. Administration of one of these pharmaceutical compositions to a subject is useful for treating, ameliorating, relieving, inducing an immune response against, preventing, inhibiting, or reducing any of a variety of disorders in the subject, as described elsewhere in the present disclosure. Administration can also be for achieving a diagnostic result, e.g., the transport of a radionuclide, contrast agent, or other imaging agent, such as radioopaque agents, labeled antibodies, labeled nucleic acid probes, and colored or fluorescent dyes. The active ingredient may be present in the pharmaceutical composition in the form of a physiologically acceptable ester or salt, such as in combination with a physiologically acceptable cation or anion, as is well known in the art.

The therapeutic entities for forming conjugates according to the present invention may comprise, for example, drugs and pro-drugs. Non-limiting examples include: analgesics, α-adrenergic receptor blockers, anti-Alzheimer's disease medications, antianginals, antianxiety drugs, antiarrythmics, antiarthritics, antibiotics, anticholinergic and cholinomimetic agents, antimuscarinic and muscarinic agents, antiadrenergics, anticoagulants/thrombolytics, anticonvulsants/anti-Parkinson medication, anti-depressants, anti-diabetics, anti-diarrheals, anti-epileptics, anti-fungals, anti-gout medications, anti-heartworm medications for dogs, anti-histamines, antihyperlipidemics, anti-hypertensives, anti-inflammatories, anti-infectives, antimigraines, anti-nauseants/anti-emetics, anti-neoplastics/anti-tumor active agents, anti-pruitics, anti-psychotics, anti-pyretics, anti-spasmodics, antivirals, bronchial dilators/anti-asthmatics, bactericides, calcium antagonists, cardiac agents, cardiotonics, central nervous system actives, contraceptives, coronary vasodilators, cough remedies, cold remedies, cytokines, diuretics, fertility active agents, receptor antagonists, growth factors, herbal actives, hormones, hypoglycemics, hypolipidemics, muscle relaxants, ovulation stimulators, peptide active agents, polypeptide active agents, and proteins such as insulin, calcitonin, LHRH and the like. Further examples of therapeutic entities include: immunogenic entities, sedatives and hypnotics, sexual dysfunction active agents, sleep aids, smoking cessation aids, steroids and steroidals, tranquilizers, laxatives, ophthalmic preparations, nutritional supplements, breath fresheners, breath deodorants, saliva substitutes, antigingivitis agents, anti-cavity agents, anti-plaque agents, diagnostic indicators, and local anesthetics. Also included are: active agents for treatment of osteoporosis, hormone replacement, treatment of periodontal disease, antiseptics, corticosteroids, and non steroidal anti-inflammatory agents.

The aforesaid listing of therapeutic entities is meant to be illustrative, and not limiting.

As used herein, the term "pharmaceutically acceptable vehicle" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition and which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a vehicle or one or more other accessory ingredients, and then, if necessary or desirable, shaping or packaging the product into a desired single- or multi-dose unit.

Although the descriptions of pharmaceutical compositions provided are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals, including commercially relevant mammals, such as cattle, pigs, horses, sheep, cats, and dogs; birds, including commercially relevant birds, such as chickens, ducks, quail, geese, and turkeys; fish including farm-raised fish and aquarium fish; and crustaceans, such as farm-raised shellfish and mollusks.

Pharmaceutical compositions that are useful in the methods of the invention may be prepared, packaged, or sold in formulations suitable for gastrointestinal, oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable vehicle, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention will generally comprise from about 1 microgram to about 1 gram of the active ingredient, and preferably comprises from about 100 micrograms to about 100 milligrams of the active ingredient.

In addition to the active ingredient, a pharmaceutical composition of the invention may further comprise one or more additional pharmaceutical agents. Particularly contemplated additional agents include ingredients which can shield the BoNT HC fragment-entity conjugate from the effects of the acidic pH environment of portions of the gastrointestinal tract. Substantially all formulations and devices for effecting enteric delivery known or to be developed can be used.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable vehicle, and at least sufficient liquid to moisten the mixture. Pharmaceutically acceptable excipients used in the manufacture of tablets include, but are not limited to, inert diluents, granulating and disintegrating agents, binding agents, and lubricating agents. Suitable dispersing agents include, but are not limited to, potato starch and sodium starch glycolate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Suitable granulating and disintegrating agents include, but are not limited to, corn starch and alginic acid. Binding agents include, but are not limited to, gelatin, acacia, pre-gelatinized maize starch, polyvinylpyrrolidone, and hydroxypropyl methylcellulose. Lubricating agents include, but are not limited to, magnesium stearate, stearic acid, silica, and talc.

Tablets may be non-coated or they may be coated using known or to be developed methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Oral compositions may be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261-268) and a variety of naturally available and modified polysaccharides (PCT GB89/00581) may be used in such formulations.

Pulsed release technology, such as that described in U.S. Pat. No. 4,777,049, may also be used to administer the active agent to a specific location within the gastrointestinal tract. Such systems permit drug delivery at a predetermined time and can be used to deliver the active agent, optionally together with other additives that may alter the local microenvironment to promote agent stability and uptake, directly to the colon, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Emulsifying agents include, but are not limited to, lecithin and acacia. Preservatives include, but are not limited to, methyl, ethyl, or n-propyl para hydroxybenzoates, ascorbic acid, and sorbic acid. Sweetening agents include, for example, glycerol, propylene glycol, sorbitol, sucrose, and saccharin. Thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils, such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non irritating pharmaceutically acceptable excipient which is solid at ordinary room temperature (i.e., about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid vehicle. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid vehicle. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intra-arterial, intramuscular, or intrasternal injection and intravenous, intra-arterial, or kidney dialytic infusion techniques.

Formulations of a pharmaceutical composition suitable for parenteral administration comprise the active ingredient combined with a pharmaceutically acceptable vehicle, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules, in multi dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein. Topically administered formulations should be adapted for application to a non-keratinized epithelial tissue (e.g., the inside of the mouth, nose, or throat), and can be provided together with an applicator or dispenser for achieving such application.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients, such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Pharmaceutical compositions of the invention formulated for intranasal administration. One such composition comprise a coarse powder comprising the active ingredient and having an average particle from about 0.2 to 500 micrometers. Such a formulation is administered in the manner in which snuff is taken i.e., by rapid inhalation through the nasal passage from a container of the powder held close to the nares. Formulations suitable for intranasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid vehicle. Such drops may further comprise buffering agents, salts, or one or more other of the additional ingredients described herein. Other ophthalmalmically-administrable formulations which are useful include those which comprise the active ingredient in microcrystalline form or in a liposomal preparation.

It may be appreciated that the pharmaceutical compositions of the invention may contain, in addition to the active agent, additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., U.S.A., which is incorporated herein by reference.

It is understood that the ordinarily skilled physician or veterinarian will readily determine and prescribe an effective amount of the compound to treat, ameliorate, relieve, inhibit, prevent, reduce a disorder in the subject or to elicit an immune response. In so proceeding, the health care professional may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the disorder.

Another aspect of the invention relates to a kit comprising a modified BoNT/A polypeptide of the invention and an instructional material. In one embodiment, the modified BoNT/A polypeptide is part of an immunogenic composition. In another embodiment, the modified BoNT/A polypeptide is part of a conjugate. As used herein, an "instructional material" includes a publication, a recording, a diagram, or any other medium of expression which is used to communicate the usefulness of the modified BoNT/A polypeptide of the invention for diagnosing, imaging, treating, ameliorating, relieving, inhibiting, preventing, or reducing a disorder in a subject or for administering such a composition via a route described herein. The instructional material may also, for example, describe an appropriate dose of the modified BoNT/A polypeptide of the invention. The instructional material of the kit of the invention may, for example, be affixed to a container which contains a modified BoNT/A polypeptide of the invention or be shipped together with a container which contains the modified BoNT/A polypeptide. Alternatively, the instructional material may be shipped separately from the container with the intention that the instructional material and the modified BoNT/A polypeptide be used cooperatively by the recipient.

The invention also includes a kit comprising a modified BoNT/A polypeptide of the invention and a delivery device for delivering the polypeptide to a subject. By way of example, the delivery device may be a squeezable spray bottle, a metered-dose spray bottle, an aerosol spray device, an atomizer, a dry powder delivery device, a self propelling solvent/powder dispensing device, a syringe, a needle, a tampon, or a dosage measuring container. The kit may further comprise an instructional material as described herein.

The invention is now described with reference to the following Examples. These Examples are provided for the purpose of illustration only. The invention is not limited to these Examples, but rather encompasses all variations which are evident as a result of the teaching provided herein.

EXAMPLES

In the following examples, the mutated residues are identified with respect to the 1296 residue BoNT/A propolypeptide.

Example 1

Preparation of BoNT/A HC50 Molecules

BoNT/A HC50 domain, and a series of single (His1253Trp; Trp1266Leu; and Tyr1267Ser) and double (Trp1266Leu/Tyr1267Ser) point mutant variations thereof, were generated as follows.

SEQ ID NO: 9 is the amino acid sequence for a heavy chain of BoNT/A. SEQ ID NO: 9 is an 846 amino acid polypeptide whose sequence corresponds to residues 451 to 1296 of the BoNT/A propolypeptide (strain 62A). The HC50 fragment used in the examples is a 432 amino acid polypeptide whose sequence corresponds to residues 865 to 1296 of the BoNT/A propolypeptide and to residues 415 to 846 of SEQ ID NO: 9. The gene portion encoding the HC50 fragment of BoNT/A (strain 62A) was cloned into 6×His vector pQE30 (Qiagen; Valencia, Calif.) yielding the expression plasmid pQEHC50A. The resultant HC50 polypeptide is fused to a six histidine tag sequence.

*Escherichia coli* [BL21-codon plus(DE3)-RIL (Stratagene)] was used as a host strain for expression of HC50 domains. Cells were grown in Terrific broth (1.2% peptone, 2.4% yeast extract, 0.94% $K_2HPO_4$ and 0.22% $KH_2PO_4$) (Difco; Sparks, Md.) at 37° C., with shaking to an A600 of 0.6 to 0.8. Isopropyl-β-D-1-thiogalactopyranoside at a final concentration of 0.5 mM was added, and incubation was continued for ca. 12 hr at 25° C. Bacteria from 1 liter of induced culture were harvested by centrifugation (6,000×g, 15 min) at 4° C.

To construct mutants of BoNT/A HC50, point mutations were introduced into BoNT/A HC50 using the QuickChange® Site-Directed Mutagenesis Kit (Stratagene). Mutagenic primers were as follows.

For single mutant His1253Trp:

```
Forward primer:
5'-TTTATAGGATTTTGGCAGTTTAATAAT-3'; (SEQ ID NO: 1)

Reverse primer:
5'-ATTATTAAACTGCCAAAATCCTATAAA-3'; (SEQ ID NO: 2)
```

For single mutant Trp1266Leu:

```
Forward primer:
5'-GTAGCAAGTAATTTGTATAATAGACAA-3'; (SEQ ID NO: 3)

Reverse primer:
5'-TTGTCTATTATACAAATTACTTGCTAC-3'; (SEQ ID NO: 4)
```

For single mutant Tyr1267Ser:

```
Forward primer:
5'-GCAAGTAATTGGTCTAATAGACAAATA-3'; (SEQ ID NO: 5)

Reverse primer:
5'-TATTTGTCTATTAGACCAATTACTTGC-3'; (SEQ ID NO: 6)
```

For double mutant Trp1266Leu/Tyr1267Ser:

```
Forward primer:
5'-GCAAGTAATTTGTCTAATAGACAAATA-3'; (SEQ ID NO: 7)

Reverse primer:
5'-TATTTGTCTATTAGACAAATTACTTGC-3'. (SEQ ID NO: 8)
```

The wild-type and mutant BoNT/A HC50 polypeptides were purified as follows. Host bacterial cells were suspended in 200 ml of bacterial protein extract reagent, B-PER (Pierce; Rockford, Ill.) at 4° C. Lysozyme (Sigma; St. Louis, Mo.) at a final concentration of 0.1 mg/ml, DNase (Sigma) at a final concentration of 0.01 mg/ml, and protease inhibitor cocktail tablet (Roche; Manheim, Germany) were added to the cell suspension and incubated on a rotating shaker for 2 hr. Four hundred ml of 50 mM sodium phosphate containing 300 mM NaCl, pH 8.0, was added to the lysed cell suspension and allowed to stand for 30 min. The suspension was centrifuged at 27,000×g for 40 min to remove precipitate.

The clear supernatant was loaded onto a 5 ml column of Ni-NTA superflow (Qiagen) which was equilibrated with 50 mM sodium phosphate containing 300 mM NaCl, pH 8.0. The column was washed with 50 volumes of washing buffer (50 mM sodium phosphate containing 300 mM NaCl, and 20 mM imidazole, pH 8.0). Bound protein was eluted from the column with a gradient of increasing imidazole (100 ml of 50 mM sodium phosphate containing 300 mM NaCl and 20 mM imidazole, and 100 ml of 50 mM sodium phosphate containing 300 mM NaCl and 250 mM imidazole, pH 8.0). The active fractions (at ~100 mM imidazole) were pooled and dialyzed against 50 mM sodium phosphate, pH 6.8. The dialysate was centrifuged at 27,000×g for 30 min to remove precipitate.

The clear supernatant was loaded onto a 4 ml cation exchange column of CM Sepharose fast flow (Amersham Bioscience; Piscataway, N.J.) equilibrated with 50 mM sodium phosphate, pH 6.8. The column was washed with 50 volumes of 50 mM sodium phosphate, pH 6.8. Bound protein was eluted from the column with a gradient of increasing NaCl (50 ml of 50 mM sodium phosphate and 50 ml of 50 mM sodium phosphate with 500 mM NaCl, pH 6.8). The active fractions (at ~200 mM NaCl) were pooled and dialyzed against 50 mM sodium phosphate, pH 7.4. The purity of BoNT/A HC50 protein was confirmed on 10% SDS polyacrylamide gel electrophoresis and found to be more than 98% homogeneous. Approximately 15-20 mg of pure protein was obtained from 1 L of bacterial culture. Proteins were further confirmed by Western blot analysis using rabbit polyclonal antibodies raised against the heavy chain component of BoNT/A.

For the wild type BoNT/A HC50, a typical yield was ca. 15 mg/L. The final product was essentially homogeneous. The yields of the mutant proteins were closely similar to those obtained for the wild type.

Example 2

Transcytosis Assay

A transcytosis assay for wild type BoNT/A HC50 and Trp1266Leu/Tyr1267Ser dimutant BoNT/A HC50 (SEQ ID NO:14) transport across epithelial cells was carried out essentially as described by Maksymowych and Simpson, *J. Pharmacol. Exp. Ther.* 310:633-641, 2004, using T-84 human epithelial cells.

T84 cell cultures were prepared by growing T-84 in a 1:1 mixture of Dulbecco's modified Eagle's medium (1 g/l D-glucose) and Ham's F-12 nutrient medium supplemented with 5% newborn calf serum, 100 U/ml penicillin, 100 mg/ml streptomycin, 8 µg/ml ampicillin, and 15 mM HEPES. Cultures were maintained at 37° C. in 6% $Coho_2$. T-84 cells were fed every other day and passage (1:2) when 95% confluent, approximately every 4 to 5 days. Passages 75 through 85 were used for the following experiments.

Figure 2:
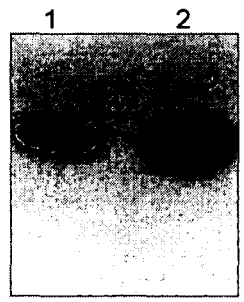
FIG. 2 is a Western blot analysis of polyacrylamide gels of wild type (lane 1) and dimutant (lane 2) forms of BoNT/A HC50 domains. The dimutant form contained the mutation Trp-Tyr→Leu-Ser in the ganglioside binding motif Ser-X-Trp-Tyr. To the apical surface of epithelial monolayers were added $1 \times 10^{-8}$ M of each polypeptide, and 18 hours later, the contents of the basal chamber were assayed by Western blot analysis of polyacrylamide gels. The results show that the two polypeptides possessed comparable abilities to penetrate epithelial barriers.

For the transcytosis assay, T-84 cells were plated at confluent density (ca. $1.5 \times 10^5$ cells) into Tran swells with 0.5 ml of medium in the upper chamber and 1.0 ml in the lower chamber. Membrane integrity and potency of tight junctions were confirmed by measuring transepithelial electrical resistance using an epithelial volt-ohmmeter (WPI; Sarasota, Fla.). The assay was started by adding 0.5 ml medium with 0.2% serum in the upper chamber and phosphate buffered saline in the lower chamber. Transcytosis was initiated by adding the wild type or dimutant BoNT/A HC50 ($1 \times 10^{-8}$ M) to the upper chamber and incubating for 18 h at 37° C. The entire contents of three wells from the lower chamber were collected and concentrated in Centric on 10s micro concentrators to a final volume of 50 µl, of which 15 µl/lane was loaded onto 10% SDS polyacrylamide gels. Samples for Western blot analysis were separated according to Laemmle, *Nature* 227:680-685, 1970. Proteins were transferred to nitrocellulose membranes (Amersham Bioscience) and detected with antibodies against BoNT/A HC50. The results are shown in FIG. 2. The wild type and dimutant forms of BoNT/A HC50 crossed epithelial barriers, and the extent of transcytosis for the two appeared to be comparable.

Example 3

Neuromuscular Bioassay of Wild Type BoNT/A HC50

The most sensitive site for botulinum toxin activity in the periphery is the cholinergic neuromuscular junction. The isolated HC50 domain retains affinity for neuromuscular junctions, and this affinity is typically quantified by measuring the ability of the polypeptide to antagonize the actions of the parent toxin. The ability of HC50 domains to compete for toxin binding sites may therefore be bioassayed with phrenic nerve-hemidiaphragm preparations as follows. This functional assay ensures that the HC50 activity being quantified is relevant to the neuroparalytic actions of the parent toxin.

Murine phrenic-nerve hemidiaphram preparations were excised and placed in tissue baths to bioassay the toxicity of botulinum toxin in biological specimens, according to the procedures of Kiyatkin et al., *Infect. Immun.* 65:4586-4591, 1997 and Park and Simpson, *Infect. Immun.* 71:1147-1154, 2003. Tissues were suspended in physiological buffer that was aerated with 95% $Ohm_2$ and 5% $Coho_2$. Phrenic nerves were stimulated continuously (0.2 Hz; 0.1 to 0.3 msec duration), and muscle twitch was recorded. Toxin-induced paralysis was measured as the reduction in muscle twitch response to neurogenic stimulation. For bioassay of HC50 domains, tissues were suspended in physiological medium at 37° C., and neurogenic responses were monitored for ca. 60 min (i.e., baseline). Temperature was then lowered to 10° C. to substantially abolish the active process of receptor-mediated endocytosis, and nerve-stimulation was halted. Various concentrations of the HC50 polypeptides were added, and incubation was continued for 60 min. BoNT was then added, and incubation was continued for an additional 45 min. The baths were washed 3x to remove all unbound HC50 and BoNT, temperature was raised to 37° C., and nerve stimulation was re-initiated. The paralysis times for control tissues (toxin alone) and for experimental tissues (HC50 polypeptide plus toxin) were monitored.

Using the above protocol, a series of dose-response experiments were done to determine an appropriate test concentration of BoNT/A HC50 that could serve as a comparator for subsequent work. In all cases, the test concentration of the parent toxin was $1 \times 10^{-12}$ M. In the absence of HC50, the average time for BoNT/A to paralyze transmission was 146±13 min.

Then, various concentrations of BoNT/A HC50 were tested in an attempt to find one that would increase paralysis times due to toxin by at least two-fold. A doubling of paralysis times is approximately equivalent to a reduction in apparent toxicity of one order of magnitude. The results, which are illustrated in FIG. 1, indicated that an HC50 concentration of $5 \times 10^{-8}$ M produced the desired outcome. This concentration was selected for all subsequent experiments with single and dimutant forms of BoNT/A HC50.

Example 4

Neuromuscular Bioassay of Mutant BoNT/A HC50

Using a procedure identical to that utilized for wild type BoNT/A HC50 in Example 3, the ability of the BoNT/A HC50 single point mutants His1253Trp, Trp1266Leu, Tyr1267Ser and the dimutant Trp1266Leu/Tyr1267Ser, to antagonize the actions of the parent holotoxin BoNT/A was determined. The three BoNT/A mutants (His1253Trp, Trp1266Leu, Tyr1267Ser) all had substantially diminished ability to antagonize their parent toxin (Table 1). When tested at the same concentration as those used with wild type and single mutants, there was no detectable protection against the parent toxin by dimutant Trp1266Leu/Tyr1267Ser. When the dimutant was tested at a concentration that was 10-fold higher, there was still no detectable protection against the holotoxin (Table 1).

TABLE 1

Paralysis Times For Phrenic Nerve-Hemidiaphragm Preparations

| Recombinant Polypeptides[a,b] | Paralysis Time[c] (min ± SEM) | Percent Control |
|---|---|---|
| None (Control) | 146 ± 13 | 100 |
| HC50A Wild type | 300 ± 21 | 205 |
| HC50A His1253Trp | 207 ± 17 | 142 |
| HC50A Trp1266Leu | 161 ± 17 | 110 |
| HC50A Tyr1267Ser | 171 ± 14 | 117 |
| HC50A Trp1266Leu/Tyr1267Ser | 139 ± 12 | 95 |

[a]N = 3 or more per group.
[b]The wild type and single mutants of BoNT/A HC$_{50}$ were tested at a concentration of 5 × 10$^{-8}$M. The dimutant HC$_{50}$ was tested at a concentration of 5 × 10$^{-7}$M.
[c]Amount of time required for toxin to cause 90% reduction in twitch amplitude.

The results show that the single mutants displayed variable losses in affinity, but the dimutant appeared to have lost any meaningful ability to bind to nerve endings. Thus, a dimutant of BoNT/A HC50 (Trp1266Leu/Tyr1267Ser) had no measurable ability to protect neuromuscular junctions against the actions of homologous native toxin, even using a large molar excess of the mutant. This indicates that the dimutant does not bind to nerve endings.

Example 6

Vaccination with Dimutant BoNT/A HC50

The vaccine activity of the BoNT/A HC50 dimutant Trp1266Leu/Tyr1267Ser was established by the following experiments, where the animals were vaccinated with the dimutant BoNT/A HC50, followed by challenge with BoNT/A holotoxin.

A. Vaccination

Balb/C mice (female, 18-20 g) were purchased from Charles River Laboratories (Wilmington, Mass.). All animals were housed in the animal care facility at Thomas Jefferson University and allowed unrestricted access to food and water. All procedures involving animals were reviewed and approved by the Thomas Jefferson University Institutional Animal Care and Use Committee. Antigen (BoNT/A HC50 dimutant) was administered by the intranasal route, during which mice were lightly anesthetized with isoflurane (Isothesia; Abbott Laboratories; North Chicago, Ill.). The bodies of animals were maintained in an upright position to minimize drainage into the posterior pharynx. Each protein (20 μg) was administered by a single application of a 20 μl phosphate-buffered saline solution (pH 7.0) to the nares. In certain experiments the animals received antigen in the presence of an adjuvant (d-α-tocopheryl polyethylene glycol 1000 succinate ("vitamin E TPGS"); 1.0%, W/v). During a standard protocol, mice were vaccinated at times 0, 2 weeks and 4 weeks. At 6 weeks, aliquots of blood were obtained for quantitation of IgA and IgG by ELISA assay, and animals were challenged with toxin (BoNT/A) as follows.

B. Challenge with *Botulinum* Toxin.

The most characteristic outcome of toxin action is muscle weakness and paralysis. This outcome is easily discernible as decreased locomotion and ultimately as a failure of respiration. During challenge experiments, animals received large doses of toxin that typically produce respiratory failure and death within 1 to 2 hours. To minimize pain and suffering, animals were not allowed to die from paralysis of respiration. Instead, animals were observed throughout the protocols. When signs of neuromuscular weakness became obvious (i.e., absence of locomotor activity), animals were sacrificed in accordance with AALAC guidelines (e.g., Coho 2).

C. ELISA Assay.

Antibody titers in mouse serum were determined by standard procedures. Briefly, flat bottom, 96 well Corning plates (Corning Incorporated, Corning, N.Y.) were coated with the HC50 domains of botulinum toxin (300 ng/well) and incubated at 4° C. overnight, followed by washing with phosphate buffered saline plus Tween (0.1%) pH 7.4. The plates were blocked with 1% bovine serum albumin. Two-fold serial dilutions of serum samples were added to the plates and incubated at 37° C. for 60 minutes. IgG titers were determined using peroxidase-conjugated goat anti-mouse IgG (Sigma-Aldrich, Inc., St. Louis, Mo.) and IgA titers were determined using peroxidase-conjugated goat anti-mouse IgA (Santa Cruz Biotechnology, Inc., Santa Cruz, Calif.). Secondary antibodies were diluted 1:1000 in phosphate buffered saline. The primary and secondary antibodies were incubated for 30 min at 37° C., after which 2,2'-azino-bis(3-ethylbenthiazoline-6-sulfonic acid) was added as a substrate, and the plates were incubated for an additional 30 min at 37° C. End point titers were determined as the reciprocal of the last dilution yielding an absorbance at 405 nm that was above the control value (pre-immune serum).

D. Results

As indicated in Table 2, all control animals became visibly ill within about 100 minutes of challenge with neurotoxin. All vaccinated animals survived for more than four days, and there were no signs of illness in any of these animals.

TABLE 2

Resistance To Challenge With Botulinum Toxin Type A

| Vaccination Paradigm[a] | Challenge Dose | Survival |
|---|---|---|
| Control | 10$^3$ LD50 | 0/10 |
| Antigen Alone | 10$^3$ LD50 | 10/10 |
| Control | 10$^4$ LD50 | 0/10 |
| Antigen plus Adjuvant | 10$^4$ LD50 | 10/10 |

[a]N = 10 per group.

Figure 3:
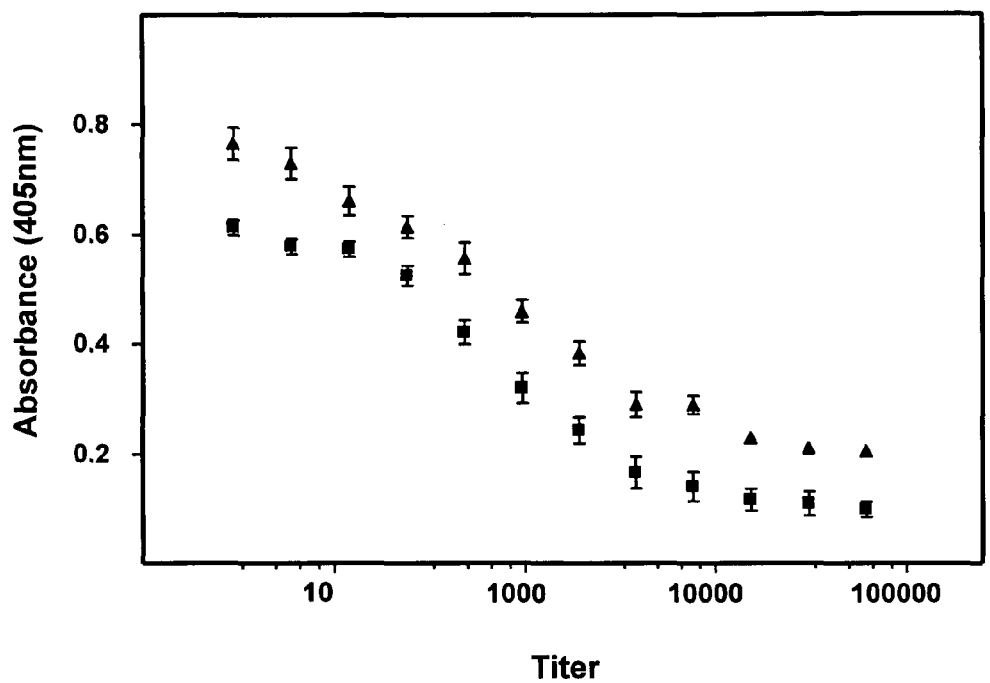
FIG. 3 is plot of an assay for IgA (■) and IgG (▲) in serum samples of mice vaccinated with the dimutant form BoNT/A HC50. Mice (group N=10) were vaccinated with the dimutant form. Serum samples were obtained at the end of the protocol on day 42, and assayed for IgA (■) and IgG (▲). The results demonstrate that the dimutant polypeptide evoked a significant response with both immunoglobulin types.
Figure 4:
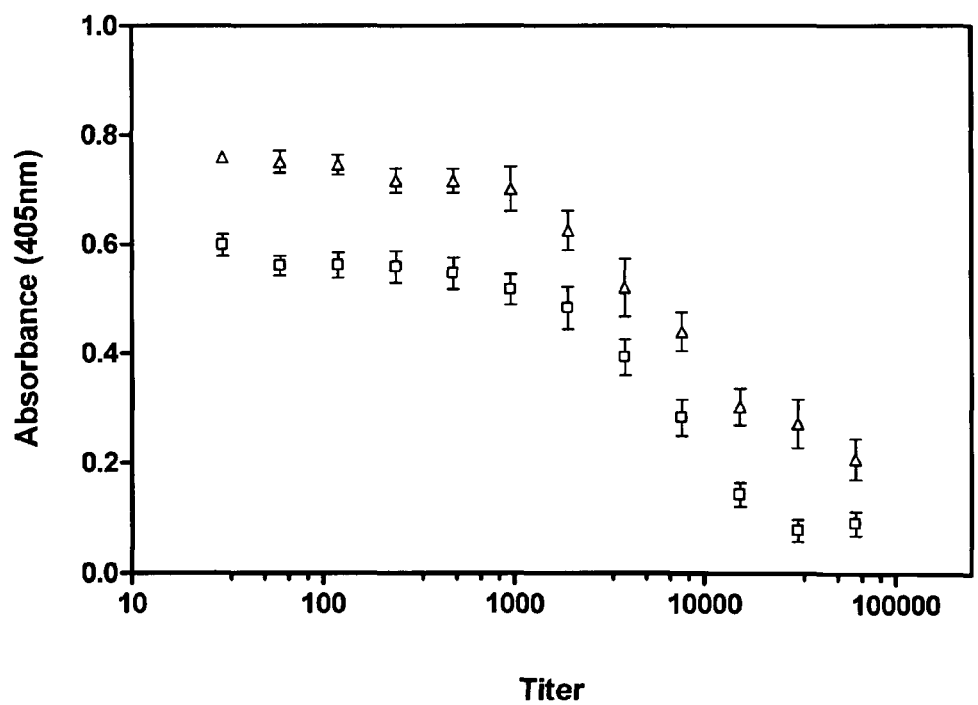
FIG. 4 is plot of an assay for IgA (□) and IgG (Δ) in serum samples of mice vaccinated with the dimutant from BoNT/A HC50 plus adjuvant (vitamin E). Mice (group N=10) were vaccinated with the dimutant form plus vitamin E. Serum samples were obtained at the end of the protocol on day 42, and assayed for IgA and IgG. The results demonstrate that the adjuvant helped to evoke IgA (□) and IgG (Δ) responses that were greater than those in the absence of adjuvant (i.e., FIG. 3).

The dimutant form of BoNT/A HC50 evoked immunoglobulin responses. However, the magnitudes of the IgA responses were less than those of the IgG responses (FIG. 3). The IgA response in the presence of adjuvant (vitamin E) was considerably greater than that in the absence of adjuvant (FIG. 4). The IgG response, whether in the absence or presence of adjuvant, was substantial, but it was elevated still further by adjuvant.

Example 7

Neutralizing Antibody and Neuromuscular Blockade

The following experiment establishes that even though dimutant BoNT/A HC50 domain has lost affinity for cholinergic nerve endings, anti-mutant HC50 antibody raised upon vaccination with the dimutant still possess the ability to block toxin binding to neuronal cells.

Figure 5:
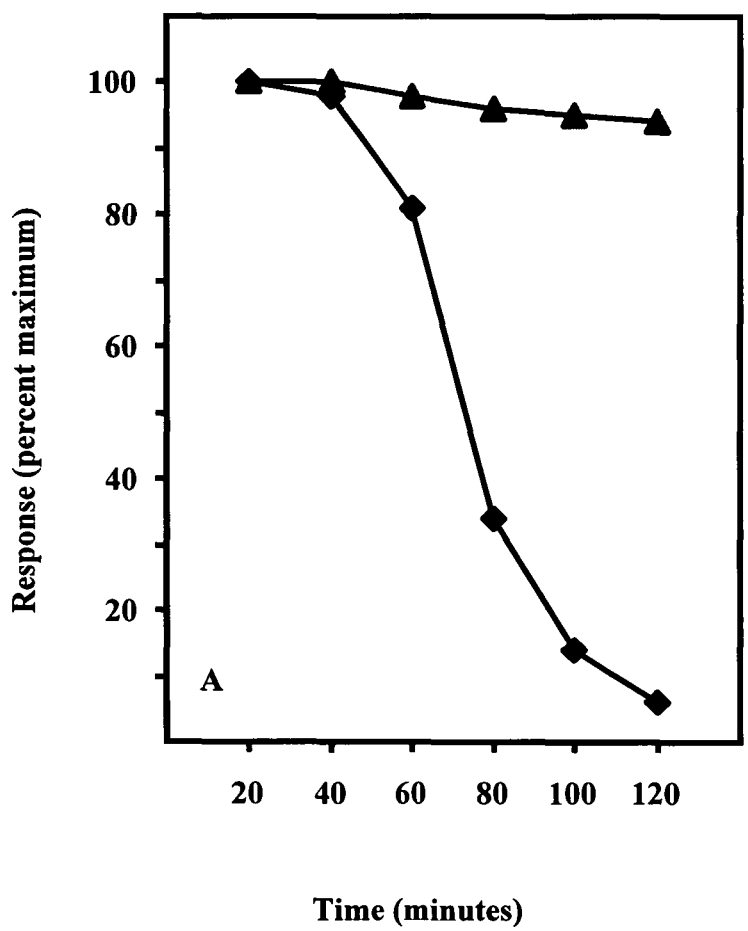
FIG. 5 is a plot of the response of murine phrenic nerve-hemidiaphragm preparations to paralysis by BoNT/A (♦) alone, or BoNT/A in the presence of antiserum obtained from mice vaccinated with the dimutant form of BoNT/A HC50 (▲; 0.1 ml; 30 min; room temperature). Control tissues (♦; toxin alone) paralyzed within 120 minutes, whereas experimental tissues (toxin plus antiserum; ▲) did not paralyze, even when monitored for 240 minutes.

Antiserum (0.1 ml) from mice that had been vaccinated with dimutant BoNT/A HC50 was incubated with homologous toxin for 60 min at room temperature, after which the mixture was added to phrenic nerve-hemidiaphragm preparations. The results, which are illustrated in FIG. 5, show that control tissues (toxin alone) paralyzed within about 120 min. However, experimental tissues (toxin previously incubated with antiserum) did not paralyze. Thus, the introduction of the two mutations (Trp1266Leu and Tyr1267Ser) into the BoNT/A HC50 polypeptide did not abolish its ability to induce antibodies that block toxin action on the neuromuscular junction.

Example 8

Preparation of BoNT/A HC Fragment Fusion to BoNT/A Light Chain

A synthetic gene portion encoding the light chain (LC; SEQ ID NO:27; corresponds to residues 1 to 438 of BoNT/A propolypeptide) was fused with a synthetic gene portion encoding HC66 (residues 242 to 846 of SEQ ID NO: 9; corresponds to residues 692 to 1296 of BoN/T propolypeptide) and cloned into 6×His vector pET30a (Novagen, San Diego, Calif.) yielding the expression plasmid pET30a$^+$LC-HC66A. SEQ ID NO:28 is the amino acid sequence for the resulting fusion protein, LC-HC66/A. SEQ ID NO:29 is an optimized coding sequence for LC-HC66/A.

A tri-mutant version of LC-HC66A was prepared. The tri-mutant contained the following mutations: Glu224Gln; Trp1266Leu and Tyr1267Ser. Glu224 is the glutamate in the zinc-binding motif present in the light chain. Mutation of zinc-binding motif residues causes loss of activity (see, e.g., U.S. Pat. No. 6,051,239) of the light chain zinc-dependent metal loendoprotease.

To construct the tri-mutant LC-HC66$_{E224Q, W1266L, Y1267S}$, point mutations were introduced into Lc-HC66 using QuikChange® Site-Directed Mutagenesis Kit (Stratagene). The phosphorylated mutagenic primers were as follows: For Glu224Gln, 5'-pCTGGTGAGCCAGCGTCACCGC-CGGGTCAGT-3' (SEQ ID NO:30) and for Trp1266Leu/Tyr1267Ser, 5'-pCTGAGCAACC-GTCAGATTGAGCGT-TCTTCC-3' (SEQ ID NO:31). The amino acid sequence of LC-HC66$_{E224Q, W1266L, Y1267S}$ is provided in SEQ ID NO:32. An optimized coding sequence for LC-HC66$_{E224Q, W1266L, Y1267S}$ is provided in SEQ ID NO:33.

*Escherichia coli* (BL21-codon plus(DE3)-RIL (Stratagene)) was used as a host strain for expression of LC-H66/A and trimutant LC-HC66/A. Cells were grown in Terrific broth (1.2% peptone, 2.4% yeast extract, 0.94% K$_2$HPO$_4$ and 0.22% KH$_2$PO$_4$) (Difco; Sparks, Md.) at 37° C., with shaking to an A$_{600}$ of 0.6 to 0.8. Isopropyl-β-D-thiogalacto-pyranoside at a final concentration of 0.5 mM was added and incubation was continued for about 20 hr at 12° C. Bacteria from 1 liter of induced culture were harvested by centrifugation (6,000×g, 15 min) at 4° C.

The wild-type and tri-mutant BoNT/A LC-HC66 polypeptides were purified as follows. Host bacterial cells were suspended in 10 ml of 50 mM sodium phosphate containing 300 mM NaCl, pH 8.0. Equal volume of bacterial cell lysis reagent Novagen® BugBuster® (EMD Chemicals Inc., San Diego, Calif.) was added to the cell suspension and allowed to stand for 2 hr on ice. The suspension was centrifuged at 27,000×g for 40 min to remove precipitate. The supernatant was further diluted by adding 100 ml of 50 mM sodium phosphate containing 300 mM NaCl, pH 8.0 and centrifuged again at 27,000×g for 40 min to remove precipitate.

The clear supernatant was loaded onto a 5 ml column of Ni-NTA superflow (Qiagen), which was equilibrated with 50 mM sodium phosphate containing 300 mM NaCl, pH 8.0. The column was washed with 50 volumes of washing buffer (50 mM sodium phosphate containing 300 mM NaCl, and 15 mM imidazole, pH 8.0). Bound protein was eluted from the column with 50 mM sodium phosphate containing 300 mM NaCl and 50 mM imidazole, pH 8.0. The active fractions were pooled and dialyzed against 50 mM Tris-HCl containing 5 mM 2-mercaptoethanol, pH 9.0. The dialysate was centrifuged at 27,000×g for 30 min to remove precipitate.

The clear supernatant was loaded onto a 4 ml cation exchange column of Q Sepharose Fast Flow (Amersham Bioscience, Piscataway, N.J.) equilibrated with 50 mM Tris-HCl containing 5 mM 2-mercaptoethanol, pH 9.0. The column was washed with 50 volumes of 50 mM Tris-HCl containing 5 mM 2-mercaptoethanol and 50 mM NaCl, pH 9.0. Bound protein was eluted from the column with 50 mM Tris-HCl containing 5 mM 2-mercaptoethanol and 200 mM NaCl, pH 9.0. The active fractions were pooled and concentrated with 100K ultrafilter (Amicon, Beverly, Mass.).

The concentrated sample was loaded onto Sephacryl S-100 HR column (2.5×100 cm) (Amersham Bioscience), which was equilibrated with gel filtration buffer (110 mM NaHCO$_3$, pH 8.5) and eluted at 0.3 ml/min into 0.3 ml fractions. Active fractions were collected, concentrated and stored at −80° C. The purity of HC$_{50}$A protein was confirmed on 10% SDS polyacrylamide gel electrophoresis. Approximately 0.2 mg of pure HC$_{50}$A was obtained from 1 L of bacterial culture. Proteins were further confirmed by Western blot analysis using rabbit polyclonal antibodies raised against the light chain (LC) and heavy chain (HC) components of BoNT/A. The yield of the tri-mutant protein was closely similar to those obtained for the wild type BoNT/A LC-HC66.

It has been demonstrated previously that an LC polypeptide and an HC66 polypeptide are each immunogenic and can induce a response that is protective against toxin challenge. Thus, it is contemplated that combining these two molecules into one polypeptide will result in an immunogenic polypeptide that can induce a protective immune response. Furthermore, the double mutation Trp-Tyr→Leu-Ser in the ganglioside binding motif present in LC-HC66$_{E224Q, W1266L, Y1267S}$ is expected to preclude any meaningful ability of the molecule to bind nerve endings.

All references cited herein are incorporated by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A modified BoNT/A polypeptide comprising amino acid sequence SEQ ID NO: 14.

2. An immunogenic composition comprising a modified BoNT/A polypeptide according to claim 1, and a pharmaceutically acceptable carrier.

3. A method of inducing an immune response to BoNT/A in an animal comprising administering to said animal an effective amount of the immunogenic composition according to claim 2.

4. The method according to claim 3, wherein the immunogenic composition is administered by at least one of the following routes: parenteral, gastrointestinal, vaginal, topical, pulmonary, intranasal and ocular.

5. The method for protecting an animal from botulism, comprising administering to said animal an effective amount of the immunogenic composition according to claim 2.

6. The method according to claim 5, wherein the immunogenic composition is administered by at least one of the following routes: parenteral, gastrointestinal, vaginal, topical, pulmonary, intranasal and ocular.

7. A conjugate comprising a modified BoNT/A polypeptide according to claim 1, linked to a diagnostic or therapeutic entity.

8. A conjugate according to claim 7, wherein the entity is an antigen.

9. A conjugate according to claim 8 wherein the antigen is a polypeptide.

10. A conjugate according to claim 9, wherein the entity is linked to the modified BoNT/A polypeptide by a peptide bond.

11. The conjugate according to claim 10, wherein the entity is an immunogenic portion of a protein associated with a pathogen of a mammal.

12. The conjugate of claim 11, wherein the mammal is a human.

13. The conjugate according to claim 11, wherein the pathogen is selected from the group consisting of *Plasmodium falciparum, Bacillus anthracis, Bordetella pertussis, Brucella abortus, Brucella canis, Brucella melitensis, Brucella suis, Burkholderia mallei, Clostridium perfringens, Clostridium tetani, Clostridium botulinum, Corynebacterium diptheriae, Coxiella burnetii*, Crimean-Congo hemorrhagic fever virus, the coronavirus that is the causative agent of Sudden Acute Respiratory Syndrome (SARS), the causative agent of Yellow Fever, the causative agents of multidrug resistant tuberculosis, *Francisella tularensis*, Hantavirus, hepatitis viruses, human immunodeficiency virus, influenza viruses, measles virus, meningitis, mumps viruses, Nipah virus, Pneumococcal viruses, *Poliovirus, Pseudomonas pseudomallei*, the ricin toxin of *Ricinus communis*, Rift Valley fever virus, rabies viruses, *Salmonella typhi*, Staphylococcal enterotoxin B, trichothecene mycotoxins, *Varicella* viruses, saxitoxin, Venezuelan equine encephalitis viruses, viruses that are the causative agents of tickborne encephalitis, *Variola major, Vibrio cholera*, and *Yersinia pestis*.

14. The conjugate according to claim 13, wherein the pathogen is *Clostridium botolinum*.

15. The conjugate according to claim 9, wherein the entity is an antibody substance.

16. The conjugate according to claim 7 wherein the entity is a drug or pro-drug.

17. The conjugate according to claim 7 wherein the entity is a diagnostic entity.

18. A method for delivery of a therapeutic or diagnostic entity across a non-keratinized epithelium of an animal comprising:
   contacting an epithelium of said animal with a conjugate comprising said therapeutic or diagnostic entity linked to a modified BoNT/A polypeptide, the modified BoNT/A polypeptide comprising the amino acid sequence of SEQ ID NO: 14;
   whereby the therapeutic or diagnostic is transported across the non-keratinized epithelium.

19. The method according to claim 18, wherein the epithelium is gastrointestinal, nasal, pulmonary, vaginal, or ocular epithelium.

20. The method according to claim 19, wherein the gastrointestinal epithelium is oral, esophageal, gastric, ileal, duodenal, jejunal, or colon epithelium.

21. The method according to claim 18 wherein the animal is a human.

22. A method of inducing an immune response in a vertebrate against a selected antigen comprising:
   contacting an epithelium of said vertebrate with an effective amount of a conjugate comprising said antigen linked to a modified BoNT/A polypeptide, the modified BoNT/A polypeptide comprising the amino acid sequence of SEQ ID NO: 14;
   whereby an immune response to the antigen is induced in the vertebrate.

23. The method according to claim 22, wherein the epithelium is gastrointestinal, nasal, pulmonary, vaginal, or ocular epithelium.

24. The method according to claim 23, wherein the gastrointestinal epithelium is oral, esophageal, gastric, ileal, duodenal, jejunal, or colon epithelium.

25. The method according to claim 22 wherein the antigen is an immunogenic portion of a protein associated with a pathogen of a mammal.

26. The method according to claim 25 wherein the mammal is a human.

27. The method according to claim 25, wherein the pathogen is selected from the group consisting of *Plasmodium falciparum, Bacillus anthracis, Bordetella pertussis, Brucella abortus, Brucella canis, Brucella melitensis, Brucella suis, Burkholderia mallei, Clostridium perfringens, Clostridium tetani, Clostridium botulinum, Corynebacterium diptheriae, Coxiella burnetii*, Crimean-Congo hemorrhagic fever virus, the coronavirus that is the causative agent of Sudden Acute Respiratory Syndrome (SARS), the causative agent of Yellow Fever, the causative agents of multi-drug resistant tuberculosis, *Francisella tularensis*, Hantavirus, hepatitis viruses, human immunodeficiency virus, influenza viruses, meningitis, measles virus, mumps viruses, Nipah virus, Pneumococcal viruses, Poliovirus, *Pseudomonas*

*pseudomallei*, the ricin toxin of *Ricinus communis*, Rift Valley fever virus, rabies viruses, *Salmonella typhi*, Staphylococcal enterotoxin B, trichothecene mycotoxins, *Varicella* viruses, saxitoxin Venezuelan equine encephalitis viruses, viruses that are the causative agents of tick-borne encephalitis, *Variola major*, *Vibrio cholera*, and *Yersinia pestis*.

28. The method according to claim 27, wherein the pathogen is *Clostridium botulinum*.

29. The modified BoNT/A polypeptide according to claim 1, further comprising a BoNT light chain fused thereto.

* * * * *